US008901126B2

(12) United States Patent
Kaizawa et al.

(10) Patent No.: US 8,901,126 B2
(45) Date of Patent: Dec. 2, 2014

(54) SUBSTITUTED IMIDAZO[1,5-A]QUINOXALIN-4-ONES ARE USEFUL FOR PREVENTING OR TREATING STORAGE DYSFUNCTION, VOIDING DYSFUNCTION AND BLADDER/URETHRAL DISEASES

(71) Applicant: Astellas Pharma Inc., Chuo-ku (JP)

(72) Inventors: Hiroyuki Kaizawa, Tokyo (JP); Mari Sugita, Tokyo (JP); Hirofumi Yamamoto, Tokyo (JP); Kazunori Kamijo, Tokyo (JP); Kazuyuki Tsuchiya, Tokyo (JP); Ryushi Seo, Tokyo (JP); Satoshi Yamamoto, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/788,770

(22) Filed: Mar. 7, 2013

(65) Prior Publication Data

US 2013/0296329 A1    Nov. 7, 2013

Related U.S. Application Data

(63) Continuation-in-part of application No. PCT/JP2011/070287, filed on Sep. 6, 2011.

(30) Foreign Application Priority Data

Sep. 7, 2010   (JP) ................... 2010-200402

(51) Int. Cl.
A61K 31/4985    (2006.01)
C07D 241/38     (2006.01)
C07D 487/04     (2006.01)
C07D 519/00     (2006.01)

(52) U.S. Cl.
CPC ............ C07D 487/04 (2013.01); C07D 519/00 (2013.01)
USPC ........... 514/250; 544/346; 546/113; 548/469; 549/429

(58) Field of Classification Search
CPC .................. A61K 31/4985; C07D 241/38
USPC ........... 514/250; 544/346; 546/113; 548/469; 549/429
See application file for complete search history.

(56) References Cited

U.S. PATENT DOCUMENTS

| 5,504,085 | A | 4/1996 | Jacobsen et al. |
| 2009/0203703 | A1 | 8/2009 | Gotanda et al. |
| 2009/0318478 | A1 | 12/2009 | Asagarasu et al. |
| 2010/0048556 | A1 | 2/2010 | Okada et al. |
| 2010/0113484 | A1 | 5/2010 | Gotanda et al. |
| 2011/0319385 | A1* | 12/2011 | Kaizawa et al. .......... 514/213.01 |

FOREIGN PATENT DOCUMENTS

| EP | 0 400 583 A1 | 12/1990 |
| EP | 2 103 613 A1 | 9/2009 |
| EP | 2 404 922 A1 | 1/2012 |
| JP | 8-507536 | 8/1996 |
| JP | 2005-511575 A | 4/2005 |
| WO | WO 93/12113 | 6/1993 |
| WO | WO 93/17025 | 9/1993 |
| WO | WO 94/21639 | 9/1994 |
| WO | WO 96/08492 | 3/1996 |
| WO | WO 96/08493 | 3/1996 |
| WO | WO 99/09845 | 3/1999 |
| WO | WO 03/037899 A1 | 5/2003 |
| WO | WO 2006/135080 | 12/2006 |
| WO | WO 2008/018306 | 2/2008 |
| WO | WO 2008/072778 | 6/2008 |
| WO | WO 2008/072779 | 6/2008 |
| WO | WO 2010/026214 | 3/2010 |
| WO | WO 2010/084438 | 7/2010 |
| WO | WO 2010/101230 A1 | 9/2010 |

OTHER PUBLICATIONS

International Search Report issued Nov. 15, 2011 in International Application No. PCT/JP2011/070287 (w/ English translation).
International Preliminary Report on Patentability issued Nov. 15, 2011 in International Application No. PCT/JP2011/070287.
Thiyagarajan, "α-Adrenoceptor Antagonists in the Treatment of Benign Prostate Hyperplasia", Pharmacology, 2002, vol. 65, pp. 119-128.
Shah et al, "Distigmine Bromide and Post-Prostatectomy Voiding", British Journal of Urology, 1983, vol. 55, pp. 229-232.
Finkbeiner, "Is Bethanechol Chloride Clinically Effective in Promoting Bladder Emptying? A Literature Review", The Journal of Urology, 1985, vol. 134, pp. 443-449.
Bloch et al, "Distribution of Nitric Oxide Synthase Implies a Regulation of Circulation, Smooth Muscle Tone, and Secretory Function in the Human Prostate by Nitric Oxide", The Prostate, 1997, vol. 33, pp. 1-8.
Toprakçi et al, "Age-associated changes in nitric oxide metabolites nitrite and nitrate", Int. J. Clin. Lab. Res., 2000, vol. 30, pp. 83-85.
Fisher et al, "Isolation and Characterization of PDE9A, a Novel Human cGMP-specific Phosphodiesterase", The Journal of Biological Chemistry, 1998, vol. 273, No. 25, pp. 15559-15564.
Rentero et al, "Identification and distribution of different mRNA variants produced by differential splicing in the human phosphodiesterase 9A gene", Biochemical and Biophysical Research Communications, 2003, vol. 301, pp. 686-692.
Extended European Search Report issued Jun. 5, 2013 in Patent Application No. 10748823.1.
Office Action issued Feb. 5, 2014 in Australian Patent Application No. 2011299936.
Extended European Search Report issued Feb. 4, 2014 in Patent Application No. 11823576.1.
Office Action issued May 28, 2014 in Mexican Patent Application No. 2013-002579 (with English Translation).
Office Action issued on Apr. 8, 2014, in Eurasian Application No. 201390354 (with English Translation).
Chinese Office Action dated Jul. 22, 2014 issued in the corresponding Chinese patent application No. 201180043069.7 (with English translation).

* cited by examiner

Primary Examiner — Douglas M Willis
(74) Attorney, Agent, or Firm — Oblon, Spivak, McClelland, Maier & Neustadt, L.L.P.

(57) ABSTRACT

Substituted imidazo[1,5-a]quinoxalin-4-one compounds of formula (I) described herein exhibit PDE9-inhibitory action and is useful as an active ingredient for an agent for treating and/or preventing storage dysfunction, voiding dysfunction, and bladder/urethral diseases, and the like.

9 Claims, No Drawings

SUBSTITUTED IMIDAZO[1,5-A]QUINOXALIN-4-ONES ARE USEFUL FOR PREVENTING OR TREATING STORAGE DYSFUNCTION, VOIDING DYSFUNCTION AND BLADDER/URETHRAL DISEASES

This application is a continuation-in-part of PCT/JP2011/070287, filed on Sep. 6, 2011, and claims priority to Japanese Patent Application No. 2010-200402, filed on Sep. 7, 2010.

TECHNICAL FIELD

The present invention relates to a quinoxaline compound which is useful as an active ingredient for a pharmaceutical composition, in particular, a pharmaceutical composition for treating storage dysfunction, voiding dysfunction, and bladder/urethral diseases, and the like.

BACKGROUND ART

The important roles of voiding function are urine storage and voiding, which are regulated by a coordinated action of the bladder and the urethra. That is, during the urine storage, the bladder smooth muscle is relaxed and the urethra sphincter is contracted, whereby a state in which urethral resistance is high is maintained, and urinary continence is also maintained. On the other hand, during the voiding, the bladder smooth muscle is contracted while the urethra smooth muscle is relaxed, and the contraction of the external urethral sphincter is also inhibited. Examples of voiding dysfunction include a storage dysfunction such as overactive bladder and the like in which urine cannot be retained during urine storage and a voiding dysfunction in which urine cannot be drained sufficiently due to increase in the urethral resistance and decrease in the bladder contractile force. These two dysfunctions may be expressed simultaneously.

In treatment of a storage dysfunction such as overactive bladder and the like, anticholinergic agents have been used frequently. However, these agents cannot provide a sufficient therapeutic effect, and further, side effects based on the anticholinergic action (dry mouth, gastrointestinal symptoms, eye symptoms, arrhythmias, or the like) appear, and accordingly, administration of the agents may be often interrupted. Further, the anticholinergic agents reduce the bladder contractile force, and are therefore contraindicated for urinary frequency/incontinence accompanying urethral obstruction such as benign prostatic hyperplasia and the like.

Voiding dysfunction is caused by an increase in urethral resistance during voiding or a decrease in the bladder contractile force. As a disease causing an increase in urethral resistance, voiding dysfunction accompanying benign prostatic hyperplasia is well-known, which is characterized by urethral obstruction due to nodular hypertrophy of the prostate tissues. An $\alpha_1$ receptor antagonist has now been used for the purpose of treating voiding dysfunction accompanying benign prostatic hyperplasia (see, for example, Non-Patent Document 1). Other causes of the increase in urethral resistance include functional obstructions such as urethra relaxation failure during voiding or detrusor-external urethral sphincter dyssynergia and the like due to neurological disorders such as diabetes, aging, bone marrow damage, pelvic surgery, and the like. With patients with these diseases, there exist many cases in which the $\alpha_1$ receptor antagonist is ineffective. On the other hand, a decrease in the bladder contractile force during voiding, referred to as underactive bladder, acontractile bladder, neurogenic bladder, or the like, also causes voiding dysfunction. Known factors for decreasing the bladder contractile force include aging, neurological diseases such as diabetes, Parkinson's disease, multiple sclerosis and the like, bone marrow damage, and neurological disorders due to pelvic surgery. Examples of an agent for treating a decrease in the bladder contractile force during voiding include bethanechol chloride which is a muscarinic receptor agonist and distigmine bromide which is a cholinesterase inhibitor. Both of these drugs have side effects, and thus, their satisfactoriness is low (see, for example, Non-Patent Documents 2 and 3). In voiding dysfunction caused by an increase in the urethral resistance or a decrease in the bladder contractile force as described above, residual urine after voiding is observed. Increased residual urine may cause a decrease in effective bladder capacity, and thus, cause overactive bladder symptoms such as urinary frequency and the like, or severe symptoms, such as hydronephrosis in some cases, and in this regard, there is a demand for a therapeutic agent which is more effective than a current therapeutic agent.

It is known that a relaxation system due to nitric oxide (NO) is present in the smooth muscle, and NO produced in the nerve terminals or locally activates soluble guanylate cyclase present in the smooth muscle cells. The activated guanylate cyclase increases cyclic guanosine monophosphate (cGMP) in the cells. On the other hand, the cGMP is degraded into 5'-GMP by phosphodiesterase (PDE) which is an enzyme degrading the cGMP. An increase in the intracellular cGMP concentration is considered to contribute significantly to the smooth muscle relaxation. Therefore, the decrease of the NO-cGMP system causes relaxation failure of the smooth muscle. For example, in patients showing urethral obstruction in benign prostatic hyperplasia or in the elderly as described above, it is reported that NO production is significantly decreased (Non-Patent Documents 4 and 5).

As a subtype of PDE which specifically degrades cGMP, PDE5, PDE6 and PDE9 are known, and among these, PDE9 has a higher substrate affinity than PDE5 and PDE6 (Non-Patent Document 6). Further, from the viewpoint that in the distribution of expression in various tissues, PDE9 is observed at its highest expression in the human prostate (Non-Patent Document 7), it plays an important role in smooth muscle relaxation in lower urethra smooth muscle and a PDE9 inhibitor enhances the relaxation of the urethra via the elevation of cGMP in the tissue. Therefore, it is considered that the PDE9 inhibitor exhibits an effect against voiding dysfunction due to an increase in the urethral resistance. Since the PDE9 inhibitor decreases the urethral resistance, an effect against voiding dysfunction in which the bladder contractile forces are decreased can be expected. In addition, the decrease in residual urine due to improvement of the voiding dysfunction will lead to improvement of overactive bladder symptoms such as urinary frequency and the like or avoidance of renal disorders. Therefore, it is considered that the PDE9 inhibitor is useful as an agent for preventing and/or treating storage dysfunction, voiding dysfunction, and bladder/urethral diseases.

For example, as a compound having a PDE5- and/or PDE9-inhibitory action(s), in Patent Documents 1 and 2, there are disclosed compounds represented by the following formulae (A) and (B), respectively, but there is no specific disclosure of the compounds of the present invention. Further, in Patent Documents 3 and 4, there are disclosed a thienopyrimidine derivative and a quinazoline derivative as compounds having a PDE5- and/or PDE9-inhibitory action(s), respectively. In addition, in Patent Documents 5 and 6, there is disclosed a pyrazolopyridine derivative which has a PDE9-inhibitory action.

Furthermore, in Patent Documents 7 to 12, there are disclosed compounds represented by the following formulae (C) to (H), but there is no specific disclosure of the compounds of the present invention. In addition, there is no description that the compound has a PDE9-inhibitory action.

[Chem. 1]

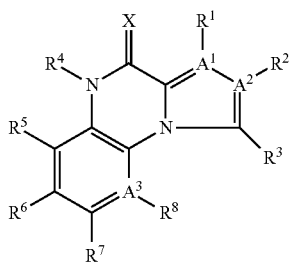

(A)

[Chem. 2]

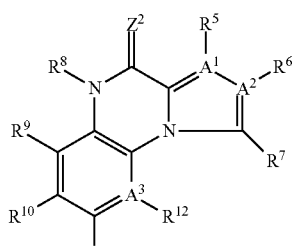

(B)

[Chem. 3]

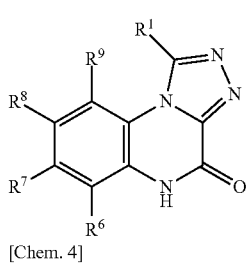

(C)

[Chem. 4]

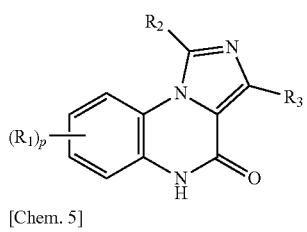

(D)

[Chem. 5]

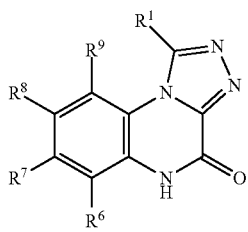

(E)

[Chem. 6]

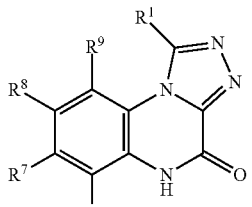

(F)

[Chem. 7]

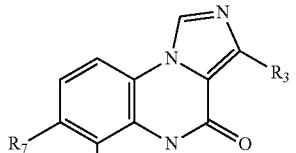

(G)

[Chem. 8]

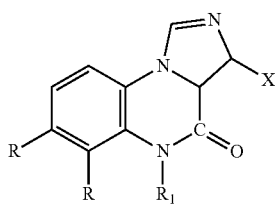

(H)

(For the symbols in the formulae, refer to each of the corresponding patent publications.)

RELATED ART

Patent Document

Patent Document 1: Pamphlet of International Publication WO 2008/072779
Patent Document 2: Pamphlet of International Publication WO 2008/072778
Patent Document 3: Pamphlet of International Publication WO 2006/135080
Patent Document 4: Pamphlet of International Publication WO 2008/018306
Patent Document 5: Pamphlet of International Publication WO 2010/026214
Patent Document 6: Pamphlet of International Publication WO 2010/084438
Patent Document 7: Pamphlet of International Publication WO 94/21639
Patent Document 8: Pamphlet of International Publication WO 99/09845
Patent Document 9: Pamphlet of International Publication WO 96/08492
Patent Document 10: Pamphlet of International Publication WO 96/08493
Patent Document 11: Pamphlet of International Publication WO 93/17025
Patent Document 12: Pamphlet of International Publication WO 93/12113

Non-Patent Document

Non-Patent Document 1: Thiyagarajan, M., Pharmacology, 65:pp. 119-128 (2002)
Non-Patent Document 2: Shah, P. J. R., et al., Br. J. Urol., 55:pp. 229-232 (1983)
Non-Patent Document 3: Finkbeiner, A. E., J. Urol., 134:pp. 443-449 (1985)
Non-Patent Document 4: Bloch, W., et al., Prostate, 33:pp. 1-8 (1997)
Non-Patent Document 5: Toprakqi, M., et al., Int. J. Clin. Lab. Res., 30:pp. 83-85 (2000)
Non-Patent Document 6: Fisher, D. A., et al., J. Biol. Chem., 273:pp. 15559-15564 (1998)
Non-Patent Document 7: Rentero, C., et al., Biochem. Biophys. Res. Commun., 301:pp. 686-692 (2003)

SUMMARY OF INVENTION

Problems to be Solved by the Invention

The present inventors aim to provide a compound which has a PDE9-inhibitory action and is useful as an active ingredient for a pharmaceutical composition for preventing and treating storage dysfunction, voiding dysfunction, and bladder/urethral diseases, and the like.

Means for Solving the Problems

The present inventors have extensively investigated a compound which has a PDE9-inhibitory action, and as a result, they have found that a compound of the formula (I) is useful as a compound having a PDE9-inhibitory action, thereby completing the present invention.

That is, the present invention relates to a compound of the formula (I) or a salt thereof, and a pharmaceutical composition including the compound of the formula (I) or a salt thereof, and an excipient.

[Chem. 9]

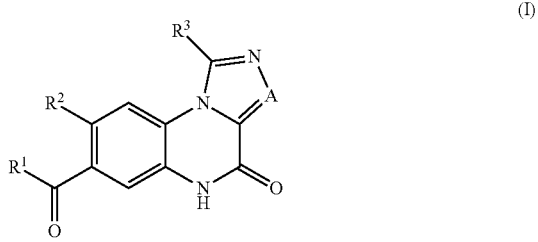

(I)

[wherein
A is N or CH,
$R^1$ is 2,3-dihydroindolyl, 1,3-dihydroisoindolyl or dihydropyrrolopyridyl, each of which may be substituted,
$R^2$ is halogen, or lower alkyl, —O-lower alkyl or cycloalkyl, each of which may be substituted,
$R^3$ is lower alkyl, cycloalkyl or a saturated heteroring, each of which may be substituted.]

Furthermore, unless specifically described otherwise, in the case where the symbols in any of the formulae in the present specification are also used in other formulae, the same symbols denote the same meanings.

Furthermore, the present invention relates to a pharmaceutical composition for preventing or treating storage dysfunction, voiding dysfunction, and bladder/urethral diseases, and the like, which includes a compound of the formula (I) or a salt thereof. Further, the pharmaceutical composition includes an agent for preventing or treating storage dysfunction, voiding dysfunction, and bladder/urethral diseases, and the like, which includes a compound of the formula (I) or a salt thereof.

The present invention further relates to use of the compound of the formula (I) or a salt thereof for the manufacture of a pharmaceutical composition for preventing or treating storage dysfunction, voiding dysfunction, and bladder/urethral diseases, and the like, use of the compound of the formula (I) or a salt thereof for preventing or treating storage dysfunction, voiding dysfunction, and bladder/urethral diseases, and the like, the compound of the formula (I) or a salt thereof for preventing or treating storage dysfunction, voiding dysfunction, and bladder/urethral diseases, and the like, and a method for preventing or treating storage dysfunction, voiding dysfunction, and bladder/urethral diseases, and the like, which includes administering to a subject an effective amount of the compound of the formula (I) or a salt thereof. Further, the "subject" is a human or another animal in need of such prevention or treatment, and in a certain embodiment, a human in need of such prevention or treatment.

In the present specification, the "storage dysfunction" refers to "storage function disorder (storage dysfunction)" with which urine cannot be held during storage, and the "voiding dysfunction" refers to "voiding function disorder (voiding dysfunction)" with which urine cannot be discharged sufficiently during voiding due to increased urethral resistance and decreased bladder contraction (Neurourol Urodynam, 21: pp. 167-178 (2002)).

As used in the present specification, the "bladder/urethral diseases" include "lower urinary tract dysfunction", and "lower urinary tract symptoms (LUTS)" (Neurourol Urodynam, 21: pp. 167-178 (2002)), which are symptoms derived from the lower urinary tract dysfunction. Accordingly, "bladder/urethral diseases" as used herein include "storage dysfunction" and "voiding dysfunction".

In the present invention, examples of the bladder/urethral diseases include, in a certain embodiment, underactive bladder, hypotonic bladder, acontractile bladder, detrusor underactivity, neurogenic bladder, urethra relaxation failure or detrusor-external urethral sphincter dyssynergia, overactive bladder, and lower urinary tract symptoms thereof, and benign prostatic hyperplasia, interstitial cystitis, chronic prostatitis, urethra calculus, and lower urinary tract symptoms accompanying them, and the like.

In another embodiment, examples of the bladder/urethral diseases include underactive bladder, hypotonic bladder, acontractile bladder, detrusor underactivity, neurogenic bladder, urethra relaxation failure or detrusor-external urethral sphincter dyssynergia, and lower urinary tract symptoms thereof, and benign prostatic hyperplasia, interstitial cystitis, chronic prostatitis, urethra calculus, and lower urinary tract symptoms accompanying them, and the like.

In a further embodiment, examples of the bladder/urethral diseases include underactive bladder, hypotonic bladder, acontractile bladder, detrusor underactivity, neurogenic bladder, urethra relaxation failure or detrusor-external urethral sphincter dyssynergia, and lower urinary tract symptoms thereof, benign prostatic hyperplasia and lower urinary tract symptoms accompanying them, and the like.

In a still further embodiment, examples of the bladder/urethral diseases include underactive bladder, hypotonic bladder, acontractile bladder, detrusor underactivity, urethra relaxation failure or detrusor-external urethral sphincter dyssynergia, lower urinary tract symptoms thereof, benign prostatic hyperplasia and lower urinary tract symptoms accompanying them, and the like.

In the present invention, specific examples of the storage dysfunction include overactive bladder, and overactive bladder symptoms such as urinary urgency, urinary frequency, urge incontinence, nocturia, and the like.

In the present invention, examples of the voiding dysfunction include voiding dysfunction due to an increase in urethral resistance and voiding dysfunction due to a decrease in the bladder contractile force. In a certain embodiment, specific examples thereof include voiding dysfunction in the underactive bladder, voiding dysfunction in the hypotonic bladder, voiding dysfunction in the acontractile bladder, voiding dysfunction in the neurogenic bladder, voiding dysfunction in the detrusor underactivity, voiding dysfunction in the urethra relaxation failure or detrusor-external urethral sphincter dyssynergia, voiding dysfunction accompanying benign prostatic hyperplasia, voiding dysfunction accompanying chronic prostatitis, voiding dysfunction accompanying urethra calculus, voiding dysfunction accompanying interstitial cystitis, voiding dysfunction accompanying detrusor underactivity, and the like.

In a further embodiment, examples of the voiding dysfunction include voiding dysfunction in the underactive bladder, voiding dysfunction in the hypotonic bladder, voiding dysfunction in the acontractile bladder, voiding dysfunction in the detrusor underactivity, voiding dysfunction in the urethra relaxation failure or detrusor-external urethral sphincter dyssynergia, voiding dysfunction accompanying benign prostatic hyperplasia, and the like.

Effect of the Invention

The compound of the formula (I) or a salt thereof has a PDE9-inhibitory action, and can be used as an agent for preventing and/or treating diseases related to degradation of cGMP by PDE9, for example, storage dysfunction, voiding dysfunction, and bladder/urethral diseases, in another embodiment, diseases such as underactive bladder, hypotonic bladder, acontractile bladder, detrusor underactivity, neurogenic bladder, urethra relaxation failure or detrusor-external urethral sphincter dyssynergia, overactive bladder, and lower urinary tract symptoms thereof, and benign prostatic hyperplasia, interstitial cystitis, chronic prostatitis, urethra calculus, and lower urinary tract symptoms accompanying them, and the like, and in a further embodiment, diseases such as underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, urethra calculus, and the like.

EMBODIMENTS FOR CARRYING OUT THE INVENTION

The "lower alkyl" is straight or branched chain alkyl having 1 to 6 carbon atoms (hereinafter simply referred to as $C_{1-6}$), for example, methyl, ethyl, n-propyl, isopropyl, n-butyl, isobutyl, sec-butyl, tert-butyl, n-pentyl, n-hexyl, or the like, and in another embodiment, $C_{1-4}$ alkyl, and in a further embodiment, methyl, ethyl, n-propyl, isopropyl, n-butyl, sec-butyl or tert-butyl.

The "halogen" means F, Cl, Br, or I.

The "halogeno-lower alkyl" is $C_{1-6}$ alkyl substituted with one or more halogen atoms, in another embodiment, lower alkyl substituted with 1 to 5 halogen atoms, and in a further embodiment, trifluoromethyl.

The "cycloalkyl" is a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like, in another embodiment, $C_{3-8}$ cycloalkyl, in a further embodiment, $C_{3-6}$ cycloalkyl, and in a still further embodiment, cyclopropyl, cyclobutyl or cyclopentyl.

The "hetero ring" means a ring group containing i) a monocyclic 3- to 8-membered, and in another embodiment, 5- to 7-membered hetero ring, containing 1 to 4 hetero atoms selected from oxygen, sulfur and nitrogen, and ii) a bi- to tricyclic hetero ring containing 1 to 5 hetero atoms selected from oxygen, sulfur and nitrogen, formed by ring fusion of the monocyclic hetero ring with one or two rings selected from the group consisting of a monocyclic hetero ring, a benzene ring, $C_{5-8}$ cycloalkane and $C_{5-8}$ cycloalkene, and it includes a spiro ring group. The ring atom, sulfur or nitrogen, may be oxidized to form an oxide or a dioxide.

Examples of the "hetero ring" include the following embodiments:

(1) Monocyclic saturated hetero rings (a) those containing 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, and the like;

(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;

(c) those containing 1 to 2 sulfur atoms, for example, tetrahydrothiopyranyl and the like;

(d) those containing 1 to 2 sulfur atoms and 1 to 2 oxygen atoms, for example, oxathiolanyl and the like; and (e) those containing 1 to 2 oxygen atoms, for example, oxiranyl, oxetanyl, dioxolanyl, tetrahydrofuranyl, tetrahydropyranyl, 1,4-dioxanyl, and the like;

(2) Fused polycyclic saturated hetero ring groups (a) those containing 1 to 5 nitrogen atoms, for example, quinuclidinyl, azabicyclo[2.2.1]heptyl, diazabicyclo[2.2.1]heptyl, azabicyclo[3.2.1]octyl, diazabicyclo[3.2.1]octyl, diazabicyclo[3.3.1]nonyl, and the like;

(b) those containing 1 to 4 nitrogen atoms and 1 to 3 sulfur atoms and/or 1 to 3 oxygen atoms, for example, trithiadiazaindenyl, dioxoloimidazolidinyl, 2-oxa-5-azabicyclo[2.2.1]heptyl, and the like;

(c) those containing 1 to 3 sulfur atoms and/or 1 to 3 oxygen atoms, for example, 2,6-dioxabicyclo[3.2.2]oct-7-yl and the like.

The "saturated hetero ring" means a group described in (1) Monocyclic saturated hetero rings and (2) Fused polycyclic saturated hetero ring groups of the "hetero ring" above. The ring atom, sulfur or nitrogen, may be oxidized to form an oxide or a dioxide. In another embodiment, the saturated hetero ring is a monocyclic saturated hetero ring.

The "oxygen-containing saturated hetero ring" refers to a saturated hetero ring containing at least one oxygen atom among the groups described in (1)(b), (1)(d), (1)(e), or the like of the "hetero ring" above. In another embodiment, it is a monocyclic saturated hetero ring containing 1 to 2 oxygen atoms, for example, oxiranyl, oxetanyl, dioxolanyl, tetrahydrofuranyl, tetrahydropyranyl, 1,4-dioxanyl, and the like.

Examples of the "saturated hetero ring" in $R^3$ are oxygen-containing saturated hetero rings, in another embodiment, tetrahydrofuranyl or tetrahydropyranyl, in a further embodiment, tetrahydro-2H-pyran-3-yl or tetrahydro-2H-pyran-4-yl, and in a still further embodiment, tetrahydrofuran-3-yl.

In the present specification, the expression "which may be substituted" represents "which is not substituted" or "which is substituted with 1 to 5 substituents". Further, if it has a plurality of substituents, the substituents may be the same as or different from each other.

Examples of the substituent for "lower alkyl, —O-lower alkyl or cycloalkyl, each of which may be substituted" in $R^2$ include pyrrolidinyl which may be substituted with —O-lower alkyl, —N(lower alkyl)$_2$, tetrahydrofuranyl, and lower alkyl. The substituent for the "lower alkyl which may be substituted" is, in another embodiment, —O-lower alkyl. The substituent for the "—O-lower alkyl which may be substituted" is, in another embodiment, tetrahydrofuranyl.

Examples of the substituent for the "lower alkyl, cycloalkyl or saturated hetero ring, each of which may be substituted" in $R^3$ include halogen, lower alkyl, cycloalkyl, —OH, oxo (=O), and —O-lower alkyl. Examples of the substituent for the "lower alkyl which may be substituted" include, in another embodiment, cycloalkyl. Examples of the substituent for the "cycloalkyl which may be substituted" include, in another embodiment, halogen, lower alkyl, —OH, oxo(=O), and —O-lower alkyl, and in a further embodiment, —OH and —O-lower alkyl. Examples of the substituent for the "saturated hetero ring which may be substituted" include, in another embodiment, halogen, lower alkyl and —O-lower alkyl.

Examples of the substituent for the "2,3-dihydroindolyl, 1,3-dihydroisoindolyl or dihydropyrrolopyridyl, each of which may be substituted" in $R^1$ include halogen; —O-lower alkyl; cyano; halogeno-lower alkyl; cycloalkyl; or lower alkyl which may be substituted with —O-lower alkyl, —NH(lower alkyl), —N(lower alkyl)$_2$, or a monocyclic saturated hetero ring, in another embodiment, lower alkyl which may be substituted with halogen, —O-lower alkyl or —N(lower alkyl)$_2$, —O-lower alkyl, cycloalkyl or halogeno-lower alkyl (here, the monocyclic saturated hetero ring may be substituted with halogen or —O-lower alkyl). In another embodiment, it is halogen, —O-lower alkyl, lower alkyl or halogeno-lower alkyl.

Embodiments of the compound of the formula (I) or a salt thereof are presented below.

(1) The compound or a salt thereof, wherein A is CH;

and in another embodiment, the compound or a salt thereof, wherein A is N.

(2)

(2-1) The compound or a salt thereof, wherein $R^1$ is 2,3-dihydro-1H-indol-1-yl which may be substituted;

in another embodiment, the compound or a salt thereof, wherein $R^1$ is 2,3-dihydro-1H-indol-1-yl substituted with at least one group selected from the group consisting of halogen, lower alkyl which may be substituted with —O-lower alkyl, and halogeno-lower alkyl;

in a further embodiment, the compound or a salt thereof, wherein $R^1$ is 2,3-dihydro-1H-indol-1-yl substituted with two fluorine atoms;

in a still further embodiment, the compound or a salt thereof, wherein $R^1$ is 2,3-dihydro-1H-indol-1-yl substituted with one or two substituents selected from the group consisting of chloro, trifluoromethyl, methyl and methoxymethyl; and in a still further embodiment, the compound or a salt thereof, wherein $R^1$ is 5-chloro-2,3-dihydro-1H-indol-1-yl, 5-chloro-3-methyl-2,3-dihydro-1H-indol-1-yl, 5-chloro-3-(methoxymethyl)-2,3-dihydro-1H-indol-1-yl, 5-chloro-2-methyl-2,3-dihydro-1H-indol-1-yl, 5-chloro-2-(methoxymethyl)-2,3-dihydro-1H-indol-1-yl, 5-fluoro-2,3-dihydro-1H-indol-1-yl, 5,6-difluoro-2,3-dihydro-1H-indol-1-yl, 5-bromo-2,3-dihydro-1H-indol-1-yl, or 5-(trifluoromethyl)-2,3-dihydro-1H-indol-1-yl.

(2-2) The compound or a salt thereof, wherein $R^1$ is 1,3-dihydro-2H-isoindol-2-yl which may be substituted;

in another embodiment, the compound or a salt thereof, wherein $R^1$ is 1,3-dihydro-2H-isoindol-2-yl substituted with at least one group selected from the group consisting of halogen, lower alkyl substituted with —O-lower alkyl, and lower alkyl substituted with —N(lower alkyl)$_2$;

in a further embodiment, the compound or a salt thereof, wherein $R^1$ is 1,3-dihydro-2H-isoindol-2-yl substituted with one or two fluorine atoms; and in a still further embodiment, the compound or a salt thereof, wherein $R^1$ is 4,7-difluoro-1,3-dihydro-2H-isoindol-2-yl, 4-fluoro-1,3-dihydro-2H-isoindol-2-yl, or 1,3-dihydro-2H-isoindol-2-yl substituted with dimethylaminomethyl or methoxymethyl at the 4-position.

(2-3) The compound or a salt thereof, wherein $R^1$ is 2,3-dihydro-1H-pyrrolo[2,3-b]pyridin-1-yl which may be substituted;

in another embodiment, the compound or a salt thereof, wherein $R^1$ is 2,3-dihydro-1H-pyrrolo[2,3-b]pyridin-1-yl substituted with at least one group selected from the group consisting of halogen, lower alkyl, halogeno-lower alkyl, cycloalkyl and —O-lower alkyl;

in a further embodiment, the compound or a salt thereof, wherein $R^1$ is 2,3-dihydro-1H-pyrrolo[2,3-b]pyridin-1-yl substituted with at least one group selected from the group consisting of halogen, lower alkyl, halogeno-lower alkyl and —O-lower alkyl;

in a still further embodiment, the compound or a salt thereof, wherein $R^1$ is 2,3-dihydro-1H-pyrrolo[2,3-b]pyridin-1-yl substituted with a substituent selected from the group consisting of bromo, methyl and ethyl at the 5-position; and in a still further embodiment, the compound or a salt thereof, wherein $R^1$ is 5-fluoro-2,3-dihydro-1H-pyrrolo[2,3-b]pyridin-1-yl, 5-bromo-2,3-dihydro-1H-pyrrolo[2,3-b]pyridin-1-yl, 5-methyl-2,3-dihydro-1H-pyrrolo[2,3-b]pyridin-1-yl, 5-ethyl-2,3-dihydro-1H-pyrrolo[2,3-b]pyridin-1-yl, 5-(trifluoromethyl)-2,3-dihydro-1H-pyrrolo[2,3-b]pyridin-1-yl, 5-methoxy-2,3-dihydro-1H-pyrrolo[2,3-b]pyridin-1-yl, 5-cyclopropyl-2,3-dihydro-1H-pyrrolo[2,3-b]pyridin-1-yl, or 5-bromo-3,3-dimethyl-2,3-dihydro-1H-pyrrolo[2,3-b]pyridin-1-yl.

(2-4) The compound or a salt thereof, wherein $R^1$ is 2,3-dihydro-1H-pyrrolo[2,3-c]pyridin-1-yl which may be substituted;

in another embodiment, the compound or a salt thereof, wherein $R^1$ is 2,3-dihydro-1H-pyrrolo[2,3-c]pyridin-1-yl substituted with —O-lower alkyl; and in a further embodiment, the compound or a salt thereof, wherein $R^1$ is 5-methoxy-2,3-dihydro-1H-pyrrolo[2,3-c]pyridin-1-yl.

(3)

(3-1) The compound or a salt thereof, wherein $R^2$ is halogen; and in another embodiment, the compound or a salt thereof, wherein $R^2$ is fluoro or chloro.

(3-2) The compound or a salt thereof, wherein $R^2$ is lower alkyl which may be substituted;

in another embodiment, the compound or a salt thereof, wherein $R^2$ is lower alkyl which may be substituted with —O-lower alkyl;

in a further embodiment, the compound or a salt thereof, wherein $R^2$ is methyl, ethyl or methoxymethyl;

in a still further embodiment, the compound or a salt thereof, wherein $R^2$ is methyl or methoxymethyl;

in a still further embodiment, the compound or a salt thereof, wherein $R^2$ is methyl; and in a still further embodiment, the compound or a salt thereof, wherein $R^2$ is methoxymethyl.

(3-3) The compound or a salt thereof, wherein $R^2$ is —O-lower alkyl which may be substituted;

in another embodiment, the compound or a salt thereof, wherein $R^2$ is —O-lower alkyl which may be substituted with tetrahydrofuranyl;

in a further embodiment, the compound or a salt thereof, wherein $R^2$ is tetrahydrofuran-3-ylmethoxy; and in a still further embodiment, the compound or a salt thereof, wherein $R^2$ is methoxy.

(3-4) The compound or a salt thereof, wherein $R^2$ is cycloalkyl which may be substituted; and in another embodiment, the compound or a salt thereof, wherein $R^2$ is cyclopropyl.

(4)

(4-1) The compound or a salt thereof, wherein $R^3$ is lower alkyl which may be substituted; and in another embodiment, the compound or a salt thereof, wherein $R^3$ is lower alkyl substituted with cyclopropyl.

(4-2) The compound or a salt thereof, wherein $R^3$ is cycloalkyl which may be substituted; and in another embodiment, the compound or a salt thereof, wherein $R^3$ is cyclobutyl which may be substituted with methoxy, and in another embodiment, $R^3$ is cyclopentyl substituted with —OH.

(4-3) The compound or a salt thereof, wherein $R^3$ is a saturated hetero ring which may be substituted;

in another embodiment, the compound or a salt thereof, wherein $R^3$ is tetrahydrofuran-3-yl, tetrahydro-2H-pyran-3-yl, or tetrahydro-2H-pyran-4-yl;

in a further embodiment, the compound or a salt thereof, wherein $R^3$ is tetrahydrofuran-3-yl or tetrahydro-2H-pyran-4-yl; and in a still further embodiment, the compound or a salt thereof, wherein $R^3$ is tetrahydrofuran-3-yl.

(5) The compound which is a combination of two or more of the groups in (1) to (4) above.

The compounds of the formula (I) or salts thereof include a compound or a salt thereof, which is a combination of two or more groups of the groups described in (1) to (4) above as described in (5), as well as the following embodiments including specific examples of the group.

(6) The compound or a salt thereof, wherein

A is CH, $R^1$ is 2,3-dihydro-1H-pyrrolo[2,3-b]pyridin-1-yl substituted with fluoro, bromo, methyl, ethyl, trifluoromethyl or methoxy at the 5-position, or 5-methoxy-2,3-dihydro-1H-pyrrolo[2,3-c]pyridin-1-yl, $R^2$ is methyl or methoxymethyl, and $R^3$ is tetrahydrofuran-3-yl.

(7) The compound or a salt thereof, wherein

A is CH, $R^1$ is 2,3-dihydro-1H-pyrrolo[2,3-b]pyridin-1-yl substituted with fluoro, bromo, methyl, ethyl, trifluoromethyl or methoxy at the 5-position, $R^2$ is methyl or methoxymethyl, and $R^3$ is tetrahydrofuran-3-yl.

(8) The compound or a salt thereof, wherein

A is CH, $R^1$ is 5-methoxy-2,3-dihydro-1H-pyrrolo[2,3-c]pyridin-1-yl, $R^2$ is methyl or methoxymethyl, and $R^3$ is tetrahydrofuran-3-yl.

(9) The compound or a salt thereof, wherein

A is CH, $R^1$ is 2,3-dihydro-1H-pyrrolo[2,3-b]pyridin-1-yl substituted with fluoro, bromo or methyl at the 5-position, or 5-methoxy-2,3-dihydro-1H-pyrrolo[2,3-c]pyridin-1-yl, $R^2$ is fluoro, chloro, cyclopropyl, methoxy, methoxymethyl or tetrahydrofuran-3-ylmethoxy, and $R^3$ is tetrahydro-2H-pyran-4-yl, (provided that when $R^1$ is 5-bromo-2,3-dihydro-1H-pyrrolo[2,3-b]pyridin-1-yl, $R^2$ is fluoro, chloro, methoxy or tetrahydrofuran-3-ylmethoxy, when $R^1$ is 5-methyl-2,3-dihydro-1H-pyrrolo[2,3-b]pyridin-1-yl, $R^2$ is fluoro, cyclopropyl or methoxymethyl, and when $R^1$ is 5-methoxy-2,3-dihydro-1H-pyrrolo[2,3-c]pyridin-1-yl, $R^2$ is fluoro or chloro).

(10) The compound or a salt thereof, wherein

A is CH, $R^1$ is 2,3-dihydro-1H-pyrrolo[2,3-b]pyridin-1-yl substituted with fluoro, bromo or methyl at the 5-position, $R^2$ is fluoro, chloro, cyclopropyl, methoxy, methoxymethyl or tetrahydrofuran-3-ylmethoxy, and $R^3$ is tetrahydro-2H-pyran-4-yl, (provided that when $R^1$ is 5-bromo-2,3-dihydro-1H-pyrrolo[2,3-b]pyridin-1-yl, $R^2$ is fluoro, chloro, methoxy or tetrahydrofuran-3-ylmethoxy, and when $R^1$ is 5-methyl-2,3-dihydro-1H-pyrrolo[2,3-b]pyridin-1-yl, $R^2$ is fluoro, cyclopropyl or methoxymethyl).

(11) The compound or a salt thereof, wherein

A is CH, $R^1$ is 5-methoxy-2,3-dihydro-1H-pyrrolo[2,3-c]pyridin-1-yl, $R^2$ is fluoro or chloro, and $R^3$ is tetrahydro-2H-pyran-4-yl.

(12) The compound or a salt thereof, wherein

A is CH, $R^1$ is 2,3-dihydro-1H-pyrrolo[2,3-b]pyridin-1-yl substituted with fluoro, bromo, methyl or methoxy at the 5-position, or 5-methoxy-2,3-dihydro-1H-pyrrolo[2,3-c]pyridin-1-yl, $R^2$ is methyl, and $R^3$ is tetrahydro-2H-pyran-3-yl.

(13) The compound or a salt thereof, wherein

A is CH, $R^1$ is 2,3-dihydro-1H-pyrrolo[2,3-b]pyridin-1-yl substituted with fluoro, bromo, methyl or methoxy at the 5-position, $R^2$ is methyl, and $R^3$ is tetrahydro-2H-pyran-3-yl.

(14) The compound or a salt thereof, wherein

A is CH, $R^1$ is 5-methoxy-2,3-dihydro-1H-pyrrolo[2,3-c]pyridin-1-yl, $R^2$ is methyl, and $R^3$ is tetrahydro-2H-pyran-3-yl.

(15) The compound or a salt thereof, wherein

A is CH, $R^1$ is 5-chloro-2,3-dihydro-1H-indol-1-yl, 5,6-difluoro-2,3-dihydro-1H-indol-1-yl, 4,7-difluoro-1,3-dihydro-2H-isoindol-2-yl or 4-fluoro-1,3-dihydro-2H-isoindol-2-yl, R² is methyl or methoxymethyl, and
R³ is tetrahydrofuran-3-yl,
(provided that when R¹ is 5-chloro-2,3-dihydro-1H-indol-1-yl, R² is methoxymethyl).

(16) The compound or a salt thereof, wherein
A is CH,
R¹ is 5-chloro-2,3-dihydro-1H-indol-1-yl substituted with methyl or methoxymethyl at the 3-position,
R² is fluoro or methyl, and
R³ is tetrahydro-2H-pyran-4-yl,
(provided that when R¹ is 5-chloro-2,3-dihydro-1H-indol-1-yl, R² is fluoro).

(17) The compound or a salt thereof, wherein
A is N,
R¹ is 2,3-dihydro-1H-indol-1-yl substituted with bromo or trifluoromethyl at the 5-position, 5-chloro-2,3-dihydro-1H-indol-1-yl which may be substituted with methyl or methoxymethyl at the 2-position, 5-chloro-3-methyl-2,3-dihydro-1H-indol-1-yl, 4,7-difluoro-1,3-dihydro-2H-isoindol-2-yl, 2,3-dihydro-1H-pyrrolo[2,3-b]pyridin-1-yl substituted with trifluoromethyl or cyclopropyl at the 5-position, or 5-bromo-3,3-dimethyl-2,3-dihydro-1H-pyrrolo[2,3-b]pyridin-1-yl,
R² is methyl, cyclopropyl or methoxymethyl, and
R³ is tetrahydro-2H-pyran-4-yl,
(provided that when R¹ is 5-chloro-2,3-dihydro-1H-indol-1-yl, R² is cyclopropyl, and when R¹ is 5-cyclopropyl-2,3-dihydro-1H-pyrrolo[2,3-b]pyridin-1-yl, R² is methoxymethyl).

(18) The compound or a salt thereof, wherein
A is N,
R¹ is 2,3-dihydro-1H-indol-1-yl substituted with fluoro, chloro, bromo or trifluoromethyl at the 5-position, 5-chloro-2-(methoxymethyl)-2,3-dihydro-1H-indol-1-yl, 4,7-difluoro-1,3-dihydro-2H-isoindol-2-yl, or 2,3-dihydro-1H-pyrrolo[2,3-b]pyridin-1-yl substituted with bromo, methyl, ethyl, cyclopropyl or trifluoromethyl at the 5-position,
R² is methyl, ethyl or methoxymethyl, and
R³ is cyclopropylmethyl,
(provided that when R¹ is 5-chloro-2,3-dihydro-1H-indol-1-yl, R² is ethyl).

(19) The compound or a salt thereof, wherein
A is N,
R¹ is 2,3-dihydro-1H-indol-1-yl substituted with fluoro, chloro, bromo or trifluoromethyl at the 5-position, 5-chloro-2,3-dihydro-1H-indol-1-yl substituted with methyl or methoxymethyl at the 2-position, or 5-chloro-3-(methoxymethyl)-2,3-dihydro-1H-indol-1-yl, 4,7-difluoro-1,3-dihydro-2H-isoindol-2-yl, or 2,3-dihydro-1H-pyrrolo[2,3-b]pyridin-1-yl substituted with bromo or trifluoromethyl at the 5-position,
R² is methyl, ethyl or methoxymethyl,
R³ is cyclobutyl which may be substituted with methoxy at the 3-position,
(provided that when R³ is cyclobutyl, R¹ is 2,3-dihydro-1H-indol-1-yl substituted with fluoro or chloro at the 5-position, or 2,3-dihydro-1H-pyrrolo[2,3-b]pyridin-1-yl substituted with bromo at the 5-position, R² is ethyl or methoxymethyl).

(20) The compound or a salt thereof, wherein
A is CH,
R¹ is 5-chloro-2,3-dihydro-1H-indol-1-yl, or 5-fluoro-2,3-dihydro-1H-indol-1-yl which may be substituted with fluoro at the 6-position, 4,7-difluoro-1,3-dihydro-2H-isoindol-2-yl, or 5-bromo-2,3-dihydro-1H-pyrrolo[2,3-b]pyridin-1-yl, R² is methyl, and
R³ is 2-hydroxycyclopentyl,
(provided that 7-[(5-chloro-2,3-dihydro-1H-indol-1-yl)carbonyl]-1-(cis-2-hydroxycyclopentyl)-8-methylimidazo[1,5-a]quinoxalin-4(5H)-one is excluded).

(21) The compound or a salt thereof, wherein
A is N or CH,
R¹ is 2,3-dihydro-1H-indol-1-yl substituted with chloro, bromo or trifluoromethyl at the 5-position, 2,3-dihydro-1H-pyrrolo[2,3-b]pyridin-1-yl substituted with bromo or methyl at the 5-position, or 5-methoxy-2,3-dihydro-1H-pyrrolo[2,3-c]pyridin-1-yl,
R² is methyl, and
R³ is 3-methoxycyclobutyl.

(22) The compound or a salt thereof, wherein
A is CH,
R¹ is 2,3-dihydro-1H-pyrrolo[2,3-b]pyridin-1-yl substituted with ethyl, trifluoromethyl, cyclopropyl or methoxy at the 5-position,
R² is methyl, and
R³ is tetrahydro-2H-pyran-4-yl.

(23) The compound or a salt thereof, wherein
A is CH,
R¹ is 2,3-dihydro-1H-pyrrolo[2,3-b]pyridin-1-yl substituted with fluoro, bromo or methyl at the 5-position,
R² is fluoro, cyclopropyl, methoxy or methoxymethyl, and
R³ is tetrahydro-2H-pyran-4-yl,
(provided that when R¹ is 5-bromo-2,3-dihydro-1H-pyrrolo[2,3-b]pyridin-1-yl, R² is fluoro or methoxy, and when R¹ is 5-methyl-2,3-dihydro-1H-pyrrolo[2,3-b]pyridin-1-yl, R² is fluoro, cyclopropyl or methoxymethyl).

(24) The compound or a salt thereof, wherein
A is CH,
R¹ is 5-methoxy-2,3-dihydro-1H-pyrrolo[2,3-c]pyridin-1-yl,
R² is fluoro or chloro, and
R³ is tetrahydro-2H-pyran-4-yl.

(25) The compound or a salt thereof, wherein
A is CH,
R¹ is 5-fluoro-2,3-dihydro-1H-indol-1-yl or 5-bromo-2,3-dihydro-1H-pyrrolo[2,3-b]pyridin-1-yl,
R² is tetrahydrofuran-3-ylmethoxy, and
R³ is tetrahydro-2H-pyran-4-yl.

(26) The compound or a salt thereof, wherein
A is CH,
R¹ is 1,3-dihydro-2H-isoindol-2-yl substituted with dimethylaminomethyl or methoxymethyl at the 4-position, or 4,7-difluoro-1,3-dihydro-2H-isoindol-2-yl,
R² is methyl, fluoro, chloro or methoxy, and
R³ is tetrahydro-2H-pyran-4-yl,
(provided that when R¹ is 4,7-difluoro-1,3-dihydro-2H-isoindol-2-yl, R² is fluoro, chloro or methoxy).

Examples of the specific compounds included in the compound of the formula (I) or a salt thereof include the following compounds:

1-(cyclopropylmethyl)-7-[(5-ethyl-2,3-dihydro-1H-pyrrolo[2,3-b]pyridin-1-yl)carbonyl]-8-methyl[1,2,4]triazolo[4,3-a]quinoxalin-4(5H)-one, 7-[(5-chloro-2-methyl-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-[(5-chloro-2,3-dihydro-1H-indol-1-yl)carbonyl]-1-(3-methoxycyclobutyl)-8-methyl[1,2,4]triazolo[4,3-a]quinoxalin-4(5H)-one, 7-{[5-chloro-2-(methoxymethyl)-2,3-dihydro-1H-indol-1-yl]carbonyl}-8-methyl-1-(tetrahydro-2H-pyran-4-yl)[1,2,4]triazolo[4,3-a]quinoxalin-4(5H)-one, 7-[(5-bromo-2,3-dihydro-1H-indol-1-yl)carbonyl]-1-(3-methoxycyclobutyl)-8-methyl[1,2,4]triazolo[4,3-a]quinoxalin-4(5H)-one, 7-[(5-chloro-2,3-dihydro-1H-indol-1-yl)carbonyl]-1-(cyclopropylmethyl)-8-ethyl[1,2,4]triazolo[4,3-a]quinoxalin-4(5H)-one, 1-(cyclopropylmethyl)-8-ethyl-7-[(5-fluoro-2,3-dihydro-1H-indol-1-yl)carbonyl][1,2,4]triazolo[4,3-a]quinoxalin-4(5H)-one, 7-[(5-bromo-2,3-dihydro-1H-pyrrolo[2,3-b]pyridin-1-yl)carbonyl]-1-(cyclopropylmethyl)-8-ethyl[1,2,4]triazolo[4,3-a]quinoxalin-4(5H)-one, 1-(3-methoxycyclobutyl)-8-methyl-7-{[5-(trifluoromethyl)-2,3-dihydro-1H-indol-1-yl]carbonyl}[1,2,4]triazolo[4,3-a]quinoxalin-4(5H)-one, 8-methyl-1-(tetrahydro-2H-pyran-4-yl)-7-{[5-(trifluoromethyl)-2,3-dihydro-1H-indol-1-yl]carbonyl}[1,2,4]triazolo[4,3-a]quinoxalin-4(5H)-one, 7-[(5-bromo-2,3-dihydro-1H-pyrrolo[2,3-b]pyridin-1-yl)carbonyl]-1-(cyclopropylmethyl)-8-methyl[1,2,4]triazolo[4,3-a]quinoxalin-4(5H)-one, 7-[(5-chloro-2,3-dihydro-1H-indol-1-yl)carbonyl]-1-cyclobutyl-8-ethyl[1,2,4]triazolo[4,3-a]quinoxalin-4(5H)-one, 1-cyclobutyl-8-ethyl-7-[(5-fluoro-2,3-dihydro-1H-indol-1-yl)carbonyl][1,2,4]triazolo[4,3-a]quinoxalin-4(5H)-one, 7-[(5-bromo-2,3-dihydro-1H-pyrrolo[2,3-b]pyridin-1-yl)carbonyl]-1-cyclobutyl-8-ethyl[1,2,4]triazolo[4,3-a]quinoxalin-4(5H)-one, 7-[(5-chloro-2,3-dihydro-1H-indol-1-yl)carbonyl]-1-cyclobutyl-8-(methoxymethyl)[1,2,4]triazolo[4,3-a]quinoxalin-4(5H)-one, 7-[(5-bromo-2,3-dihydro-1H-indol-1-yl)carbonyl]-1-cyclobutyl-8-(methoxymethyl)[1,2,4]triazolo[4,3-a]quinoxalin-4(5H)-one, 7-[(5-bromo-2,3-dihydro-1H-pyrrolo[2,3-b]pyridin-1-yl)carbonyl]-1-cyclobutyl-8-(methoxymethyl)[1,2,4]triazolo[4,3-a]quinoxalin-4(5H)-one, 7-[(5-bromo-2,3-dihydro-1H-indol-1-yl)carbonyl]-1-(cyclopropylmethyl)-8-(methoxymethyl)[1,2,4]triazolo[4,3-a]quinoxalin-4(5H)-one, 7-[(5-bromo-2,3-dihydro-1H-pyrrolo[2,3-b]pyridin-1-yl)carbonyl]-1-(cyclopropylmethyl)-8-(methoxymethyl)[1,2,4]triazolo[4,3-a]quinoxalin-4(5H)-one, 7-[(5-chloro-2-methyl-2,3-dihydro-1H-indol-1-yl)carbonyl]-1-(3-methoxycyclobutyl)-8-methyl[1,2,4]triazolo[4,3-a]quinoxalin-4(5H)-one, 7-{[5-chloro-2-(methoxymethyl)-2,3-dihydro-1H-indol-1-yl]carbonyl}-1-cyclobutyl-8-methyl[1,2,4]triazolo[4,3-a]quinoxalin-4(5H)-one, 7-{[5-chloro-2-(methoxymethyl)-2,3-dihydro-1H-indol-1-yl]carbonyl}-1-(cyclopropylmethyl)-8-methyl[1,2,4]triazolo[4,3-a]quinoxalin-4(5H)-one, 1-(3-methoxycyclobutyl)-8-methyl-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 8-methyl-1-(tetrahydro-2H-pyran-4-yl)-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 1-cyclobutyl-8-methyl-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 1-(cyclopropylmethyl)-8-methyl-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 1-(cyclopropylmethyl)-8-methyl-7-[(5-methyl-2,3-dihydro-1H-pyrrolo[2,3-b]pyridin-1-yl)carbonyl][1,2,4]triazolo[4,3-a]quinoxalin-4(5H)-one, 7-[(5-bromo-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-[(5-cyclopropyl-2,3-dihydro-1H-pyrrolo[2,3-b]pyridin-1-yl)carbonyl]-8-(methoxymethyl)-1-(tetrahydro-2H-pyran-4-yl)[1,2,4]triazolo[4,3-a]quinoxalin-4(5H)-one, 7-[(5-chloro-2,3-dihydro-1H-indol-1-yl)carbonyl]-8-cyclopropyl-1-(tetrahydro-2H-pyran-4-yl)[1,2,4]triazolo[4,3-a]quinoxalin-4(5H)-one, 7-[(5-cyclopropyl-2,3-dihydro-1H-pyrrolo[2,3-b]pyridin-1-yl)carbonyl]-1-(cyclopropylmethyl)-8-methyl[1,2,4]triazolo[4,3-a]quinoxalin-4(5H)-one, 7-[(4,7-difluoro-1,3-dihydro-2H-isoindol-2-yl)carbonyl]-8-methyl-1-(tetrahydro-2H-pyran-4-yl)[1,2,4]triazolo[4,3-a]quinoxalin-4(5H)-one, 1-cyclobutyl-7-[(4,7-difluoro-1,3-dihydro-2H-isoindol-2-yl)carbonyl]-8-methyl[1,2,4]triazolo[4,3-a]quinoxalin-4(5H)-one, 1-(cyclopropylmethyl)-7-[(4,7-difluoro-1,3-dihydro-2H-isoindol-2-yl)carbonyl]-8-methyl[1,2,4]triazolo[4,3-a]quinoxalin-4(5H)-one, 1-cyclobutyl-8-(methoxymethyl)-7-{[5-(trifluoromethyl)-2,3-dihydro-1H-indol-1-yl]carbonyl}[1,2,4]triazolo[4,3-a]quinoxalin-4(5H)-one, 1-(cyclopropylmethyl)-8-(methoxymethyl)-7-{[5-(trifluoromethyl)-2,3-dihydro-1H-indol-1-yl]carbonyl}[1,2,4]triazolo[4,3-a]quinoxalin-4(5H)-one, 7-{[5-chloro-3-(methoxymethyl)-2,3-dihydro-1H-indol-1-yl]carbonyl}-1-cyclobutyl-8-methyl[1,2,4]triazolo[4,3-a]quinoxalin-4(5H)-one, 7-[(5-chloro-3-methyl-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-[(5-bromo-3,3-dimethyl-2,3-dihydro-1H-pyrrolo[2,3-b]pyridin-1-yl)carbonyl]-8-methyl-1-(tetrahydro-2H-pyran-4-yl)[1,2,4]triazolo[4,3-a]quinoxalin-4(5H)-one, 7-[(5-bromo-2,3-dihydro-1H-pyrrolo[2,3-b]pyridin-1-yl)carbonyl]-1-(3-methoxycyclobutyl)-8-methyl[1,2,4]triazolo[4,3-a]quinoxalin-4(5H)-one, 1-cyclobutyl-7-[(4,7-difluoro-1,3-dihydro-2H-isoindol-2-yl)carbonyl]-8-ethyl[1,2,4]triazolo[4,3-a]quinoxalin-4(5H)-one, and salts thereof, and isolated optical isomers thereof.

In another embodiment, examples of the specific compounds included in the compound of the formula (I) or a salt thereof include the following compounds:

7-[(5-bromo-2,3-dihydro-1H-pyrrolo[2,3-b]pyridin-1-yl)carbonyl]-8-(tetrahydrofuran-3-ylmethoxy)-1-(tetrahydro-2H-pyran-4-yl)imidazo[1,5-a]quinoxalin-4(5H)-one, 8-fluoro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, 7-[(5-methoxy-2,3-dihydro-1H-pyrrolo[2,3-c]pyridin-1-yl)carbonyl]-8-methyl-1-(tetrahydro-2H-pyran-3-yl)imidazo[1,5-a]quinoxalin-4(5H)-one, 7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one, 7-[(5-bromo-2,3-dihydro-1H-pyrrolo[2,3-b]pyridin-1-yl)carbonyl]-1-(cis-2-hydroxycyclopentyl)-8-methylimidazo[1,5-a]quinoxalin-4(5H)-one, 7-[(5-fluoro-2,3-dihydro-1H-indol-1-yl)carbonyl]-8-(tetrahydrofuran-3-ylmethoxy)-1-(tetrahydro-2H-pyran-4-yl)imidazo[1,5-a]quinoxalin-4(5H)-one, 7-({4-[(dimethylamino)methyl]-1,3-dihydro-2H-isoindol-2-yl}carbonyl)-8-methyl-1-(tetrahydro-2H-pyran-4-yl)imidazo[1,5-a]quinoxalin-4(5H)-one, 7-[(5-chloro-2,3-dihydro-1H-indol-1-yl)carbonyl]-8-fluoro-1-(tetrahydro-2H-pyran-4-yl)imidazo[1,5-a]quinoxalin-4(5H)-one, 7-[(5-ethyl-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, 7-{[4-(methoxymethyl)-1,3-dihydro-2H-isoindol-2-yl]carbonyl}-8-methyl-1-(tetrahydro-2H-pyran-4-yl)imidazo[1,5-a]quinoxalin-4(5H)-one, 8-chloro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, 7-[(5-fluoro-2,3-dihydro-1H-indol-1-yl)carbonyl]-1-(cis-2-hydroxycyclopentyl)-8-methylimidazo[1,5-a]quinoxalin-4(5H)-one, 7-[(5-bromo-2,3-dihydro-1H-pyrrolo[2,3-b]pyridin-1-yl)carbonyl]-8-methoxy-1-(tetrahydro-2H-pyran-4-yl)imidazo[1,5-a]quinoxalin-4(5H)-one, 8-(methoxymethyl)-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one, 8-methyl-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one, 7-[(5-methoxy-2,3-dihydro-1H-pyrrolo[2,3-c]pyridin-1-yl)carbonyl]-8-methyl-1-(tetrahydrofuran-3-yl)imidazo[1,5-a]quinoxalin-4(5H)-one, 7-[(5-ethyl-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 7-[(5,6-difluoro-2,3-dihydro-1H-indol-1-yl)carbonyl]-8-methyl-1-(tetrahydrofuran-3-yl)imidazo[1,5-a]quinoxalin-4(5H)-one, 7-[(5-bromo-2,3-dihydro-1H-pyrrolo[2,3-b]pyridin-1-yl)carbonyl]-8-fluoro-1-(tetrahydro-2H-pyran-4-yl)imidazo[1,5-a]quinoxalin-4(5H)-one, 8-fluoro-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-fluoro-7-[(5-fluoro-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 7-[(5,6-difluoro-2,3-dihydro-1H-indol-1-yl)carbonyl]-1-(cis-2-hydroxycyclopentyl)-8-methylimidazo[1,5-a]quinoxalin-4(5H)-one, 7-[(5,6-difluoro-2,3-dihydro-1H-indol-1-yl)carbonyl]-1-(trans-2-hydroxycyclopentyl)-8-methylimidazo[1,5-a]quinoxalin-4(5H)-one, 7-[(5-fluoro-2,3-dihydro-1H-indol-1-yl)carbonyl]-1-(trans-2-hydroxycyclopentyl)-8-methylimidazo[1,5-a]quinoxalin-4(5H)-one, 7-[(5-chloro-2,3-dihydro-1H-indol-1-yl)carbonyl]-1-(trans-2-hydroxycyclopentyl)-8-methylimidazo[1,5-a]quinoxalin-4(5H)-one, 7-[(5-bromo-2,3-dihydro-1H-pyrrolo[2,3-b]pyridin-1-yl)carbonyl]-1-(trans-2-hydroxycyclopentyl)-8-methylimidazo[1,5-a]quinoxalin-4(5H)-one, 7-[(5-fluoro-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 7-[(4,7-difluoro-1,3-dihydro-2H-isoindol-2-yl)carbonyl]-8-methyl-1-(tetrahydrofuran-3-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 8-methyl-1-(tetrahydrofuran-3-yl)-7-{[(5-(trifluoromethyl)-2,3-dihydro-1H-pyrrolo[2,3-b]pyridin-1-yl]carbonyl}imidazo[1,5-a]quinoxalin-4(5H)-one, 8-methyl-7-[(5-methyl-2,3-dihydro-1H-pyrrolo[2,3-b]pyridin-1-yl)carbonyl]-1-(tetrahydro-2H-pyran-3-yl)imidazo[1,5-a]quinoxalin-4(5H)-one, 7-[(5-bromo-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-fluoro-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, 8-methyl-1-(tetrahydro-2H-pyran-4-yl)-7-{[(5-(trifluoromethyl)-2,3-dihydro-1H-pyrrolo[2,3-b]pyridin-1-yl]carbonyl}imidazo[1,5-a]quinoxalin-4(5H)-one, 7-[(5-cyclopropyl-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, 8-(methoxymethyl)-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 7-[(4,7-difluoro-1,3-dihydro-2H-isoindol-2-yl)carbonyl]-8-methoxy-1-(tetrahydro-2H-pyran-4-yl)imidazo[1,5-a]quinoxalin-4(5H)-one, 8-chloro-7-[(4,7-difluoro-1,3-dihydro-2H-isoindol-2-yl)carbonyl]-1-(tetrahydro-2H-pyran-4-yl)imidazo[1,5-a]quinoxalin-4(5H)-one, 8-cyclopropyl-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 7-[(4,7-difluoro-1,3-dihydro-2H-isoindol-2-yl)carbonyl]-8-fluoro-1-(tetrahydro-2H-pyran-4-yl)imidazo[1,5-a]quinoxalin-4(5H)-one, 7-[(4,7-difluoro-1,3-dihydro-2H-isoindol-2-yl)carbonyl]-8-(methoxymethyl)-1-(tetrahydrofuran-3-yl)imidazo[1,5-a]quinoxalin-4(5H)-one, 7-[(5-methoxy-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, 7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, 7-[(5-chloro-2,3-dihydro-1H-indol-1-yl)carbonyl]-8-(methoxymethyl)-1-(tetrahydrofuran-3-yl)imidazo[1,5-a]quinoxalin-4(5H)-one, 7-[(5,6-difluoro-2,3-dihydro-1H-indol-1-yl)carbonyl]-8-(methoxymethyl)-1-(tetrahydrofuran-3-yl)imidazo[1,5-a]quinoxalin-4(5H)-one, 7-[(4,7-difluoro-1,3-dihydro-2H-isoindol-2-yl)carbonyl]-1-(cis-2-hydroxycyclopentyl)-8-methylimidazo[1,5-a]quinoxalin-4(5H)-one, 7-[(5-chloro-2,3-dihydro-1H-indol-1-yl)carbonyl]-1-(3-methoxycyclobutyl)-8-methylimidazo[1,5-a]quinoxalin-4(5H)-one, 7-[(5-bromo-2,3-dihydro-1H-pyrrolo[2,3-b]pyridin-1-yl)
carbonyl]-1-(3-methoxycyclobutyl)-8-methylimidazo[1,
5-a]quinoxalin-4(5H)-one,
1-(3-methoxycyclobutyl)-8-methyl-7-[(5-methyl-2,3-dihy-
dro-1H-pyrrolo[2,3-b]pyridin-1-yl)carbonyl]imidazo[1,
5-a]quinoxalin-4(5H)-one,
1-(3-methoxycyclobutyl)-7-[(5-methoxy-2,3-dihydro-1H-
pyrrolo[2,3-c]pyridin-1-yl)carbonyl]-8-methylimidazo[1,
5-a]quinoxalin-4(5H)-one,
7-{[5-chloro-3-(methoxymethyl)-2,3-dihydro-1H-indol-1-
yl]carbonyl}-8-methyl-1-(tetrahydro-2H-pyran-4-yl)imi-
dazo[1,5-a]quinoxalin-4(5H)-one,
7-[(5-chloro-3-methyl-2,3-dihydro-1H-indol-1-yl)carbo-
nyl]-8-methyl-1-(tetrahydro-2H-pyran-4-yl)imidazo[1,5-
a]quinoxalin-4(5H)-one,
7-[(5-ethyl-2,3-dihydro-1H-pyrrolo[2,3-b]pyridin-1-yl)car-
bonyl]-8-(methoxymethyl)-1-(tetrahydrofuran-3-yl)imi-
dazo[1,5-a]quinoxalin-4(5H)-one,
7-[(4-fluoro-1,3-dihydro-2H-isoindol-2-yl)carbonyl]-8-
(methoxymethyl)-1-(tetrahydrofuran-3-yl)imidazo[1,5-a]
quinoxalin-4(5H)-one,
and salts thereof, and isolated optical isomers thereof.

Examples of the specific compounds included in the above-
described embodiment (6) include the following compounds:
7-[(5-methoxy-2,3-dihydro-1H-pyrrolo[2,3-c]pyridin-1-yl)
carbonyl]-8-(methoxymethyl)-1-(tetrahydrofuran-3-yl)
imidazo[1,5-a]quinoxalin-4(5H)-one,
8-(methoxymethyl)-7-[(5-methyl-2,3-dihydro-1H-pyrrolo
[2,3-b]pyridin-1-yl)carbonyl]-1-(tetrahydrofuran-3-yl)
imidazo[1,5-a]quinoxalin-4(5H)-one,
8-methyl-7-[(5-methyl-2,3-dihydro-1H-pyrrolo[2,3-b]pyri-
din-1-yl)carbonyl]-1-(tetrahydrofuran-3-yl)imidazo[1,5-
a]quinoxalin-4(5H)-one,
7-[(5-methoxy-2,3-dihydro-1H-pyrrolo[2,3-c]pyridin-1-yl)
carbonyl]-8-methyl-1-(tetrahydrofuran-3-yl)imidazo[1,5-
a]quinoxalin-4(5H)-one,
7-[(5-ethyl-2,3-dihydro-1H-pyrrolo[2,3-b]pyridin-1-yl)car-
bonyl]-8-methyl-1-(tetrahydrofuran-3-yl)imidazo[1,5-a]
quinoxalin-4(5H)-one,
7-[(5-bromo-2,3-dihydro-1H-pyrrolo[2,3-b]pyridin-1-yl)
carbonyl]-8-methyl-1-(tetrahydrofuran-3-yl)imidazo[1,5-
a]quinoxalin-4(5H)-one,
7-[(5-fluoro-2,3-dihydro-1H-pyrrolo[2,3-b]pyridin-1-yl)
carbonyl]-8-methyl-1-(tetrahydrofuran-3-yl)imidazo[1,5-
a]quinoxalin-4(5H)-one,
7-[(5-ethyl-2,3-dihydro-1H-pyrrolo[2,3-b]pyridin-1-yl)car-
bonyl]-8-(methoxymethyl)-1-(tetrahydrofuran-3-yl)imi-
dazo[1,5-a]quinoxalin-4(5H)-one,
7-[(5-methoxy-2,3-dihydro-1H-pyrrolo[2,3-b]pyridin-1-yl)
carbonyl]-8-methyl-1-(tetrahydrofuran-3-yl)imidazo[1,5-
a]quinoxalin-4(5H)-one,
8-methyl-1-(tetrahydrofuran-3-yl)-7-{[5-(trifluoromethyl)-
2,3-dihydro-1H-pyrrolo[2,3-b]pyridin-1-yl]
carbonyl}imidazo[1,5-a]quinoxalin-4(5H)-one,
7-[(5-methoxy-2,3-dihydro-1H-pyrrolo[2,3-b]pyridin-1-yl)
carbonyl]-8-(methoxymethyl)-1-(tetrahydrofuran-3-yl)
imidazo[1,5-a]quinoxalin-4(5H)-one,
7-[(5-bromo-2,3-dihydro-1H-pyrrolo[2,3-b]pyridin-1-yl)
carbonyl]-8-(methoxymethyl)-1-(tetrahydrofuran-3-yl)
imidazo[1,5-a]quinoxalin-4(5H)-one,
and salts thereof, and isolated optical isomers thereof In another embodiment, examples of the specific com-
pounds included in the above-described embodiment (6)
include the following compounds:
(+)-7-[(5-methoxy-2,3-dihydro-1H-pyrrolo[2,3-c]pyri-
din-1-yl)carbonyl]-8-(methoxymethyl)-1-(tetrahydrofuran-
3-yl)imidazo[1,5-a]quinoxalin-4(5H)-one,
(−)-7-[(5-methoxy-2,3-dihydro-1H-pyrrolo[2,3-c]pyridin-1-
yl)carbonyl]-8-(methoxymethyl)-1-(tetrahydrofuran-3-
yl)imidazo[1,5-a]quinoxalin-4(5H)-one,
(+)-8-(methoxymethyl)-7-[(5-methyl-2,3-dihydro-1H-pyr-
rolo[2,3-b]pyridin-1-yl)carbonyl]-1-(tetrahydrofuran-3-
yl)imidazo[1,5-a]quinoxalin-4(5H)-one,
(−)-8-(methoxymethyl)-7-[(5-methyl-2,3-dihydro-1H-pyr-
rolo[2,3-b]pyridin-1-yl)carbonyl]-1-(tetrahydrofuran-3-
yl)imidazo[1,5-a]quinoxalin-4(5H)-one,
(+)-7-[(5-methoxy-2,3-dihydro-1H-pyrrolo[2,3-c]pyridin-1-
yl)carbonyl]-8-methyl-1-(tetrahydrofuran-3-yl)imidazo
[1,5-a]quinoxalin-4(5H)-one,
(−)-7-[(5-methoxy-2,3-dihydro-1H-pyrrolo[2,3-c]pyridin-1-
yl)carbonyl]-8-methyl-1-(tetrahydrofuran-3-yl)imidazo
[1,5-a]quinoxalin-4(5H)-one,
(+)-7-[(5-bromo-2,3-dihydro-1H-pyrrolo[2,3-b]pyridin-1-
yl)carbonyl]-8-methyl-1-(tetrahydrofuran-3-yl)imidazo
[1,5-a]quinoxalin-4(5H)-one,
(−)-7-[(5-bromo-2,3-dihydro-1H-pyrrolo[2,3-b]pyridin-1-
yl)carbonyl]-8-methyl-1-(tetrahydrofuran-3-yl)imidazo
[1,5-a]quinoxalin-4(5H)-one,
(+)-7-[(5-bromo-2,3-dihydro-1H-pyrrolo[2,3-b]pyridin-1-
yl)carbonyl]-8-(methoxymethyl)-1-(tetrahydrofuran-3-
yl)imidazo[1,5-a]quinoxalin-4(5H)-one,
(−)-7-[(5-bromo-2,3-dihydro-1H-pyrrolo[2,3-b]pyridin-1-
yl)carbonyl]-8-(methoxymethyl)-1-(tetrahydrofuran-3-
yl)imidazo[1,5-a]quinoxalin-4(5H)-one,
(+)-7-[(5-ethyl-2,3-dihydro-1H-pyrrolo[2,3-b]pyridin-1-yl)
carbonyl]-8-(methoxymethyl)-1-(tetrahydrofuran-3-yl)
imidazo[1,5-a]quinoxalin-4(5H)-one,
(−)-7-[(5-ethyl-2,3-dihydro-1H-pyrrolo[2,3-b]pyridin-1-yl)
carbonyl]-8-(methoxymethyl)-1-(tetrahydrofuran-3-yl)
imidazo[1,5-a]quinoxalin-4(5H)-one,
or salts thereof.

In a further embodiment, examples of the specific com-
pounds included in the above-described embodiment (6)
include the following compounds:
(+)-7-[(5-methoxy-2,3-dihydro-1H-pyrrolo[2,3-c]pyridin-1-
yl)carbonyl]-8-methyl-1-(tetrahydrofuran-3-yl)imidazo
[1,5-a]quinoxalin-4(5H)-one,
(−)-7-[(5-methoxy-2,3-dihydro-1H-pyrrolo[2,3-c]pyridin-1-
yl)carbonyl]-8-methyl-1-(tetrahydrofuran-3-yl)imidazo
[1,5-a]quinoxalin-4(5H)-one,
or salts thereof.

In a still further embodiment, examples of the specific
compounds included in the above-described embodiment (6)
include the following compounds:
(+)-7-[(5-methoxy-2,3-dihydro-1H-pyrrolo[2,3-c]pyri-
din-1-yl)carbonyl]-8-(methoxymethyl)-1-(tetrahydrofuran-
3-yl)imidazo[1,5-a]quinoxalin-4 (5H)-one,
(−)-7-[(5-methoxy-2,3-dihydro-1H-pyrrolo[2,3-c]pyridin-1-
yl)carbonyl]-8-(methoxymethyl)-1-(tetrahydrofuran-3-
yl)imidazo[1,5-a]quinoxalin-4(5H)-one,
(+)-8-(methoxymethyl)-7-[(5-methyl-2,3-dihydro-1H-pyr-
rolo[2,3-b]pyridin-1-yl)carbonyl]-1-(tetrahydrofuran-3-
yl)imidazo[1,5-a]quinoxalin-4(5H)-one,
(−)-8-(methoxymethyl)-7-[(5-methyl-2,3-dihydro-1H-pyr-
rolo[2,3-b]pyridin-1-yl)carbonyl]-1-(tetrahydrofuran-3-
yl)imidazo[1,5-a]quinoxalin-4(5H)-one,
or salts thereof In a still further embodiment, examples of the specific
compounds included in the above-described embodiment (6)
include the following compounds:
(+)-7-[(5-bromo-2,3-dihydro-1H-pyrrolo[2,3-b]pyridin-1-
yl)carbonyl]-8-methyl-1-(tetrahydrofuran-3-yl)imidazo
[1,5-a]quinoxalin-4(5H)-one, (−)-7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, (+)-7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, (−)-7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, or salts thereof In a still further embodiment, examples of the specific compounds included in the above-described embodiment (6) include the following compounds:

(+)-7-[(5-ethyl-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, (+7-[(5-ethyl-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, or salts thereof Examples of the specific compounds included in the above-described embodiment (7) include the following compounds:

8-(methoxymethyl)-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one, 8-methyl-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one, 7-[(5-ethyl-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 7-[(5-fluoro-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 7-[(5-ethyl-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, 8-methyl-1-(tetrahydrofuran-3-yl)-7-{[5-(trifluoromethyl)-2,3-dihydro-1H-pyrrolo[2,3-b]pyridin-1-yl]carbonyl}imidazo[1,5-a]quinoxalin-4(5H)-one, 7-[(5-methoxy-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, 7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, and salts thereof, and isolated optical isomers thereof.

In another embodiment, examples of the specific compounds included in the above-described embodiment (7) include the following compounds:

(+)-8-(methoxymethyl)-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one, (−)-8-(methoxymethyl)-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one, (+)-7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, (−)-7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one, (+)-7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, (−)-7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, (+)-7-[(5-ethyl-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, (−)-7-[(5-ethyl-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one, or salts thereof.

Examples of the specific compounds included in the above-described embodiment (8) include the following compounds:

7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one, 7-[(5-methoxy-2,3-dihydro-1H-pyrrolo[2,3-c]pyridin-1-yl)carbonyl]-8-methyl-1-(tetrahydrofuran-3-yl)imidazo[1,5-a]quinoxalin-4(5H)-one, and salts thereof, and isolated optical isomers thereof In another embodiment, examples of the specific compounds included in the above-described embodiment (8) include the following compounds:

(+)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one, (−)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one, (+)-7-[(5-methoxy-2,3-dihydro-1H-pyrrolo[2,3-c]pyridin-1-yl)carbonyl]-8-methyl-1-(tetrahydrofuran-3-yl)imidazo[1,5-a]quinoxalin-4(5H)-one, (−)-7-[(5-methoxy-2,3-dihydro-1H-pyrrolo[2,3-c]pyridin-1-yl)carbonyl]-8-methyl-1-(tetrahydrofuran-3-yl)imidazo[1,5-a]quinoxalin-4(5H)-one, or salts thereof Examples of the specific compounds included in the above-described embodiment (9) include the following compounds:

7-[(5-bromo-2,3-dihydro-1H-pyrrolo[2,3-b]pyridin-1-yl)carbonyl]-8-methoxy-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-fluoro-1-(tetrahydro-2H-pyran-4-yl)imidazo[1,5-a]quinoxalin-4(5H)-one, 8-fluoro-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-fluoro-7-[(5-fluoro-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-(methoxymethyl)-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-cyclopropyl-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-fluoro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, 8-chloro-7-[(5-methoxy-2,3-dihydro-1'-1-pyrrolo[2,3-c]pyridin-1-yl)carbonyl]-1-(tetrahydro-2H-pyran-4-yl)imidazo[1,5-a]quinoxalin-4(51-1)-one, 7-[(5-bromo-2,3-dihydro-1H-pyrrolo[2,3-b]pyridin-1-yl)carbonyl]-8-chloro-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-(tetrahydrofuran-3-ylmethoxy)-1-(tetrahydro-2H-pyran-4-yl)imidazo[1,5-a]quinoxalin-4(5H)-one, and salts thereof, and isolated optical isomers thereof.

Examples of the specific compounds included in the above-described embodiment (10) include the following compounds:

7-[(5-bromo-2,3-dihydro-1H-pyrrolo[2,3-b]pyridin-1-yl)carbonyl]-8-methoxy-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-fluoro-1-(tetrahydro-2H-pyran-4-yl)imidazo[1,5-a]quinoxalin-4(5H)-one, 8-fluoro-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-fluoro-7-[(5-fluoro-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-(methoxymethyl)-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-cyclopropyl-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-chloro-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-(tetrahydrofuran-3-ylmethoxy)-1-(tetrahydro-2H-pyran-4-yl)imidazo[1,5-a]quinoxalin-4(5H)-one, and salts thereof, and isolated optical isomers thereof.

Examples of the specific compounds included in the above-described embodiment (11) include the following compounds:

8-fluoro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, 8-chloro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, and salts thereof Examples of the specific compounds included in the above-described embodiment (12) include the following compounds:

7-[(5-methoxy-2,3-dihydro-1H-pyrrolo[2,3-c]pyridin-1-yl)carbonyl]-8-methyl-1-(tetrahydro-2H-pyran-3-yl)imidazo[1,5-a]quinoxalin-4(5H)-one, 8-methyl-7-[(5-methyl-2,3-dihydro-1H-pyrrolo[2,3-b]pyridin-1-yl)carbonyl]-1-(tetrahydro-2H-pyran-3-yl)imidazo[1,5-a]quinoxalin-4(5H)-one, 7-[(5-bromo-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-fluoro-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, and salts thereof, and isolated optical isomers thereof.

Examples of the specific compounds included in the above-described embodiment (13) include the following compounds:

8-methyl-7-[(5-methyl-2,3-dihydro-1H-pyrrolo[2,3-b]pyridin-1-yl)carbonyl]-1-(tetrahydro-2H-pyran-3-yl)imidazo[1,5-a]quinoxalin-4(5H)-one, 7-[(5-bromo-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-fluoro-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydro-2H-pyran-3-yl)imidazo[1,5-a]quinoxalin-4(5H)-one, and salts thereof, and isolated optical isomers thereof.

Examples of the specific compounds included in the above-described embodiment (14) include the following compounds:

7-[(5-methoxy-2,3-dihydro-1H-pyrrolo[2,3-c]pyridin-1-yl)carbonyl]-8-methyl-1-(tetrahydro-2H-pyran-3-yl)imidazo[1,5-a]quinoxalin-4(5H)-one, and salts thereof, and isolated optical isomers thereof.

Examples of the specific compounds included in the above-described embodiment (15) include the following compounds:

7-[(5,6-difluoro-2,3-dihydro-1H-indol-1-yl)carbonyl]-8-methyl-1-(tetrahydrofuran-3-yl)imidazo[1,5-a]quinoxalin-4(5H)-one, 7-[(4,7-difluoro-1,3-dihydro-2H-isoindol-2-yl)carbonyl]-8-methyl-1-(tetrahydrofuran-3-yl)imidazo[1,5-a]quinoxalin-4(5H)-one, 7-[(4,7-difluoro-1,3-dihydro-2H-isoindol-2-yl)carbonyl]-8-(methoxymethyl)-1-(tetrahydrofuran-3-yl)imidazo[1,5-a]quinoxalin-4(5H)-one, 7-[(5-chloro-2,3-dihydro-1H-indol-1-yl)carbonyl]-8-(methoxymethyl)-1-(tetrahydrofuran-3-yl)imidazo[1,5-a]quinoxalin-4(5H)-one, 7-[(5,6-difluoro-2,3-dihydro-1H-indol-1-yl)carbonyl]-8-(methoxymethyl)-1-(tetrahydrofuran-3-yl)imidazo[1,5-a]quinoxalin-4(5H)-one, 7-[(4-fluoro-1,3-dihydro-2H-isoindol-2-yl)carbonyl]-8-(methoxymethyl)-1-(tetrahydrofuran-3-yl)imidazo[1,5-a]quinoxalin-4(5H)-one, and salts thereof, and isolated optical isomers thereof In another embodiment, examples of the specific compounds included in the above-described embodiment (15) include the following compounds:

(+)-7-[(5,6-difluoro-2,3-dihydro-1H-indol-1-yl)carbonyl]-8-methyl-1-(tetrahydrofuran-3-yl)imidazo[1,5-a]quinoxalin-4(5H)-one, (−)-7-[(5,6-difluoro-2,3-dihydro-1H-indol-1-yl)carbonyl]-8-methyl-1-(tetrahydrofuran-3-yl)imidazo[1,5-a]quinoxalin-4(5H)-one, (+)-7-[(4,7-difluoro-1,3-dihydro-2H-isoindol-2-yl)carbonyl]-8-methyl-1-(tetrahydrofuran-3-yl)imidazo[1,5-a]quinoxalin-4(5H)-one, (−)-7-[(4,7-difluoro-1,3-dihydro-2H-isoindol-2-yl)carbonyl]-8-methyl-1-(tetrahydrofuran-3-yl)imidazo[1,5-a]quinoxalin-4(5H)-one, (+)-7-[(4,7-difluoro-1,3-dihydro-2H-isoindol-2-yl)carbonyl]-8-(methoxymethyl)-1-(tetrahydrofuran-3-yl)imidazo[1,5-a]quinoxalin-4(5H)-one, (−)-7-[(4,7-difluoro-1,3-dihydro-2H-isoindol-2-yl)carbonyl]-8-(methoxymethyl)-1-(tetrahydrofuran-3-yl)imidazo[1,5-a]quinoxalin-4(5H)-one, or salts thereof Examples of the specific compounds included in the above-described embodiment (16) include the following compounds:

7-[(5-chloro-2,3-dihydro-1H-indol-1-yl)carbonyl]-8-fluoro-1-(tetrahydro-2H-pyran-4-yl)imidazo[1,5-a]quinoxalin-4(5H)-one, 7-{[5-chloro-3-(methoxymethyl)-2,3-dihydro-1H-indol-1-yl]carbonyl}-8-methyl-1-(tetrahydro-2H-pyran-4-yl)imidazo[1,5-a]quinoxalin-4(5H)-one, 7-[(5-chloro-3-methyl-2,3-dihydro-1H-indol-1-yl)carbonyl]-8-methyl-1-(tetrahydro-2H-pyran-4-yl)imidazo[1,5-a]quinoxalin-4(5H)-one, and salts thereof, and isolated optical isomers thereof Examples of the specific compounds included in the above-described embodiment (17) include the following compounds:

7-[(5-chloro-2-methyl-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-{[5-chloro-2-(methoxymethyl)-2,3-dihydro-1H-indol-1-yl]carbonyl}-8-methyl-1-(tetrahydro-2H-pyran-4-yl)[1,2,4]triazolo[4,3-a]quinoxalin-4(5H)-one, 8-methyl-1-(tetrahydro-2H-pyran-4-yl)-7-{[5-(trifluoromethyl)-2,3-dihydro-1H-indol-1-yl]carbonyl}[1,2,4]triazolo[4,3-a]quinoxalin-4(5H)-one, 8-methyl-1-(tetrahydro-2H-pyran-4-yl)-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 7-[(5-bromo-2,3-dihydro-1H-indol-1-yl)carbonyl]-8-methyl-1-(tetrahydro-2,1-pyran-4-yl)[1,2,4]triazolo[4,3-a]quinoxalin-4(5H)-one, 7-[(5-cyclopropyl-2,3-dihydro-1H-pyrrolo[2,3-b]pyridin-1-yl)carbonyl]-8-(methoxymethyl)-1-(tetrahydro-2H-pyran-4-yl)[1,2,4]triazolo[4,3-a]quinoxalin-4(5H)-one, 7-[(5-chloro-2,3-dihydro-1H-indol-1-yl)carbonyl]-8-cyclopropyl-1-(tetrahydro-2H-pyran-4-yl)[1,2,4]triazolo[4,3-a]quinoxalin-4(5H)-one, 7-[(4,7-difluoro-1,3-dihydro-2H-isoindol-2-yl)carbonyl]-8-methyl-1-(tetrahydro-2H-pyran-4-yl)[1,2,4]triazolo[4,3-a]quinoxalin-4(5H)-one, 7-[(5-chloro-3-methyl-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-[(5-bromo-3,3-dimethyl-2,3-dihydro-1H-pyrrolo[2,3-b]pyridin-1-yl)carbonyl]-8-methyl-1-(tetrahydro-2H-pyran-4-yl)[1,2,4]triazolo[4,3-a]quinoxalin-4(5H)-one, and salts thereof, and isolated optical isomers thereof.

Examples of the specific compounds included in the above-described embodiment (18) include the following compounds:

1-(cyclopropylmethyl)-7-[(5-ethyl-2,3-dihydro-1H-pyrrolo[2,3-b]pyridin-1-yl)carbonyl]-8-methyl[1,2,4]triazolo[4,3-a]quinoxalin-4(5H)-one, 7-[(5-chloro-2,3-dihydro-1H-indol-1-yl)carbonyl]-1-(cyclopropylmethyl)-8-ethyl[1,2,4]triazolo[4,3-a]quinoxalin-4(5H)-one, 1-(cyclopropylmethyl)-8-ethyl-7-[(5-fluoro-2,3-dihydro-1H-indol-1-yl)carbonyl][1,2,4]triazolo[4,3-a]quinoxalin-4(5H)-one, 7-[(5-bromo-2,3-dihydro-1H-pyrrolo[2,3-b]pyridin-1-yl)carbonyl]-1-(cyclopropylmethyl)-8-ethyl[1,2,4]triazolo[4,3-a]quinoxalin-4(5H)-one, 7-[(5-bromo-2,3-dihydro-1H-pyrrolo[2,3-b]pyridin-1-yl)carbonyl]-1-(cyclopropylmethyl)-8-methyl[1,2,4]triazolo[4,3-a]quinoxalin-4(5H)-one, 7-[(5-bromo-2,3-dihydro-1H-indol-1-yl)carbonyl]-1-(cyclopropylmethyl)-8-(methoxymethyl)[1,2,4]triazolo[4,3-a]quinoxalin-4(5H)-one, 7-[(5-bromo-2,3-dihydro-1H-pyrrolo[2,3-b]pyridin-1-yl)carbonyl]-1-(cyclopropylmethyl)-8-(methoxymethyl)[1,2,4]triazolo[4,3-a]quinoxalin-4(5H)-one, 7-{[5-chloro-2-(methoxymethyl)-2,3-dihydro-1H-indol-1-yl]carbonyl}-1-cyclopropylmethyl-8-methyl[1,2,4]triazolo[4,3-a]quinoxalin-4(5H)-one, 1-(cyclopropylmethyl)-8-methyl-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 1-(cyclopropylmethyl)-8-methyl-7-[(5-methyl-2,3-dihydro-1H-pyrrolo[2,3-b]pyridin-1-yl)carbonyl][1,2,4]triazolo[4,3-a]quinoxalin-4(5H)-one, 7-[(5-cyclopropyl-2,3-dihydro-1H-pyrrolo[2,3-b]pyridin-1-yl)carbonyl]-1-(cyclopropylmethyl)-8-methyl[1,2,4]triazolo[4,3-a]quinoxalin-4(5H)-one, 1-(cyclopropylmethyl)-7-[(4,7-difluoro-1,3-dihydro-2H-isoindol-2-yl)carbonyl]-8-methyl[1,2,4]triazolo[4,3-a]quinoxalin-4(5H)-one, 1-(cyclopropylmethyl)-8-(methoxymethyl)-7-{[5-(trifluoromethyl)-2,3-dihydro-1H-indol-1-yl]carbonyl}[1,2,4]triazolo[4,3-a]quinoxalin-4(5H)-one, and salts thereof, and isolated optical isomers thereof Examples of the specific compounds included in the above-described embodiment (19) include the following compounds:

7-[(5-chloro-2,3-dihydro-1H-indol-1-yl)carbonyl]-1-(3-methoxycyclobutyl)-8-methyl[1,2,4]triazolo[4,3-a]quinoxalin-4(5H)-one, 7-[(5-bromo-2,3-dihydro-1H-indol-1-yl)carbonyl]-1-(3-methoxycyclobutyl)-8-methyl[1,2,4]triazolo[4,3-a]quinoxalin-4(5H)-one, 1-(3-methoxycyclobutyl)-8-methyl-7-{[5-(trifluoromethyl)-2,3-dihydro-1H-indol-1-yl]carbonyl}[1,2,4]triazolo[4,3-a]quinoxalin-4(5H)-one, 7-[(5-chloro-2,3-dihydro-1H-indol-1-yl)carbonyl]-1-cyclobutyl-8-ethyl[1,2,4]triazolo[4,3-a]quinoxalin-4(5H)-one, 1-cyclobutyl-8-ethyl-7-[(5-fluoro-2,3-dihydro-1H-indol-1-yl)carbonyl][1,2,4]triazolo[4,3-a]quinoxalin-4(5H)-one, 7-[(5-bromo-2,3-dihydro-1H-pyrrolo[2,3-b]pyridin-1-yl)carbonyl]-1-cyclobutyl-8-ethyl[1,2,4]triazolo[4,3-a]quinoxalin-4(5H)-one, 7-[(5-chloro-2,3-dihydro-1H-indol-1-yl)carbonyl]-1-cyclobutyl-8-(methoxymethyl)[1,2,4]triazolo[4,3-a]quinoxalin-4(5H)-one, 7-[(5-bromo-2,3-dihydro-1H-indol-1-yl)carbonyl]-1-cyclobutyl-8-(methoxymethyl)[1,2,4]triazolo[4,3-a]quinoxalin-4(5H)-one, 7-[(5-bromo-2,3-dihydro-1H-pyrrolo[2,3-b]pyridin-1-yl)carbonyl]-1-cyclobutyl-8-(methoxymethyl)[1,2,4]triazolo[4,3-a]quinoxalin-4(5H)-one, 7-[(5-chloro-2-methyl-2,3-dihydro-1H-indol-1-yl)carbonyl]-1-(3-methoxycyclobutyl)-8-methyl[1,2,4]triazolo[4,3-a]quinoxalin-4(5H)-one, 7-{[5-chloro-2-(methoxymethyl)-2,3-dihydro-1H-indol-1-yl]carbonyl}-1-cyclobutyl-8-methyl[1,2,4]triazolo[4,3-a]quinoxalin-4(5H)-one, 1-(3-methoxycyclobutyl)-8-methyl-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 1-cyclobutyl-8-methyl-7-{[5-(trifluoromethyl)-2,3-dihydro-1H-pyrrolo[2,3-b]pyridin-1-yl]carbonyl}[1,2,4]triazolo[4,3-a]quinoxalin-4(5H)-one, 1-cyclobutyl-7-[(4,7-difluoro-1,3-dihydro-2H-isoindol-2-yl)carbonyl]-8-methyl[1,2,4]triazolo[4,3-a]quinoxalin-4(5H)-one, 1-cyclobutyl-8-(methoxymethyl)-7-{[5-(trifluoromethyl)-2,3-dihydro-1H-indol-1-yl]carbonyl}[1,2,4]triazolo[4,3-a]quinoxalin-4(5H)-one, 7-{[5-chloro-3-(methoxymethyl)-2,3-dihydro-1H-indol-1-yl]carbonyl}-1-cyclobutyl-8-methyl[1,2,4]triazolo[4,3-a]quinoxalin-4(5H)-one, 7-[(5-bromo-2,3-dihydro-1H-pyrrolo[2,3-b]pyridin-1-yl)carbonyl]-1-(3-methoxycyclobutyl)-8-methyl[1,2,4]triazolo[4,3-a]quinoxalin-4(5H)-one, 1-cyclobutyl-7-[(4,7-difluoro-1,3-dihydro-2H-isoindol-2-yl)carbonyl]-8-ethyl[1,2,4]triazolo[4,3-a]quinoxalin-4(5H)-one, and salts thereof, and isolated geometrical isomers thereof.

Examples of the specific compounds included in the above-described embodiment (20) include the following compounds:

7-[(5-bromo-2,3-dihydro-1H-pyrrolo[2,3-b]pyridin-1-yl)carbonyl]-1-(cis-2-hydroxycyclopentyl)-8-methylimidazo[1,5-a]quinoxalin-4(5H)-one, 7-[(5-fluoro-2,3-dihydro-1H-indol-1-yl)carbonyl]-1-(cis-2-hydroxycyclopentyl)-8-methylimidazo[1,5-a]quinoxalin-4(5H)-one, 7-[(5,6-difluoro-2,3-dihydro-1H-indol-1-yl)carbonyl]-1-(cis-2-hydroxycyclopentyl)-8-methylimidazo[1,5-a]quinoxalin-4(5H)-one, 7-[(5,6-difluoro-2,3-dihydro-1H-indol-1-yl)carbonyl]-1-(trans-2-hydroxycyclopentyl)-8-methylimidazo[1,5-a]quinoxalin-4(5H)-one, 7-[(5-fluoro-2,3-dihydro-1H-indol-1-yl)carbonyl]-1-(trans-2-hydroxycyclopentyl)-8-methylimidazo[1,5-a]quinoxalin-4(5H)-one, 7-[(5-chloro-2,3-dihydro-1H-indol-1-yl)carbonyl]-1-(trans-2-hydroxycyclopentyl)-8-methylimidazo[1,5-a]quinoxalin-4(5H)-one, 7-[(5-bromo-2,3-dihydro-1H-pyrrolo[2,3-b]pyridin-1-yl)carbonyl]-1-(trans-2-hydroxycyclopentyl)-8-methylimidazo[1,5-a]quinoxalin-4(5H)-one, 7-[(4,7-difluoro-1,3-dihydro-2H-isoindol-2-yl)carbonyl]-1-(cis-2-hydroxycyclopentyl)-8-methylimidazo[1,5-a]quinoxalin-4(5H)-one, and salts thereof, and isolated optical isomers thereof.

Examples of the specific compounds included in the above-described embodiment (21) include the following compounds:

7-[(5-chloro-2,3-dihydro-1H-indol-1-yl)carbonyl]-1-(3-methoxycyclobutyl)-8-methyl[1,2,4]triazolo[4,3-a]quinoxalin-4(5H)-one, 7-[(5-bromo-2,3-dihydro-1H-indol-1-yl)carbonyl]-1-(3-methoxycyclobutyl)-8-methyl[1,2,4]triazolo[4,3-a]quinoxalin-4(5H)-one, 1-(3-methoxycyclobutyl)-8-methyl-7-{[5-(trifluoromethyl)-2,3-dihydro-1H-indol-1-yl]carbonyl}[1,2,4]triazolo[4,3-a]quinoxalin-4(5H)-one, 7-[(5-chloro-2,3-dihydro-1H-indol-1-yl)carbonyl]-1-(3-methoxycyclobutyl)-8-methylimidazo[1,5-a]quinoxalin-4(5H)-one, 7-[(5-bromo-2,3-dihydro-1H-pyrrolo[2,3-b]pyridin-1-yl)carbonyl]-1-(3-methoxycyclobutyl)-8-methylimidazo[1,5-a]quinoxalin-4(5H)-one, 1-(3-methoxycyclobutyl)-8-methyl-7-[(5-methyl-2,3-dihydro-1H-pyrrolo[2,3-b]pyridin-1-yl)carbonyl]imidazo[1,5-a]quinoxalin-4(5H)-one, 1-(3-methoxycyclobutyl)-7-[(5-methoxy-2,3-dihydro-1H-pyrrolo[2,3-c]pyridin-1-yl)carbonyl]-8-methylimidazo[1,5-a]quinoxalin-4(5H)-one, and salts thereof, and isolated optical isomers thereof Examples of the specific compounds included in the above-described embodiment (22) include the following compounds:

7-[(5-ethyl-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, 7-[(5-methoxy-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, 8-methyl-1-(tetrahydro-2H-pyran-4-yl)-7-{[5-(trifluoromethyl)-2,3-dihydro-1H-pyrrolo[2,3-b]pyridin-1-yl]carbonyl}imidazo[1,5-a]quinoxalin-4(5H)-one, 7-[(5-cyclopropyl-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, and salts thereof Examples of the specific compounds included in the above-described embodiment (23) include the following compounds:

7-[(5-bromo-2,3-dihydro-1H-pyrrolo[2,3-b]pyridin-1-yl)carbonyl]-8-methoxy-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-fluoro-1-(tetrahydro-2H-pyran-4-yl)imidazo[1,5-a]quinoxalin-4(5H)-one, 8-fluoro-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-fluoro-7-[(5-fluoro-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-(methoxymethyl)-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, 8-cyclopropyl-7-[(5-methyl-2,3-dihydro-1H-pyrrolo[2,3-b]pyridin-1-yl)carbonyl]-1-(tetrahydro-2H-pyran-4-yl)imidazo[1,5-a]quinoxalin-4(5H)-one, and salts thereof.

Examples of the specific compounds included in the above-described embodiment (24) include the following compounds:

8-fluoro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, 8-chloro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, and salts thereof.

Examples of the specific compounds included in the above-described embodiment (25) include the following compounds:

7-[(5-bromo-2,3-dihydro-1H-pyrrolo[2,3-b]pyridin-1-yl)carbonyl]-8-(tetrahydrofuran-3-ylmethoxy)-1-(tetrahydro-2H-pyran-4-yl)imidazo[1,5-a]quinoxalin-4(5H)-one, 7-[(5-fluoro-2,3-dihydro-1H-indol-1-yl)carbonyl]-8-(tetrahydrofuran-3-ylmethoxy)-1-(tetrahydro-2H-pyran-4-yl)imidazo[1,5-a]quinoxalin-4(5H)-one, and salts thereof, and isolated optical isomers thereof.

Examples of the specific compounds included in the above-described embodiment (26) include the following compounds:

7-({4-[(dimethylamino)methyl]-1,3-dihydro-2H-isoindol-2-yl}carbonyl)-8-methyl-1-(tetrahydro-2H-pyran-4-yl)imidazo[1,5-a]quinoxalin-4(5H)-one, 7-{[4-(methoxymethyl)-1,3-dihydro-2H-isoindol-2-yl]carbonyl}-8-methyl-1-(tetrahydro-2H-pyran-4-yl)imidazo[1,5-a]quinoxalin-4(5H)-one, 7-[(4,7-difluoro-1,3-dihydro-2H-isoindol-2-yl)carbonyl]-8-methoxy-1-(tetrahydro-2H-pyran-4-yl)imidazo[1,5-a]quinoxalin-4(5H)-one, 8-chloro-7-[(4,7-difluoro-1,3-dihydro-2H-isoindol-2-yl)carbonyl]-1-(tetrahydro-2H-pyran-4-yl)imidazo[1,5-a]quinoxalin-4(5H)-one, 7-[(4,7-difluoro-1,3-dihydro-2H-isoindol-2-yl)carbonyl]-8-fluoro-1-(tetrahydro-2H-pyran-4-yl)imidazo[1,5-a]quinoxalin-4(5H)-one, and salts thereof.

The compound of the formula (I) may exist in the form of tautomers or geometrical isomers depending on the kind of substituents. In the present specification, the compound of the formula (I) shall be described in only one form of isomer, yet the present invention includes the other isomers, isolated forms of the isomers, or a mixture thereof.

In addition, the compound of the formula (I) may have asymmetric carbon atoms or axial chirality in some cases, and correspondingly, it may exist in the form of optical isomers. The present invention includes both an isolated form of the optical isomers of the compound of the formula (I) or a mixture thereof.

Furthermore, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, arginine, tromethamine, ornithine, and the like, salts with various amino acids or amino acid derivatives such as acetylleucine and the like, ammonium salts, etc.

In addition, the present invention also includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituent and by applying various known synthesis methods. During the preparation, replacement of the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4th Ed, 2006)" written by P. G. M. Wuts and T. W. Greene, and one of these should only be selected and used as necessary depending on reaction conditions. In this kind of method, a desired compound can be obtained by introducing the protective group, by carrying out a reaction and by eliminating the protective group as necessary.

In addition, the prodrug of the compound of the formula (I) can be produced by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

[Chem. 10]

(wherein A, $R^1$, $R^2$ and $R^3$ represent the same meanings as defined above. R represents lower alkyl. The same shall apply hereinafter.)

The compound (1-1) of the present invention can be obtained by the reaction of a compound (1a) with a compound (1b).

In this reaction, a carboxylic acid (1a) and an amine (1b) in equivalent amounts, or with either thereof in an excess amount are used, and a mixture thereof is stirred under any temperature condition from cooling to heating, preferably at −20° C. to 120° C., usually for 0.1 hours to 5 days, in a solvent which is inert to the reaction, in the presence of a condensation agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, 1,4-dioxane, dimethoxyethane, and the like, N,N-dimethylformamide, N-methylpyrrolidone, dimethylsulfoxide, ethyl acetate, acetonitrile, or water and a mixture thereof. Examples of the condensation agent include 1-(3-dimethylaminopropyl)-3-ethylcarbodiimide, 1,3-dicyclohexylcarbodiimide, 0-(7-azabenzotriazol-1-yl)-N,N,N',N'-tetramethyluronium hexafluorophosphate (HATU), 0-(benzotriazol-1-yl)-N,N,N',N'-tetramethyluronium tetrafluoroborate (TBTU), bromo(tripyrrolidin-1-yl)phosphonium hexafluorophosphate(PyBrop), 1,1'-carbonyldiimidazole (CDI), diphenylphosphoryl azide, and phosphoryl chloride, but are not limited to these, and a condensation agent-supported polystyrene resin, for example, PS-Carbodiimide (Biotage AB, Sweden) can also be used. It may be preferable for the reaction in some cases to use an additive (for example, 1-hydroxybenzotriazole). It may be advantageous in some cases for the smooth progress of the reaction to carry out the reaction in the presence of an organic base such as triethylamine, N,N-diisopropylethylamine, N-methylmorpholine, and the like, or an inorganic base such as potassium carbonate, sodium carbonate, potassium hydroxide, and the like. Further, use of a microwave reactor (Biotage AB) may allow the smooth progress of the reaction in some cases. Depending on the case, an isocyanate-supported polystyrene resin, for example, PS-Isocyanate (Biotage AB, Sweden) and the like can also be used in order to remove an excess amount of amine after completion of the reaction, and also, a quaternary ammonium salt-supported polystyrene resin, for example, MP-Carbonate (Biotage AB, Sweden) and the like can also be used in order to remove an excess amount of the additives after completion of the reaction.

Moreover, a method in which a carboxylic acid (1a) is converted to its reactive derivative and then reacted with amine (1b) can also be used. Examples of the reactive derivative of the carboxylic acid include acid halides that can be obtained by the reaction of a halogenating agent such as phosphoryl chloride, thionyl chloride, and the like, mixed acid anhydrides that can be obtained by the reaction of isobutyl chloroformate or the like, active esters obtained by condensation with 1-hydroxybenzotriazole or the like, etc. The reaction of the reactive derivative and the compound (1b) can be carried out under any temperature condition from cooling to heating, preferably at −20° C. to 60° C., in a solvent which is inert to the reaction, such as halogenated hydrocarbons, aromatic hydrocarbons, ethers, and the like.

In addition, a method in which an aluminum amide reagent obtained by reacting an ester (1c) with trimethylaluminum and amine (1b) is allowed to undergo a reaction can also be used.

For these steps, reference may be made to the methods described in "Organic Functional Group Preparations", written by S. R. Sandler and W. Karo, $2^{nd}$ edition, Vol. 1, Academic Press Inc., 1991, and "Courses in Experimental Chemistry ($5^{th}$ edition)", edited by The Chemical Society of Japan, Vol. 16 (2005) (Maruzen).

In addition, some of the compounds represented by the formula (I) can also be produced from the compound according to the present invention produced as described above by appropriately combining processes usually used by those skilled in the art, such as known alkylation, acylation, substitution, oxidation, reduction, hydrolysis, deprotection, halogenation, and the like (see, for example, "Courses in Experimental Chemistry" (5th Edition), edited by The Chemical Society of Japan, (2005) (Maruzen)). Furthermore, a process which can be usually used by those skilled in the art can also be used for intermediates for preparation.

(Starting Material Synthesis 1)

[Chem. 11]

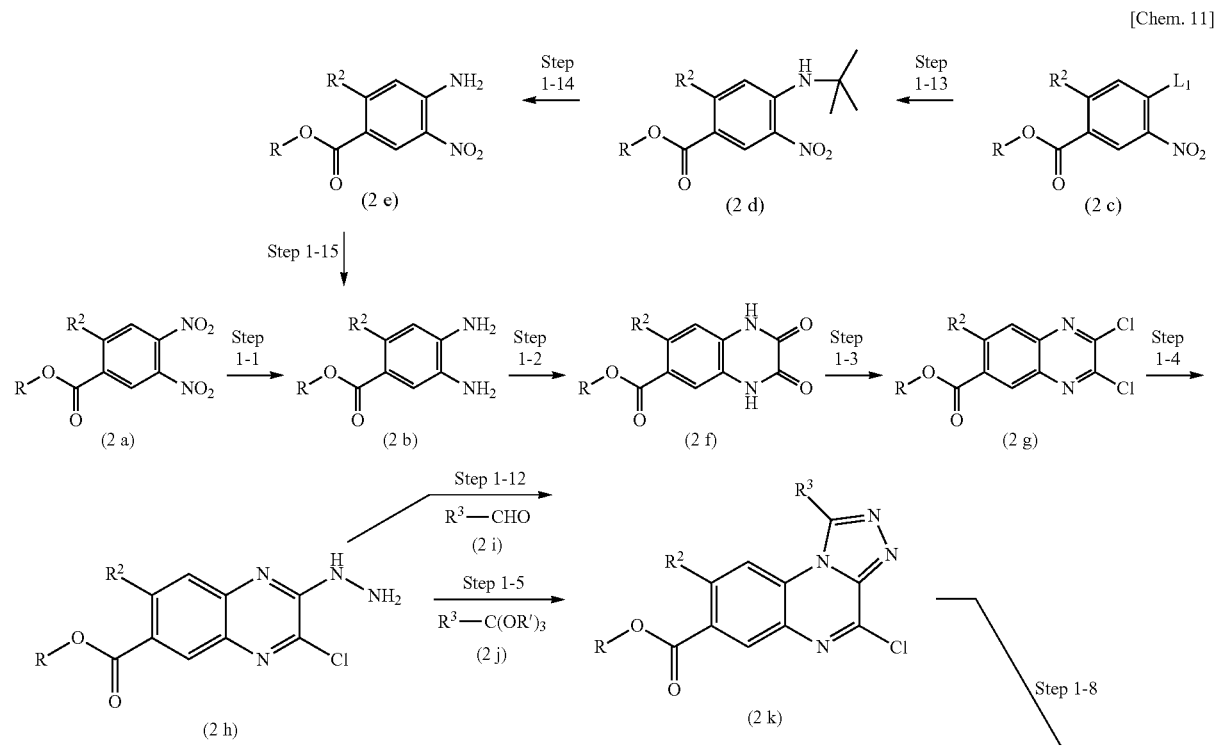

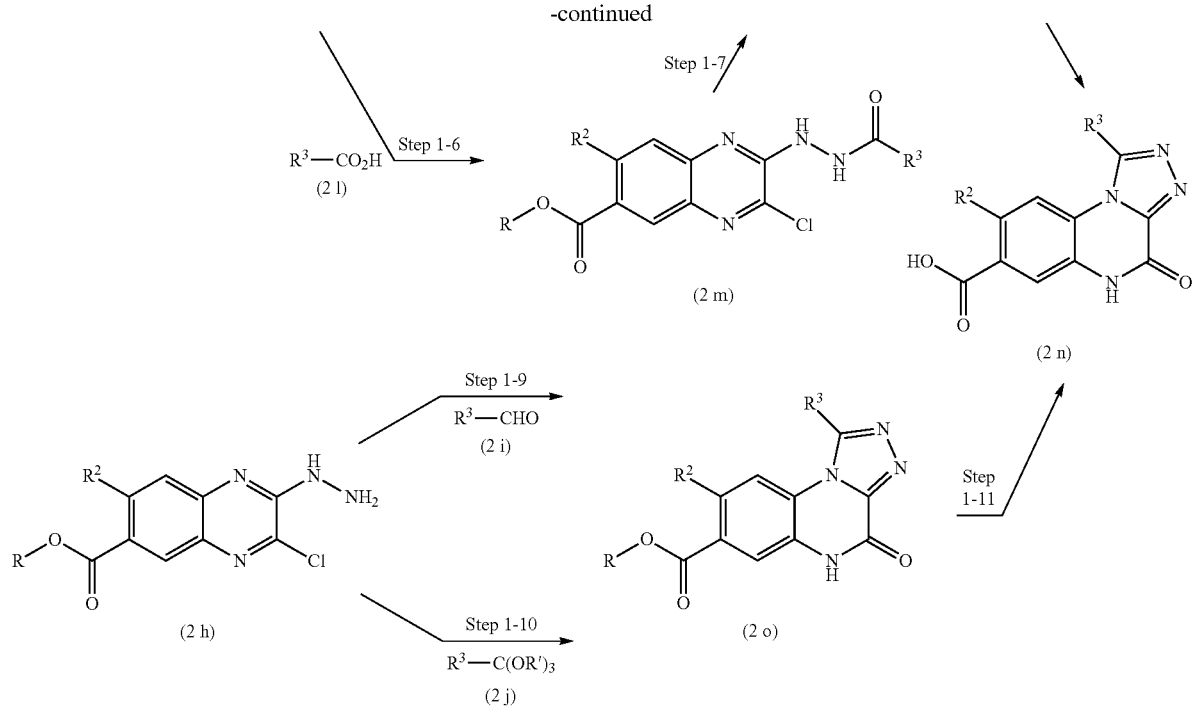

(wherein L₁ means a leaving group and R' means lower alkyl. The same shall apply hereinafter).

The step represented by Step 1-1 is a reaction for obtaining a compound (2b) by a hydrogenation reaction of a compound (2a). In this reaction, the compound (2a) is stirred in the presence of a metal catalyst, usually for 1 hour to 5 days, in a solvent inert to the reaction, under a hydrogen atmosphere. This reaction is usually carried out in a range of normal pressure to increased pressure, and under any temperature condition from cooling to heating, preferably at normal pressure and room temperature. Examples of the solvent used herein are not particularly limited, but include alcohols such as methanol, ethanol, 2-propanol, and the like, ethers such as diethyl ether, tetrahydrofuran, 1,4-dioxane, dimethoxyethane, and the like, water, acetic acid, ethyl acetate, N,N-dimethylformamide, dimethylsulfoxide, and a mixture thereof. As the metal catalyst, palladium catalysts such as palladium on carbon, palladium black, palladium hydroxide, and the like, platinum catalysts such as a platinum plate, platinum oxide, and the like, nickel catalysts such as reduced nickel, Raney nickel, and the like, rhodium catalysts such as tetrakistriphenylphosphine chlororhodium and the like, etc. are preferably used. Instead of hydrogen gas, formic acid, ammonium formate, or hydrazine monohydrate in equivalent amounts, or with either thereof in an excess amount can be used as a hydrogen source, relative to the compound (2a). This step further includes a reaction for obtaining a compound (2b) by a reduction reaction of a compound (2a). In this reaction, the compound (2a) is stirred in the presence of an iron catalyst such as reduced iron, activated carbon/iron (III) chloride, and the like, usually for 0.5 hours to 5 days, in a solvent inert to the reaction. This reaction is usually carried out under any temperature condition from cooling to heating, preferably at 0° C. to 100° C. For this step, reference may be made to the methods described in "Reductions in Organic Chemistry, 2$^{nd}$ ed. (ACS Monograph: 188)" written by M. Hudlicky, ACS, 1996, "Courses in Experimental Chemistry" (4th Edition), edited by The Chemical Society of Japan, Vol. 26 (1992) (Maruzen), and the like.

The step represented by Step 1-13 is a reaction for obtaining a compound (2d) by the reaction of the compound (2c) and tert-butylamine. In this reaction, the compound (2c) and tert-butylamine in equivalent amounts, or with either thereof in an excess amount are used, and a mixture thereof is stirred under any temperature condition from cooling to heating to reflux, preferably at 0° C. to 80° C., usually for 0.1 hours to 5 days, in a solvent which is inert to the reaction or without a solvent. The solvent as used herein is not particularly limited, but examples thereof include aromatic hydrocarbons such as benzene, toluene, xylene, and the like, ethers such as diethyl ether, tetrahydrofuran, 1,4-dioxane, dimethoxyethane, and the like, halogenated hydrocarbons such as dichloromethane, 1,2-dichloroethane, chloroform, and the like, N,N-dimethylformamide, N,N-dimethylacetamide, dimethylsulfoxide, ethyl acetate, acetonitrile, N-methylpyrrolidone, N-ethylpyrrolidone, and a mixture thereof. It may be advantageous in some cases for the smooth progress of the reaction to carry out the reaction in the presence of an organic base such as triethylamine, N,N-diisopropylethylamine, pyridine, N-methylmorpholine, and the like, or an inorganic base such as sodium hydroxide, potassium carbonate, sodium carbonate, potassium hydroxide, and the like. For this step, reference may be made to the methods described in "Organic Functional Group Preparations", written by S. R. Sandler and W. Karo, 2" edition, Vol. 1, Academic Press Inc., 1991, "Courses in Experimental Chemistry (5$^{th}$ edition)", edited by The Chemical Society of Japan, Vol. 14 (2005) (Maruzen), and the like.

The step represented by Step 1-14 is a reaction for obtaining a compound (2e) by a dealkylation reaction of the compound (2d). Here, the dealkylation reaction can be carried out with reference to the method described in "Greene's Protective Groups in Organic Synthesis (4$^{th}$ edition, 2006)".

The step represented by Step 1-15 is a reaction for obtaining a compound (2b) by a hydrogenation reaction of the compound (2e), for which the method used in Step 1-1 can be incorporated. Further, this step also includes a reaction for obtaining the compound (2b) by a reduction reaction of the compound (2e), for which the method used in Step 1-1 can be incorporated.

The step represented by Step 1-2 is a reaction for obtaining a compound (2f) by a cyclization reaction of the compound (2b) with diethyl oxalate ((COOEt)$_2$) or oxalic acid. For this step, reference may be made to the methods described in J. Med. Chem., 38 (19): pp. 3720-3740 (1995), the specification of US Patent Application Publication No. 2004/192698, and the like.

The step represented by Step 1-3 is a reaction for obtaining a compound (2g) by chlorination of the compound (2f). In this reaction, a chlorinating agent is used in equivalent amounts, or with either thereof in an excess amount, relative to the compound (2f), and a mixture thereof is stirred under any temperature condition from cooling to heating to reflux, preferably from room temperature to heating to reflux, usually for 0.1 hours to 5 days, in a solvent which is inert to the reaction or without a solvent. The solvent as used herein is not particularly limited, but examples thereof include aromatic hydrocarbons such as benzene, toluene, xylene, and the like, ethers such as tetrahydrofuran, 1,4-dioxane, dimethoxyethane, and the like, halogenated hydrocarbons such as 1,2-dichloroethane, chloroform, and the like, acetonitrile, and a mixture thereof. It may be advantageous in some cases for the smooth progress of the reaction to carry out the reaction in the presence of N,N-dimethylformamide or N,N-diethylaniline, and the like. Examples of the chlorinating agent include phosphoryl chloride, phosphorous pentachloride, and thionyl chloride.

The step represented by Step 1-4 is a reaction for obtaining a compound (2h) by the reaction of the compound (2g) with hydrazine (NH$_2$NH$_2$) monohydrate, for which the method used in Step 1-13 can be incorporated.

Each of the steps represented by Step 1-5 and Step 1-10 is a reaction for obtaining a compound (2k) or a compound (2o) by a cyclization reaction, or a cyclization reaction and hydrolysis of the compound (2h) and the compound (2j). In this reaction, the compound (2j) is used in an equivalent amount or an excess amount, relative to the compound (2h), and a mixture thereof is stirred under any temperature condition from cooling to heating to reflux, preferably at room temperature to under heating to reflux, usually for 0.1 hours to 5 days, in a solvent which is inert to the reaction or without a solvent. For this step, reference may be made to the method described in J. Med. Chem., 33 (8): pp. 2240-2254 (1990).

The step represented by Step 1-6 is a reaction for obtaining a compound (2m) by the reaction of the compound (2h) with the compound (2l), for which the method used in (Production Process 1) can be incorporated.

The step represented by Step 1-7 is a reaction for obtaining a compound (2k) by the reaction of the compound (2m) with thionyl chloride, for which the method used in (Step 1-3) can be incorporated.

Each of the steps represented by Step 1-8 and Step 1-11 is a reaction for obtaining a compound (2n) by a hydrolysis reaction of the compound (2k) or the compound (2o). Here, the hydrolysis reaction can be carried out with reference to the method described in "Greene's Protective Groups in Organic Synthesis (4$^{th}$ edition, 2006)".

Each of the steps represented by Step 1-9 and Step 1-12 is a reaction for obtaining a compound (2k) or a compound (2o) by the reaction of the compound (2h) with the compound (2i). In this reaction, the compound (2h) and the compound (2i) in equivalent amounts, or with either thereof in an excess amount are used, and a mixture thereof is stirred under any temperature condition from room temperature to heating to reflux, usually for 1 to 5 days, in a solvent which is inert to the reaction or without a solvent, in the presence of an oxidant. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, 1,4-dioxane, dimethoxyethane, and the like, N,N-dimethylformamide, dimethylsulfoxide, acetic acid, ethylene glycol, ethyl acetate, acetonitrile, water, hydrochloric acid, and a mixture thereof. Examples of the oxidant include copper acetate, copper chloride, bromine, chloranil, 2,3-dichloro-5,6-dicyano-p-benzoquinone, and the like. In this reaction, each of imine formation by dehydration, cyclization using an oxidant, and hydrolysis can be carried out stepwise. For this step, reference may be made to the method described in Indian J. Chem., 38B: pp. 45-51, 1371-1373 (1999).

(Starting Material Synthesis 2)

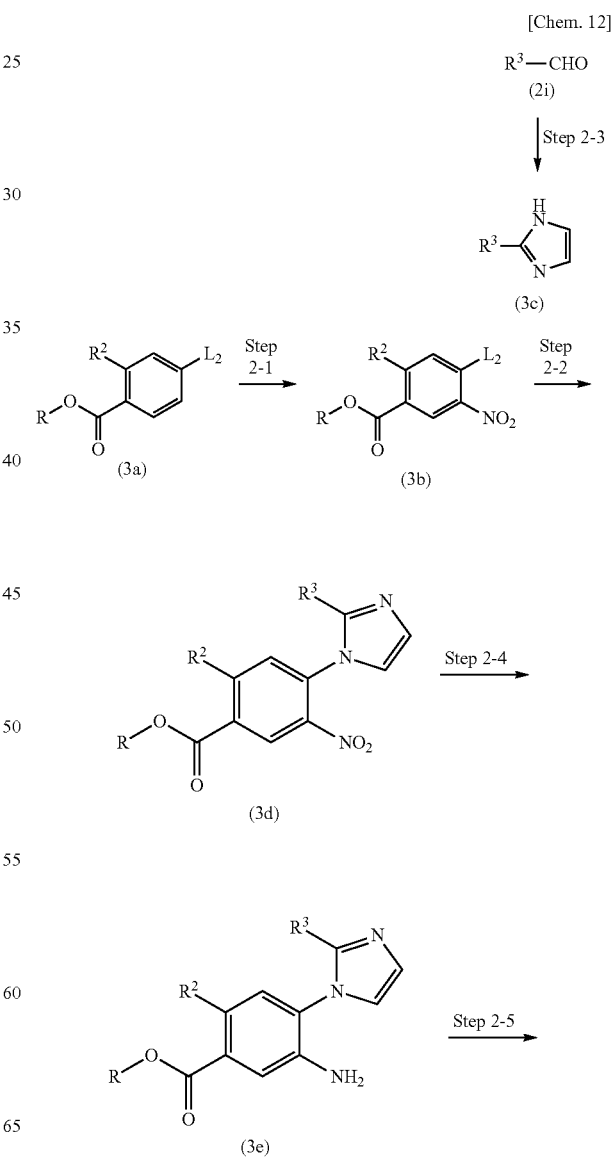

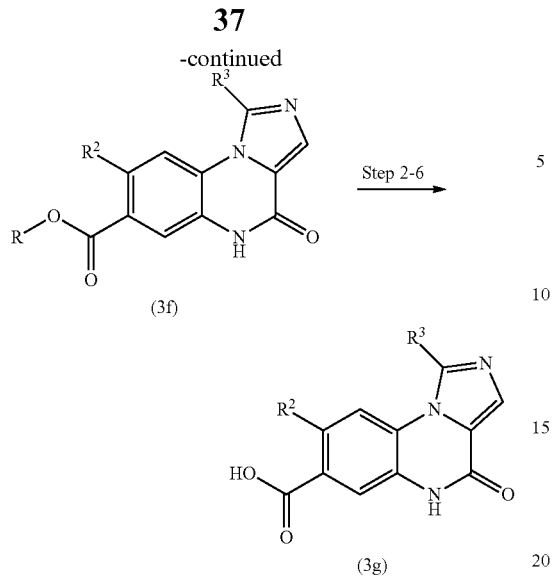

(wherein L$_2$ represents a leaving group).

Step 2-1 is a step for obtaining a compound (3b) by a nitration reaction of the compound (3a), and examples of the nitrating agent include nitric acid, a mixture of nitric acid and sulfuric acid (mixed acid), a mixture of a metal nitrate such as lithium nitrate, sodium nitrate, potassium nitrate, and the like and sulfuric acid, nitronium salts such as nitronium tetrafluoroborate and the like, acetyl nitrate, etc. For this step, reference may be made to the method described in "Courses in Experimental Chemistry (5$^{th}$ edition)", edited by The Chemical Society of Japan, Vol. 14 (2005) (Maruzen), and the like.

Step 2-2 is a step for obtaining a compound (3d) by the reaction of the compound (3b) and the compound (3c), for which the method used in Step 1-4 of (Starting Material Synthesis 1) can be incorporated. Here, examples of the leaving group include halogen, a methanesulfonyloxy group, a p-toluenesulfonyloxy group, and the like.

Step 2-3 is a step for obtaining a compound (3c) by a cyclization reaction of the compound (2i), which can be carried out in the presence of glyoxal, or dichloroacetaldehyde and aqueous ammonia. For this step, reference may be made to the method described in Angew. Chem. Int. Ed. Engl., 22 (7): pp. 560-561 (1983).

Step 2-4 is a step for obtaining a compound (3e) by a hydrogenation reaction of the compound (3d), for which the method used in Step 1-1 of (Starting Material Synthesis 1) can be incorporated.

Step 2-5 is a step for obtaining a compound (3f) by a cyclization reaction of the compound (3e) with 1,1'-carbonyldiimidazole (CDI) or triphosgene. For this step, reference may be made to the method described in J. Med. Chem., 34 (9): pp. 2671-2677 (1991).

Step 2-6 is a step for obtaining a compound (3g) by the hydrolysis reaction of the compound (3f), for which the method used in Step 1-11 of (Starting Material Synthesis 1) can be incorporated.

The compounds of the formula (I) can be isolated and purified as their free compounds, salts, hydrates, solvates, or polymorphic crystal substances thereof. The salts of the compound of the formula (I) can also be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting material.

The pharmacological activity of the compound of the formula (I) was confirmed by the tests shown below.

Test Example 1

PDE9-Inhibiting Activity (1) Acquisition of PDE9

The PDE9 used in the present experiment was expressed/purified by the method as in, for example, Guipponi et al., and Fisher et., al. (Fisher, D. A., et al., J. Biol. Chem., 273: pp. 15559-15564 (1998), Guipponi, M., et al., Hum. Genet., 103: pp. 386-392 (1998)).

(2) Evaluation of PDE9-Inhibiting Activity

The PDE9-inhibiting activity was measured by the following method. That is, to a buffer solution containing tris(hydroxymethyl)aminomethane-hydrochloric acid (40 mM, pH 8.0), magnesium chloride (5 mM), and 2-mercaptoethanol (4 mM) were added cGMP (1 µM) and $^3$H-cGMP (0.33 µCi/ml) to give a substrate buffer solution. A test substance solution and an enzyme solution which had been adjusted to an optimal concentration were added thereto to perform a reaction at 30° C. The enzyme reaction was stopped by the addition of Scintillation Proximity Assay (SPA) Beads (Perkin Elmer, USA) containing 5 mM 3-isobutyl-1-methylxanthine (IBMX). For the enzyme activity, the amount of 5'-GMP, which is a reaction degradation product bound to SPA beads, was measured with a TopCount microplate reader (Hewlett Packard, USA).

The inhibitory rate was calculated by taking the radioactivity of the control containing no test substance as (A), taking the radioactivity of the blank containing no enzyme as (B), and taking the radioactivity of the test substance as (C), and using the following equation.

$$\text{Inhibitory rate}=100-\{(C)-(B)/(A)-(B)\}\times 100(\%)$$

In addition, the IC$_{50}$ value was calculated as a compound concentration which inhibits the results obtained by 50% by a Logistic regression method.

(3) Other Evaluation of PDE-Inhibiting Activity

For the PDE1, a recombinant enzyme was purchased (BPS Bioscience Inc., USA). The PDE2 was expressed/purified by a method of Yang et., al. (Yang, Q., et al., Biochem. Biophys. Res. Commun., 205: pp. 1850-1858 (1994)), and the PDE4 was expressed/purified by a method of Nemoz et., al. (Nemoz, G., et al., FEBS Lett., 384: pp. 97-102 (1996)). The PDE3, PDE5, and PDE6 were isolated from rabbit myocardium, rabbit prostate, and rat retina. That is, desired tissues were selected from each of the animals, and chipped in a buffer solution containing bis(2-hydroxyethyl)iminotris(hydroxymethyl)aminomethane (20 mM), dithioerythritol (5 mM), glycol ether diamine tetraacetic acid (2 mM), and sodium acetate (50 mM). Then, the cells were crushed using a Poritoron homogenizer. Each tissue homogenates were ultracentrifuged (100,000 g, 4° C., 60 minutes), and then, the supernatant was added to a Q Sepharose column. By the concentration gradient of a buffer solution containing 0.05 to 1.2 M sodium acetate, sodium chloride (140 mM), potassium chloride (5 mM), glucose (5 mM), and 2-[4-(2-hydroxyethyl)-1-piperazinyl]ethanesulfonic acid (10 mM), elution was performed by ion exchange to obtain a fraction as a source of enzymes. For each of the eluate fractions, PDE subtypes were identified by enzymatic properties and selective inhibitor susceptibility.

For the PDE enzyme activity, the degradability for cAMP or cGMP was measured by the amount of 5'-AMP or 5'-GMP, which is a reaction degradation product bound to SPA beads, by the method as in PDE9 above.

For the compound of the formula (I), the PDE9-inhibiting activity action was confirmed by the test method above. For example, the following Example compounds exhibited the following PDE9-inhibiting activity actions ($IC_{50}$ values: nM).

Example 1 (3.5), Example 2 (51), Example 3 (22), Example 4(a) (62), Example 4(b) (11), Example 5 (62), Example 6 (64), Example 7 (2.1), Example 8 (2.8), Example 9 (1.3), Example 10 (4.5), Example 11 (31), Example 12 (3.6), Example 13 (14), Example 14 (14), Example 15 (2.8), Example 16 (3.3), Example 17 (8.5), Example 18 (5.4), Example 21 (22), Example 22 (56), Example 23 (4.9), Example 24 (17), Example 25(a) (62), Example 25(b) (14), Example 26(a) (152), Example 26(b) (45), Example 27 (84), Example 27(a) (137), Example 27(b) (26), Example 28 (52), Example 28(a) (139), Example 28(b) (47), Example 29 (15), Example 29(a) (24), Example 29(b) (5.6), Example 30 (11), Example 30(a) (38), Example 30(b) (5.8), Example 31 (1.4), Example 32 (2.6), Example 33 (0.81), Example 34 (7.5), Example 35 (19), Example 36 (53), Example 37 (53), Example 38 (28), Example 39(a) (52), Example 39(b) (14), Example 40(a) (77), Example 40(b) (16), Example 41 (18), Example 42 (13), Example 43(a) (25), Example 43(b) (2.8), Example 44 (6.1), Example 45(a) (26), Example 45(b) (8.9), Example 46 (13), Example 47 (2.1), Example 48 (0.8).

Furthermore, it was confirmed that the compounds of the formula (I), in particular, lots of the Example compounds have a selective PDE9-inhibiting activity. The selective PDE9-inhibiting activity refers to a further potent inhibiting activity than the inhibiting activity, particularly on PDE1, PDE3 and PDE6, and it is, for example, a case where the $IC_{50}$ value (nM) is 1/10 or less, as compared with any of PDE1, PDE3 and PDE6, preferably a case where the $IC_{50}$ value (nM) is 1/50 or less, as compared with 1, 2, or all of PDE1, PDE3 and PDE6, and more preferably a case where the $IC_{50}$ value (nM) is 1/100 or less, as compared with 1, 2, or all of PDE1, PDE3 and PDE6.

Test Example 2

Evaluation of PDE9-Inhibiting Activity in Cells

A CRE-luc gene in which a luciferase (luc) gene was linked to the PDE9 gene and the cyclic AMP response element (CRE) gene in the HEK293 cell was transiently introduced to prepare a PDE9 and CRE-luc co-expressing cell. The next day, a 0.5 mM IBMX and a test substance solution were added to the cells and cultured at 37° C. for 6 hours, and then the culture supernatant was removed. 0.2% Triton X-100-containing phosphate buffer solution was added thereto to crush the cells. The PDE9-inhibiting activity in the cell was evaluated by adding a luciferin substrate liquid to the cell solution obtained by crushing the cells and measuring the luciferase activity in a fluorescence/illuminant plate reader.

As a result, it was confirmed that there are some compounds exhibiting the effective activity among the compounds of the present invention.

Test Example 3

Action in Simultaneous Measurement Model for Rat Bladder Contraction/Urethra Relaxation Responses Simultaneous measurement of the bladder contraction and urethra relaxation responses using a rat was carried out with a partial modification of a method in Wibberley et al., (Wibberley, A., et al., Br. J. Pharmacol., 136: pp. 399-414 (2002)). That is, a female Sprague-Dawley (SD) rat (Charles River Laboratories Japan, Inc.) was anesthetized with urethane, and the bladder was exposed by a midline incision in the lower abdomen. A double lumen cannula (a cannula having a dual structure by PE190 and PE50) from the bladder apex was inserted into the bladder, and the bladder apex and the cannula were fixed by sutures at a point where the tip reached the proximal urethra. While infusing physiological saline into the urethra through the outer cannula, the urethral inner pressure was measured by a pressure transducer through the inner cannula with a saline solution infused into the urethra through the outer cannula. On the other hand, a single cannula (PE50) was inserted into the bladder from the bladder apex and placed therein. The inner pressure of the bladder was measured through this cannula. After a postoperative stabilization period had passed, physiological saline was infused into the bladder through the cannula of the bladder apex to cause a bladder contraction reaction, and thus cause a urethra relaxation response accompanying the bladder contraction reflex. The test substance was administered intravenously or intraduodenally.

As a result, it was confirmed that there are some compounds exhibiting the effective activity among the compounds of the formula (I). For some of the compounds of the formula (I), the ratio with increased urethra relaxation time during voiding at 1 mg/kg (increase relative to the solvent administration group (vs vehicle) (%)) is shown. Example 4(b) (167), Example 25(b) (131), Example 27(b) (181), Example 29(b) (149), Example 30(b) (147), Example 31 (149), Example 43(b) (138), Example 45(b) (141).

Test Example 4

Action in Rat Drug-Induced Voiding Dysfunction Model

A male SD rat (Japan SLC, Inc.) was put under anesthesia to place a cannula in the bladder and the jugular vein and was later aroused in a Ballman cage. After a postoperative stabilization period, physiological saline was infused into the bladder to cause voiding. Infusion of the physiological saline was stopped immediately after voiding, and the amount of the drained urine was measured using a pan balance placed under a Ballman cage. After completion of voiding, the residual urine was collected by gravity through a cannula placed in the bladder, and the weight was measured. Further, the inner pressure of the bladder was measured by a pressure transducer through the bladder cannula. Voiding dysfunction was caused by intravenous administration of one or a combination of an anticholinergic agent, an $\alpha_1$ receptor agonist and an NO production inhibitor, and the voiding dynamics were observed after the drug administration. The test substance was administered intravenously, orally or gastrically.

As a result, it was confirmed that there are some compounds exhibiting the effective activity among the compounds of the formula (I).

As a result of the test above, it was confirmed that some of the compounds of the formula (I) has a PDE9-inhibitory action and it was confirmed that some of the compounds of the formula (I) have a urethra relaxation action during voiding in the animal models as well. Accordingly, the compound of the formula (I) can be used for preventing or treating diseases related to degradation of cGMP by PDE9, for example, diseases such as storage dysfunction, voiding dysfunction, bladder/urethral diseases, in another embodiment, underactive bladder, hypotonic bladder, acontractile bladder, detrusor underactivity, neurogenic bladder, urethra relaxation failure or detrusor-external urethral sphincter dyssynergia, overactive bladder and lower urinary tract symptoms thereof, and benign prostatic hyperplasia, interstitial cystitis, chronic prostatitis, urethra calculus and lower urinary tract symptoms accompanying them, and the like, and in a further embodiment, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, urethra calculus, and the like.

In addition, the compounds of the formula (I) have a selective PDE9-inhibiting activity, and as a result, the side effects derived from the action of other PDE subtypes can be avoided, whereby the compounds can be excellent therapeutic agents having higher safety. For example, cardiovascular risk derived from the PDE3 inhibitory action or the risk of blindness derived from the PDE6 inhibitory action can be avoided (A. M. Laties Drug Safety 2009; 32, 1-18/J. B. Shipley et al., Am. J. Med. Sci., 1996; 311, 286-291/T. M. Vinogradova et al., Circ. Res., 2008; 102, 761-769).

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

The solid composition for use in the oral administration according to the present invention is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent and a suspending agent, sweeteners, flavors, aromatics and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizing agent or a solubilizing agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

In oral administration, the daily dose is generally from about 0.001 to 100 mg/kg, preferably from 0.1 to 30 mg/kg, and more preferably from 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing diseases for which the compound of the formula (I) is considered to be effective. The combined preparation may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples as described below. Furthermore, the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

In addition, for salt forming reactions that are apparent to a person skilled in the art, there are cases where addition or omission to or of the specific preparation methods of Examples.

The following abbreviations may be used in some cases in the Examples, Preparation Examples, and Tables below. tert-: Tertiary, Pr: Preparation Example No., Ex: Example No., No: Compound No., Structure: Structural formula, Syn: Preparation method (the numeral shows that the Example compound was prepared in the same manner as a compound having its number as the Example No.), Data: Physicochemical data, ESI+: m/z values in mass spectroscopy (Ionization ESI, representing $(M+H)^+$ unless otherwise specified), ESI−: m/z values in mass spectroscopy (Ionization ESI, representing $(M-H)^-$ unless otherwise specified), EI+: m/z values in mass spectroscopy (Ionization EI, representing $(M)^+$ unless otherwise specified), FAB+: m/z values in mass spectroscopy (Ionization FAB, representing $(M+H)^+$ unless otherwise specified), FAB−: m/z values in mass spectroscopy (Ionization FAB, representing $(M-H)^-$ unless otherwise specified), APCI+: m/z values in mass spectroscopy (Ionization APCI, representing $(M+H)^+$ unless otherwise specified), APCI/ESI+: m/z values in mass spectroscopy (Ionization APCI and ESI simultaneously performed, representing $(M+H)^+$ unless otherwise specified), APCI/ESI−: m/z values in mass spectroscopy (Ionization APCI and ESI simultaneously performed, representing $(M-H)^-$ unless otherwise specified), mp.: Melting point (° C.), dec.: decomposition, NMR: δ (ppm) of peak in $^1$H NMR, s: singlet (spectrum), d: doublet (spectrum), t: triplet (spectrum), q: quartet (spectrum), and br: broad line (spectrum) (example: br s). Further, HCl in the structural formula represents hydrochloride (the numeral prefixed to HCl denotes a molar ratio), RT represents a retention time, and the eluant represents a solvent for preparative HPLC. A case where there is a description of "chiral" in the structural formula indicates that the Example compound is an optically active form, but there are some cases where the stereochemistry is not determined. A case where there is no description of "chiral" in the structural formula indicates that the Example compound is a mixture of geometrical isomers, or a racemate. Accordingly, a case where there is a description of stereochemistry but there is no description of "chiral" indicates a racemic mixture of diastereomers having relative configurations, and a case where there is neither a description of stereochemistry nor a description of "chiral" indicates a mixture of geometrical isomers, or a mixture of optical isomers. In addition, [M] of the concentration represents [mol/L].

Preparation Example 1

To 649 mg of methyl 4-chloro-8-methyl-1-(tetrahydro-2H-pyran-4-yl[1,2,4]triazolo[4,3-a]quinoxaline-7-carboxylate was added 12 mL of 6 M hydrochloric acid, followed by heating to reflux for 20 hours. After ice-cooling, the precipitated solid was filtered, and washed with water and diethyl ether. The obtained solid was dried under reduced pressure to obtain 307 mg of 8-methyl-4-oxo-1-(tetrahydro-2H-pyran-4-yl)-4,5-dihydro[1,2,4]triazolo[4,3-a]quinoxaline-7-carboxylic acid as a solid.

Preparation Example 2

To a mixture of 4.54 g of methyl 8-(methoxymethyl)-4-oxo-1-(tetrahydrofuran-3-yl)-4,5-dihydroimidazo[1,5-a]quinoxaline-7-carboxylate and 45.0 mL of methanol was added 17.0 mL of a 3 M aqueous sodium hydroxide solution, followed by stirring at 70° C. for 5 hours. Concentrated hydrochloric acid and 1 M hydrochloric acid were added thereto to adjust the pH to about 3, and the precipitated solid was collected by filtration and dried under reduced pressure to obtain 4.31 g of 8-(methoxymethyl)-4-oxo-1-(tetrahydrofuran-3-yl)-4,5-dihydroimidazo[1,5-a]quinoxaline-7-carboxylic acid as a white solid.

Preparation Example 3

To a mixture of 10 g of methyl 3-chloro-2-hydrazino-7-methylquinoxaline-6-carboxylate, 5.9 g of tetrahydro-2H-pyran-4-carboxylic acid, 16 mL of triethylamine, and 100 mL of dichloromethane was added 21 g of bromo(tripyrrolidin-1-yl)phosphonium hexafluorophosphate, followed by stirring at room temperature for 9 hours. To the reaction mixture were added saturated aqueous sodium hydrogen carbonate solution and chloroform. The solid was collected by filtration and washed with ethyl acetate to obtain 9.1 g of methyl 3-chloro-7-methyl-2-[2-(tetrahydro-2H-pyran-4-ylcarbonyl)hydrazino]quinoxaline-6-carboxylate as a pink solid. Further, to the filtrate obtained above was added chloroform, and then the aqueous layer was separated. The organic layer was washed with saturated brine and dried over anhydrous magnesium sulfate. The solvent was evaporated under reduced pressure and the obtained residue was washed with ethyl acetate to obtain 3.58 g of methyl 3-chloro-7-methyl-2-[2-(tetrahydro-2H-pyran-4-ylcarbonyl)hydrazino]quinoxaline-6-carboxylate as a colorless solid.

Preparation Example 4

To a mixture of 12.7 g of methyl 3-chloro-7-methyl-2-[2-(tetrahydro-2H-pyran-4-ylcarbonyl)hydrazino]quinoxaline-6-carboxylate and 250 mL of tetrahydrofuran was added 5 mL of thionyl chloride, followed by stirring at 70° C. overnight. After cooling to room temperature, the solvent was evaporated under reduced pressure and the obtained solid was washed with diethyl ether to obtain 10.4 g of methyl 4-chloro-8-methyl-1-(tetrahydro-2H-pyran-4-yl)[1,2,4]triazolo[4,3-a]quinoxaline-7-carboxylate as a pale yellow solid.

Preparation Example 5

A mixture of 5.3 g of methyl 2-methyl-4,5-dinitrobenzoate, 1.06 g of 10% palladium on carbon (50% water wet), 53 mL of ethanol, and 53 mL of 1,4-dioxane was vigorously stirred at room temperature overnight under a hydrogen atmosphere. The insoluble material was filtered and washed with methanol. The filtrate was concentrated, and then dried under reduced pressure to obtain 3.98 g of methyl 4,5-diamino-2-methyl benzoate.

Preparation Example 6

A mixture of 3.98 g of methyl 4,5-diamino-2-methyl benzoate and 40 mL of diethyl oxalate was stirred at 145° C. for 3 hours. After cooling to room temperature, the solid was collected by filtration, washed with diethyl ether, and dried under reduced pressure to obtain 4.75 g of methyl 7-methyl-2,3-dioxo-1,2,3,4-tetrahydroquinoxaline-6-carboxylate.

Preparation Example 7

A mixture of 4.75 g of methyl 7-methyl-2,3-dioxo-1,2,3,4-tetrahydroquinoxaline-6-carboxylate and 38 mL of phosphoryl chloride was heated to reflux for 35 hours. The reaction mixture was cooled to room temperature, then concentrated, and azeotroped with toluene. To the obtained reside was added diethyl ether, followed by stirring at room temperature for 0.5 hours. The precipitate was collected by filtration and washed with diethyl ether to obtain 3.23 g of powder. The filtrate was concentrated and the residue was treated with diethyl ether in the same manner to obtain 2.22 g of a solid. 3.23 g of the powder and 2.22 g of the solid were combined and washed with diethyl ether to obtain 3.57 g of methyl 2,3-dichloro-7-methylquinoxaline-6-carboxylate.

Preparation Example 8

To a suspension of 3.57 g of methyl 2,3-dichloro-7-methylquinoxaline-6-carboxylate in 214 mL of methanol were added 7.0 mL of pyridine and 2.34 mL of hydrazine monohydrate at 0° C., and then the mixture was stirred at room temperature overnight. The mixture was concentrated until the total amount became about 100 mL, and water was added thereto, followed by stirring at room temperature for 1 hour. The precipitate was collected by filtration, washed with water and ethanol, and dried under reduced pressure to obtain 2.94 g of methyl 3-chloro-2-hydrazino7-methylquinoxaline-6-carboxylate.

Preparation Example 9

To a mixture of 1.75 g of methyl 4-fluoro-2-(methoxymethyl)benzoate and 8.7 mL of concentrated sulfuric acid was added 964 mg of potassium nitrate over 5 minutes under cooling at −10° C. After stirring at the same temperature for 4 hours and a half, the reaction mixture was added to 300 mL of ice water, followed by stirring. The solid was collected by filtration, washed with water, and dried under reduced pressure to obtain 1.87 g of methyl 4-fluoro-2-(methoxymethyl)-5-nitrobenzoate.

Preparation Example 10

To a mixture of 6.0 g of methyl 4-fluoro-2-(methoxymethyl)-5-nitrobenzoate, 3.5 g of 2-(tetrahydrofuran-3-yl)-1H-imidazole, and 60 mL of acetonitrile was added 6.9 mL of triethylamine, followed by stirring at 70° C. for 5.5 hours. The reaction mixture was concentrated, and water and ethyl acetate were added thereto, followed by extraction with ethyl acetate. The organic layer was washed with saturated brine and then dried over anhydrous magnesium sulfate, and the solvent was evaporated under reduced pressure. The obtained residue was purified by silica gel column chromatography (chloroform/methanol) to obtain 6.65 g of methyl 2-(methoxymethyl)-5-nitro-4-[2-(tetrahydrofuran-3-yl)-1H-imidazol-1-yl]benzoate.

Preparation Example 11

A mixture of 6.00 g of methyl 5-amino-2-(methoxymethyl)-4-[2-(tetrahydrofuran-3-yl)-1H-imidazol-1-yl]benzoate, 5.87 g of 1,1'-carbonyldiimidazole, and 30 mL of 1,2-dichlorobenzene was stirred at 120° C. for 3 hours. After air-cooling, the precipitate was collected by filtration. The obtained solid was washed with methanol and air-dried to obtain 4.54 g of methyl 8-(methoxymethyl)-4-oxo-1-(tetrahydrofuran-3-yl)-4,5-dihydroimidazo[1,5-a]quinoxaline-7-carboxylate.

Preparation Example 12

To a solution of 2.5 mL of tetrahydrofuran-3-carboxyaldehyde (50% aqueous solution) in 40 mL of ethanol were added 2.6 mL of a 40% aqueous glyoxal solution and 14 mL of 28% aqueous ammonia in this order under ice-cooling, followed by stirring for 3.5 hours while gradually warming to room temperature. Ethanol was evaporated under reduced pressure, and sodium chloride was added to an aqueous solution of the residue to saturate, followed by extraction with chloroform. The organic layer was dried over anhydrous magnesium sulfate and the solvent was evaporated under reduced pressure. The obtained residue was heated and dissolved in ethyl acetate, and left to be cooled. The precipitated solid was collected by filtration to obtain 1.58 g of 2-(tetrahydrofuran-3-yl)-1H-imidazole as a white solid.

Preparation Example 13

To a mixture of 6.65 g of methyl 2-(methoxymethyl)-5-nitro-4-[2-(tetrahydrofuran-3-yl)-1H-imidazol-1-yl]benzoate, 980 mg of ammonium chloride, 33.0 mL of tetrahydrofuran, 66.0 mL of methanol, and 33.0 mL of water was added 4.8 g of reduced iron, followed by stirring at 70° C. for 4.5 hours. The insoluble matter was filtered through celite. The filtrate was concentrated, and water and ethyl acetate were added thereto, followed by extraction with ethyl acetate. The organic layer was washed with saturated brine and then dried over anhydrous magnesium sulfate, and the solvent was evaporated under reduced pressure. The obtained residue was purified by silica gel column chromatography (chloroform/methanol) to obtain 5.30 g of methyl 5-amino-2-(methoxymethyl)-4-[2-(tetrahydrofuran-3-yl)-1H-imidazol-1-yl]benzoate as a brown solid.

Preparation Example 14

To a mixture of 3 g of methyl 4-fluoro-2-methoxy-5-nitrobenzoate, 1.99 g of 2-(tetrahydro-2H-pyran-4-yl)-1H-imidazole, and 15 mL of N-ethylpyrrolidone was added 3.6 g of potassium carbonate, followed by stirring at 100° C. for 3 hours. To the reaction mixture were added water and ethyl acetate, followed by extraction with ethyl acetate. The organic layer was washed with saturated brine and then dried over anhydrous magnesium sulfate, and the solvent was evaporated under reduced pressure. The obtained residue was purified by silica gel column chromatography (chloroform/methanol) to obtain 4.12 g of methyl 2-methoxy-5-nitro-4-[2-(tetrahydro-2H-pyran-4-yl)-1H-imidazol-1-yl]-benzoate.

Preparation Example 15

To a solution of 3.45 g of 1-bromo-4-fluoro-2-(methoxymethyl)benzene in 20 mL of dimethylsulfoxide were sequentially added 353 mg of palladium acetate, 650 mg of 1,3-bis (diphenylphosphino)propane, 4.4 mL of triethylamine, and 10 mL of methanol, and the atmosphere in the reaction container was replaced with carbon monoxide, followed by stirring at 70° C. for 6 hours. The reaction mixture was poured into a mixture of water and ethyl acetate. The aqueous layer was separated, and the organic layer was washed with saturated brine and then dried over anhydrous magnesium sulfate. The solvent was evaporated under reduced pressure. The obtained residue was purified by silica gel column chromatography (n-hexane/ethyl acetate) to obtain 1.75 g of methyl 4-fluoro-2-(methoxymethyl)benzoate.

Preparation Example 16

To a solution of 3 g of methyl 4-fluoro-2-hydroxybenzoate in 60 mL of tetrahydrofuran were added 1.98 g of tetrahydrofuran-3-ylmethanol and 4.28 g of tributylphosphine, followed by ice-cooling. To a mixture was gradually added 6.67 g of 1,1'-(azodicarbonyl)dipiperidine, followed by stirring for 20 minutes. The mixture was warmed to room temperature, stirred for 16 hours, and then poured into a mixture of water and ethyl acetate. The aqueous layer was separated, the organic layer was washed with saturated brine and then dried over anhydrous magnesium sulfate, and the solvent was evaporated under reduced pressure. The obtained residue was purified by silica gel column chromatography (n-hexane/ethyl acetate) to obtain 3.14 g of methyl 4-fluoro-2-(tetrahydrofuran-3-ylmethoxy)benzoate.

Preparation Example 17

Under a nitrogen atmosphere, to a mixture of 8.6 g of ethyl cis-2-{[tert-butyl(dimethyl)silyl]oxy}cyclopentanecarboxylate and 50 mL of diethyl ether was added dropwise 32 mL of a 1.04 M diisobutylaluminum hydride in n-hexane at −78° C., followed by stirring at the same temperature for 2 hours. To the reaction mixture was added methanol to decompose the excess diisobutylaluminum hydride, followed by warming to room temperature. To the reaction mixture was added an aqueous (+)-potassium sodium tartrate solution, followed by extraction with diethyl ether, the organic layer was washed with saturated brine and dried over anhydrous magnesium sulfate, and then the solvent was evaporated. The obtained residue was purified by silica gel column chromatography (n-hexane/ethyl acetate) to obtain 7.20 g of cis-2-{[tert-butyl(dimethyl)silyl]oxy}cyclopentanecarboxaldehyde as a colorless oil.

Preparation Example 18

To 500 mg of tert-butyl 5-methoxy-2,3-dihydro-1H-pyrrolo[2,3-c]pyridine-1-carboxylate was added 1.5 mL of trifluoroacetic acid, followed by stirring at room temperature for 0.5 hours. The reaction mixture was poured into ice water, neutralized with a 1 M aqueous sodium hydroxide solution, and then chloroform was added to the mixture. The aqueous layer was separated, the organic layer was washed with water and saturated brine, and dried over anhydrous magnesium sulfate, and then the solvent was evaporated under reduced pressure to obtain 262 mg of 5-methoxy-2,3-dihydro-1H-pyrrolo[2,3-c]pyridine as a pale yellow solid.

Preparation Example 19

To a solution of 200 mg of tert-butyl 4-(methoxymethyl)-1,3-dihydro-2H-isoindole-2-carboxylate in 2 mL of ethyl acetate was added 2.3 mL of a 4 M hydrogen chloride-ethyl acetate solution under ice-cooling, followed by stirring at room temperature overnight. Under ice-cooling, to the reaction mixture was added a 1 M aqueous sodium hydroxide solution to adjust the pH to about 7. The aqueous layer was separated, the organic layer was washed with saturated brine and dried over anhydrous magnesium sulfate. The solvent was evaporated under reduced pressure to obtain 100 mg of 4-(methoxymethyl)isoindoline as a brown oil.

Preparation Example 20

Under a nitrogen atmosphere, to a solution of 700 mg of tert-butyl 5-chloro-2-(hydroxymethyl)-2,3-dihydro-1H-indole-1-carboxylate in 14 mL of tetrahydrofuran was added portionwise 197 mg of 60% sodium hydride under ice-cooling, followed by warming to room temperature and stirring for 4 hours. After ice-cooling again, 462 μL of methyl iodide was added dropwise thereto, followed by warming to room temperature and stirring for 2 hours. Water was added thereto, followed by extraction with chloroform, and then the obtained organic layer was washed with a saturated aqueous sodium hydrogen carbonate solution and saturated brine. After drying over anhydrous magnesium sulfate, the solvent was evaporated under reduced pressure, and the obtained residue was purified by silica gel column chromatography (chloroform/methanol) to obtain 230 mg of tert-butyl 5-chloro-2-(methoxymethyl)-2,3-dihydro-1H-indole-1-carboxylate as a brown oil.

Preparation Example 21

To a mixture of 1.17 g of 1-(tert-butoxycarbonyl)-5-chloro-2,3-dihydro-1H-indole-2-carboxylic acid and 23 mL of tetrahydrofuran was added dropwise 15.7 mL of a 1 M solution of a borane-tetrahydrofuran complex in tetrahydrofuran under ice-cooling, followed by warming to room temperature and stirring overnight. After ice-cooling again, 15 mL of 1 M hydrochloric acid was added dropwise thereto, followed by extraction with chloroform. The obtained organic layer was washed with water, a saturated aqueous sodium hydrogen carbonate solution and saturated brine, and dried over anhydrous magnesium sulfate. The solvent was evaporated under reduced pressure to obtain 1.18 g of tert-butyl 5-chloro-2-(hydroxymethyl)-2,3-dihydro-1H-indole-1-carboxylate as a pale yellow solid.

Preparation Example 22

To a mixture of 1 g of 5-chloro-2,3-dihydro-1H-indole-2-carboxylic acid monohydrochloride, 1.03 g of di-tert-butyl dicarbonate and 10 mL of 1,4-dioxane was added 9.4 mL of a 1 M aqueous sodium hydroxide solution, followed by stirring at room temperature overnight. The solvent was evaporated under reduced pressure and then 1 M hydrochloric acid was added thereto to adjust the pH to about 3. Then, chloroform was added to the mixture and the aqueous layer was separated. The obtained organic layer was washed with saturated brine and then dried over anhydrous magnesium sulfate, and the solvent was evaporated under reduced pressure. The obtained residue was purified by silica gel column chromatography (chloroform/methanol) to obtain 1.18 g of 1-(tert-butoxycarbonyl)-5-chloro-2,3-dihydro-1H-indole-2-carboxylic acid as a brown oil.

Preparation Example 23

A mixture of 238 mg of tert-butyl 4-formyl-1,3-dihydro-2H-isoindole-2-carboxylate, 612 mg of sodium triacetoxyborohydride, 963 μL of a 2 M dimethylamine-tetrahydrofuran solution, 12 μL of acetic acid, and 14 mL of 1,2-dichloroethane was stirred at 60° C. overnight. After cooling to room temperature, to the reaction mixture was added a saturated aqueous sodium hydrogen carbonate solution, and chloroform was added and the aqueous layer was separated. The obtained organic layer was washed with saturated brine and then dried over anhydrous magnesium sulfate, and the solvent was evaporated under reduced pressure. The obtained residue was purified by silica gel column chromatography (n-hexane/ethyl acetate) to obtain 123 mg of tert-butyl 4-[(dimethylamino)methyl]-1,3-dihydro-2H-isoindole-2-carboxylate as an orange oil.

Preparation Example 24

To a solution of 350 mg of tert-butyl 4-formyl-1,3-dihydro-2H-isoindole-2-carboxylate in 11 mL of methanol was added 134 mg of sodium borohydride under ice-cooling, followed by stirring at room temperature overnight. To the reaction mixture were added water and ethyl acetate and the aqueous layer was separated. The obtained organic layer was washed with saturated brine and then dried over anhydrous magnesium sulfate. The solvent was evaporated under reduced pressure to obtain 213 mg of tert-butyl 4-(hydroxymethyl)-1,3-dihydro-2H-isoindole-2-carboxylate as a yellow oil.

Preparation Example 25

Under an argon atmosphere, to a mixture of 1100 mg of tert-butyl 5-bromo-2,3-dihydro-1H-pyrrolo[2,3-b]pyridine-1-carboxylate, 1062 mg of a 2,4,6-trivinylboroxine/pyridine complex, 1020 mg of potassium carbonate, 3 mL of 1,4-dioxane/water (4/1) was added 215 mg of tetrakis(triphenylphosphine)palladium. The reaction mixture was stirred at 80° C. overnight. To the reaction mixture were added water and ethyl acetate and the aqueous layer was separated. The organic layer was washed with saturated brine and dried over anhydrous magnesium sulfate, and the solvent was evaporated under reduced pressure. The residue was purified by silica gel column chromatography (n-hexane/ethyl acetate) to obtain 783 mg of tert-butyl 5-vinyl-2,3-dihydro-1H-pyrrolo[2,3-b]pyridine-1-carboxylate as a yellow oil.

Preparation Example 26

To a mixture of 4.10 g of methyl 2,4-difluoro-5-nitrobenzoate and 40 mL of acetonitrile was added 4.76 mL of triethylamine, and 2.60 g of 2-(tetrahydro-2H-pyran-4-yl)-1H-imidazole was gradually added thereto under ice-cooling, followed by stirring at room temperature for 4 hours. To the reaction mixture were added water and ethyl acetate, followed by extraction with ethyl acetate, the organic layer was washed with saturated brine and then dried over anhydrous magnesium sulfate, and the solvent was evaporated under reduced pressure. The obtained residue was purified by silica gel column chromatography (chloroform/methanol) to obtain 3.84 g of methyl 2-fluoro-5-nitro-4-[2-(tetrahydro-2H-pyran-4-yl)-1H-imidazol-1-yl]benzoate as a yellow solid.

Preparation Example 27

To a mixture of 10.45 g of methyl 4-fluoro-5-nitro-2-vinylbenzoate and 104.5 mL of pyridine was added 14.69 mL of tert-butylamine, followed by stirring at room temperature overnight. The solvent was evaporated under reduced pressure, and to the residue were added water and ethyl acetate, followed by extraction with ethyl acetate. The organic layer was washed with saturated brine and dried over anhydrous magnesium sulfate, and the solvent was evaporated under reduced pressure to obtain 14 g of methyl 4-(tert-butylamino)-5-nitro-2-vinylbenzoate as a brown oil.

Preparation Example 28

To a mixture of 3.74 g of methyl 4-(tert-butylamino)-5-nitro-2-vinylbenzoate and 37.4 mL of methanol was added 21.7 mL of 6 M hydrochloric acid, followed by heating to reflux for 1 hour. The reaction mixture was cooled to room temperature and the precipitated solid was collected by filtration. The obtained solid was dried at 40° C. for 2 hours under reduced pressure to obtain 2.56 g of methyl 4-amino-5-nitro-2-vinylbenzoate monohydrochloride as a yellow solid.

In the same manner as the method of Preparation Example 2, the compounds of Preparation Examples 2-1 to 2-15 were prepared, in the same manner as the method of Preparation Example 3, the compounds of Preparation Examples 3-1 to 3-7 were prepared, in the same manner as the method of Preparation Example 4, the compounds of Preparation Examples 4-1 to 4-7 were prepared, in the same manner as the method of Preparation Example 5, the compounds of Preparation Examples 5-1 to 5-9 were prepared, in the same manner as the method of Preparation Example 6, the compounds of Preparation Examples 6-1 to 6-2 were prepared, in the same manner as the method of Preparation Example 7, the compounds of Preparation Examples 7-1 to 7-2 were prepared, in the same manner as the method of Preparation Example 8, the compounds of Preparation Examples 8-1 to 8-2 were prepared, in the same manner as the method of Preparation Example 9, the compounds of Preparation Examples 9-1 to 9-2 were prepared, in the same manner as the method of Preparation Example 10, the compounds of Preparation Examples 10-1 to 10-6 were prepared, in the same manner as the method of Preparation Example 11, the compounds of Preparation Examples 11-1 to 11-8 were prepared, in the same manner as the method of Preparation Example 12, the compounds of Preparation Examples 12-1 to 12-2 were prepared, in the same manner as the method of Preparation Example 13, the compounds of Preparation Examples 13-1 to 13-2 were prepared, in the same manner as the method of Preparation Example 18, the compound of Preparation Example 18-1 was prepared, in the same manner as the method of Preparation Example 19, the compounds of Preparation Examples 19-1 to 19-3 were prepared, in the same manner as the method of Preparation Example 20, the compound of Preparation Example 20-1 was prepared, in the same manner as the method of Preparation Example 21, the compound of Preparation Example 21-1 was prepared, in the same manner as the method of Preparation Example 25, the compounds of Preparation Examples 25-1 to 25-2 were prepared, in the same manner as the method of Preparation Example 27, the compound of Preparation Example 27-1 was prepared, in the same manner as the method of Preparation Example 28, the compound of Preparation Example 28-1 was prepared, in the same manner as the method of Example 6 as described later, the compound of Preparation Example 29 was prepared, in the same manner as the method of Example 3 as described later, the compound of Preparation Example 30 was prepared, each of which was prepared using the corresponding starting material. The structures and the physicochemical data of Preparation Example compounds are shown in Tables 1 to 19 below.

Example 1

To a mixture of 150 mg of 4-oxo-8-(tetrahydrofuran-3-ylmethoxy)-1-(tetrahydro-2H-pyran-4-yl)-4,5-dihydroimidazo[1,5-a]quinoxaline-7-carboxylic acid and 3 mL of N,N-dimethyl formamide were sequentially added 122 mg of 5-bromo-2,3-dihydro-1H-pyrrolo[2,3-b]pyridine, 0.25 mL of N,N-diisopropylethylamine, and 220 mg of HATU, followed by stirring at room temperature for 72 hours. The mixture was poured into a cooled saturated aqueous sodium hydrogen carbonate solution, followed by stirring for 30 minutes and extracting with ethyl acetate. The organic layer was washed with saturated brine and dried over anhydrous magnesium sulfate. The solvent was evaporated under reduced pressure, and the residue was purified by silica gel column chromatography (chloroform/methanol=100/0-92/8) to obtain 81 mg of 7-[(5-bromo-2,3-dihydro-1H-pyrrolo[2,3-b]pyridin-1-yl)carbonyl]-8-(tetrahydrofuran-3-ylmethoxy)-1-(tetrahydro-2H-pyran-4-yl)imidazo[1,5-a]quinoxalin-4(5H)-one as a white solid.

Example 2

To a mixture of 106 mg of 8-fluoro-4-oxo-1-(tetrahydro-2H-pyran-4-yl)-4,5-dihydroimidazo[1,5-a]quinoxaline-7-carboxylic acid, 53 mg of 5-methoxy-2,3-dihydro-1H-pyrrolo[2,3-c]pyridine, 0.22 mL of N,N-diisopropylethylamine, and 2 mL of N,N-dimethyl formamide was added 146 mg of O-(benzotriazol-1-yl)-N,N,N',N'-tetramethyluronium hexafluorophosphate, followed by stirring at room temperature overnight. To the reaction mixture was added a saturated aqueous sodium hydrogen carbonate solution, followed by extraction with chloroform. The organic layer was washed with saturated brine and dried over anhydrous magnesium sulfate, and then the solvent was evaporated under reduced pressure. The obtained residue was purified by preparative HPLC (methanol/0.1% aqueous formic acid solution) to obtain 5.9 mg of 8-fluoro-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one as a pale brown solid.

Example 3

To a mixture of 200 mg of 8-methyl-4-oxo-1-(tetrahydro-2H-pyran-3-yl)-4,5-dihydroimidazo[1,5-a]quinoxaline-7-carboxylic acid, 100 mg of 5-methoxy-2,3-dihydro-1H-pyrrolo[2,3-c]pyridine, 0.42 mL of N,N-diisopropylethylamine, and 5 mL of N,N-dimethyl formamide was added 235 mg of TBTU, followed by stirring at room temperature overnight. To the reaction mixture were added water and a saturated aqueous sodium hydrogen carbonate solution, followed by extraction with chloroform. The organic layer was washed with saturated brine and dried over anhydrous magnesium sulfate, and then the solvent was evaporated under reduced pressure. The obtained residue was purified by silica gel column chromatography (chloroform/methanol=100/0-95/5). The obtained solid was washed with methanol to obtain 148 mg of 7-[(5-methoxy-2,3-dihydro-1H-pyrrolo[2,3-c]pyridin-1-yl)carbonyl]-8-methyl-1-(tetrahydro-2H-pyran-3-yl)imidazo[1,5-a]quinoxalin-4(5H)-one.

Example 4

373 mg of 7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one was purified by preparative HPLC (flow rate: 8 mL/min, acetonitrile/water=30/70) using CHIRALCEL (registered trademark) OJ-RH column, 5 μm, 20×150 mm (Daicel Chemical Industries, Ltd.). As a compound with a short retention time (retention time: 9.32 min), 125 mg of (−)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one was obtained, and as a compound with a long retention time (retention time: 13.31 min), 132 mg of (+)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one was obtained. To a mixture of 125 mg of (−)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one, which was a compound with a short retention time, 5 mL of methanol and 7.4 mL of tetrahydrofuran was added 230 μL of a 4 M hydrogen chloride-ethyl acetate solution, followed by stirring at room temperature for 30 minutes. The solvent was evaporated under reduced pressure, to the obtained residue was added 2 mL of diethyl ether, and the suspension was stirred for 30 minutes. The solid was collected by filtration and dried under reduced pressure to obtain 128 mg of (−)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one dihydrochloride, which was a compound with a short retention time, as a white solid. To a mixture of 132 mg of (+)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one, which was a compound with a long retention time, 5 mL of methanol and 7.4 mL of tetrahydrofuran was added 243 μL of a 4 M hydrogen chloride-ethyl acetate solution, followed by stirring at room temperature for 30 minutes. The solvent was evaporated under reduced pressure, to the obtained residue was added 2 mL of diethyl ether, and the suspension was stirred for 30 minutes. The solid was collected by filtration and dried under reduced pressure to obtain 125 mg of (+)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one dihydrochloride, which was a compound with a long retention time, as a white solid.

Further, in the tables, the compounds with short column retention times are denoted as (a) and the compounds with long column retention times are denoted as (b).

In addition, Example 25(a), Example 27(a), Example 29(a), Example 30(a), Example 39(a), Example 40(a), Example 43(a) and Example 45(a) showed negative specific rotations, and Example 25(b), Example 27(b), Example 29(b), Example 30(b), Example 39(b), Example 40(b), Example 43(b) and Example 45(b) showed positive specific rotations.

Example 5

To a mixture of 369 mg of 7-[(5-bromo-2,3-dihydro-1H-pyrrolo[2,3-b]pyridin-1-yl)carbonyl]-1-(cis-2-{[tert-butyl(dimethyl)silyl]oxy}cyclopentyl)-8-methylimidazo[1,5-a]quinoxalin-4(5H)-one and 3.70 mL of methanol was added 0.15 mL of concentrated hydrochloric acid, followed by stirring at room temperature for 3 days. The solvent was evaporated under reduced pressure, then the residue was dissolved in water, and a saturated aqueous sodium hydrogen carbonate solution was added thereto to adjust the pH to about 8. The mixture was extracted with chloroform, the organic layer was dried over anhydrous magnesium sulfate, and then the solvent was evaporated under reduced pressure. The obtained residue was purified by silica gel column chromatography (chloroform/methanol=100/0-95/5) and triturated with methanol to obtain 221 mg of 7-[(5-bromo-2,3-dihydro-1H-pyrrolo[2,3-b]pyridin-1-yl)carbonyl]-1-(cis-2-hydroxycyclopentyl)-8-methylimidazo[1,5-a]quinoxalin-4(5H)-one as a colorless solid.

Example 6

96 mg of 1-(cyclopropylmethyl)-8-methyl-4-oxo-4,5-dihydro[1,2,4]triazolo[4,3-a]quinoxaline-7-carboxylic acid, 52 mg of 5-ethyl-2,3-dihydro-1H-pyrrolo[2,3-b]pyridine, 336 µL of N,N-diisopropylethylamine, and 145 mg of TBTU were added to 1.6 mL of N-methylpyrrolidone, and reacted at 120° C. for 1 hour using a microwave reactor. To the reaction mixture was added a saturated aqueous sodium hydrogen carbonate solution, followed by extraction with ethyl acetate. The organic layer was washed with saturated brine and dried over anhydrous magnesium sulfate, the solvent was evaporated under reduced pressure, and the obtained residue was purified by silica gel column chromatography (chloroform/methanol=100/0-97/3) to obtain 120 mg of a white solid. To a mixture of the obtained white solid and 2 mL of methanol was added 277 µL of a 4 M hydrogen chloride-ethyl acetate solution, followed by stirring at room temperature overnight. The precipitated solid was collected by filtration and dried under reduced pressure to obtain 95 mg of 1-(cyclopropylmethyl)-7-[(5-ethyl-2,3-dihydro-1'-pyrrolo[2,3-b]pyridin-1-yl)carbonyl]-8-methyl[1,2,4]triazolo[4,3-a]quinoxalin-4(5H)-one dihydrochloride as a white solid.

In the same manner as in the methods of Examples 1 to 6, the compounds of Examples 7 to 48 shown in Tables below were prepared. For the Example compounds, the structures and the preparation methods are shown in Tables 20 to 32, and the physicochemical data are shown in Tables 33 to 40. In addition, the structures of other compounds of the compounds of the formula (I) are shown in Tables 41 to 46. These can be easily prepared by any of the preparation methods above, the methods described in Examples, the methods apparent to those skilled in the art, or modified methods thereof.

TABLE 1

| Pr | Structure | Data |
|----|-----------|------|
| 1  |           | ESI−: 327.2 |
| 2  | 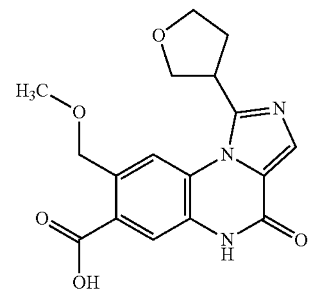 [SMILES: COCc1cc2c(cc1C(=O)O)[nH]c(=O)c1cnc(C3CCOC3)n12]          | ESI+: 344.1 |
| 2-1 | 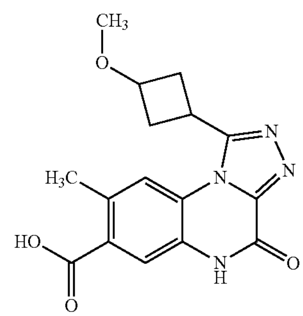 [SMILES: COC1CC(c2nnc3c(=O)[nH]c4cc(C(=O)O)c(C)cc4n23)C1]         | ESI+: 329.1 |
| 2-2 | 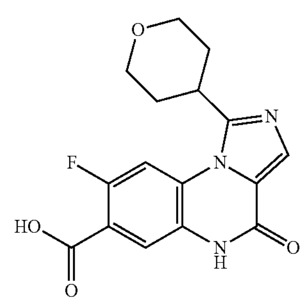 [SMILES: O=C(O)c1cc2[nH]c(=O)c3cnc(C4CCOCC4)n3c2cc1F]         | ESI+: 331.9 |

TABLE 2

| Pr | Structure | Data |
|----|-----------|------|
| 2-3 | 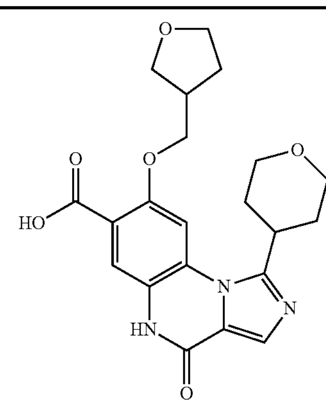         | ESI+: 414.3 |

TABLE 2-continued

| Pr | Structure | Data |
|---|---|---|
| 2-4 | 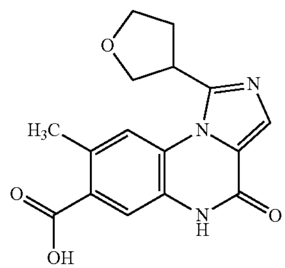 [SMILES: Cc1cc2c(cc1C(=O)O)[nH]c(=O)c1cnc(C3CCOC3)n12] | APCI/ESI+: 314.1 |
| 2-5 | 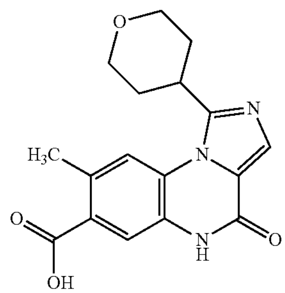 [SMILES: Cc1cc2c(cc1C(=O)O)[nH]c(=O)c1cnc(C3CCOCC3)n12] | ESI−: 326.1 |
| 2-6 | 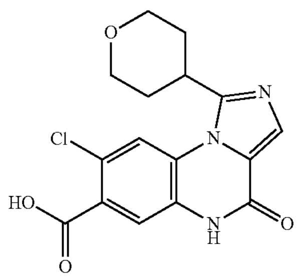 [SMILES: O=C(O)c1cc2[nH]c(=O)c3cnc(C4CCOCC4)n3c2cc1Cl] | ESI+: 348.1, 350.1 |
| 2-7 | 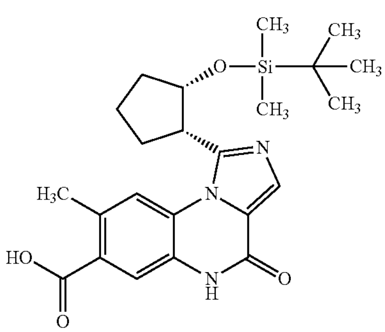 [SMILES: Cc1cc2c(cc1C(=O)O)[nH]c(=O)c1cnc([C@@H]3CCC[C@@H]3O[Si](C)(C)C(C)(C)C)n12] | ESI+: 442.3 |

TABLE 3

| Pr | Structure | Data |
|---|---|---|
| 2-8 | 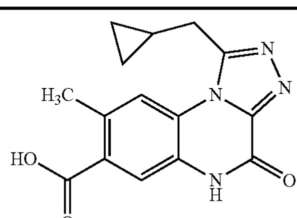 | ESI+: 299 |

TABLE 3-continued

| Pr | Structure | Data |
|---|---|---|
| 2-9 | 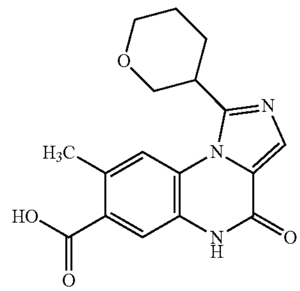 [SMILES: Cc1cc2c(cc1C(=O)O)[nH]c(=O)c1cnc(C3CCCOC3)n12] | ESI+: 328 |
| 2-10 | 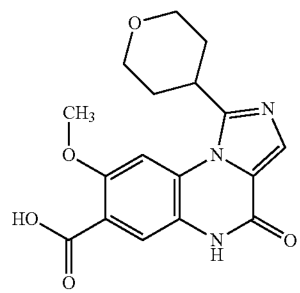 [SMILES: COc1cc2c(cc1C(=O)O)[nH]c(=O)c1cnc(C3CCOCC3)n12] | ESI+: 344 |
| 2-11 | 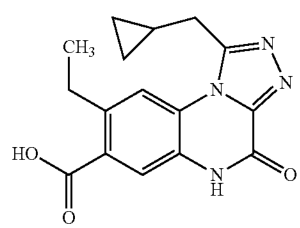 [SMILES: CCc1cc2c(cc1C(=O)O)[nH]c(=O)c1nnc(CC3CC3)n12] | ESI+: 313.0 |
| 2-12 | 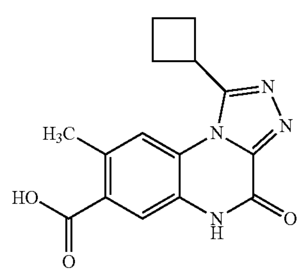 [SMILES: Cc1cc2c(cc1C(=O)O)[nH]c(=O)c1nnc(C3CCC3)n12] | ESI+: 299.1 |
| 2-13 | 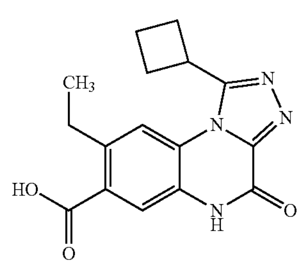 [SMILES: CCc1cc2c(cc1C(=O)O)[nH]c(=O)c1nnc(C3CCC3)n12] | ESI+: 313.0 |

TABLE 4
| Pr | Structure | Data |
|---|---|---|
| 2-14 | 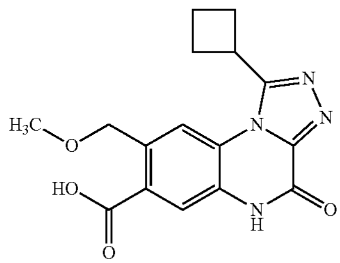 [SMILES: COCc1cc2c(cc1C(=O)O)[nH]c(=O)c1nnc(C3CCC3)n12] | ESI+: 329.1 |
| 2-15 | 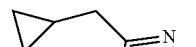 | ESI+: 329.1 |
| 3 | 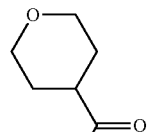 | ESI+: 379, 381 |
| 3-1 | 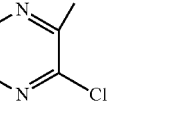 | ESI+: 379.1, 381.1 |
| 3-2 | 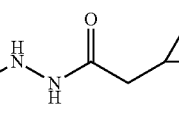 | ESI+: 349, 351 |
| 3-3 | 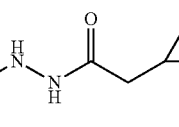 | ESI−: 361.2, 363.2 |

TABLE 5

| Pr | Structure | Data |
|---|---|---|
| 3-4 | 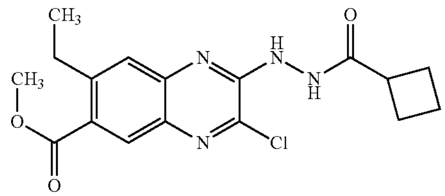 [SMILES: CCc1cc2nc(NNC(=O)C3CCC3)c(Cl)nc2cc1C(=O)OC] | ESI−: 361.1, 363.1 |
| 3-5 | 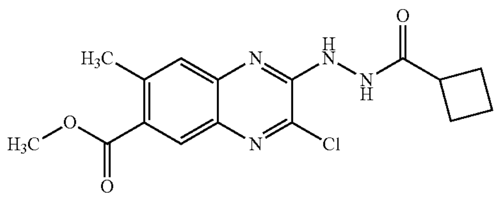 [SMILES: COC(=O)c1cc2nc(Cl)c(NNC(=O)C3CCC3)nc2cc1C] | ESI+: 349, 351 |
| 3-6 | 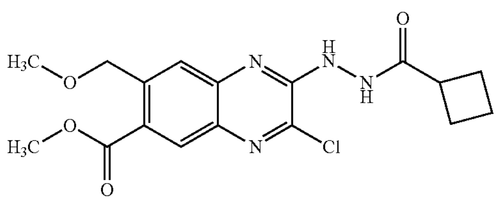 [SMILES: COCc1cc2nc(NNC(=O)C3CCC3)c(Cl)nc2cc1C(=O)OC] | ESI+: 379.0, 381.0 |
| 3-7 | 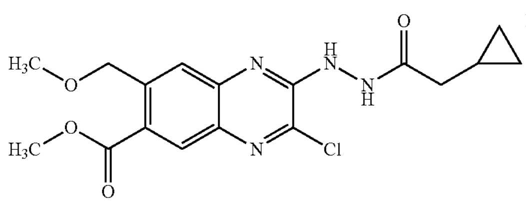 [SMILES: COCc1cc2nc(NNC(=O)CC3CC3)c(Cl)nc2cc1C(=O)OC] | ESI+: 379.0, 389.0 |
| 4 | 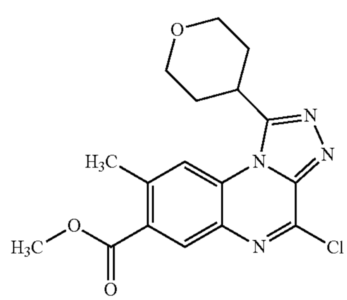 [SMILES: COC(=O)c1cc2nc(Cl)c3nnc(C4CCOCC4)n3c2cc1C] | ESI+: 361.1, 363.0 |
| 4-1 | 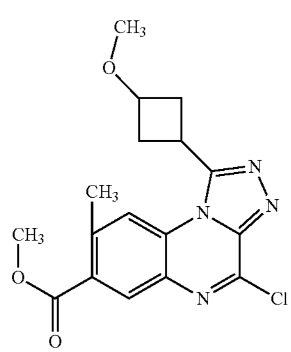 [SMILES: COC(=O)c1cc2nc(Cl)c3nnc(C4CC(OC)C4)n3c2cc1C] | ESI+: 361.1, 363.0 |

TABLE 6
| Pr | Structure | Data |
|---|---|---|
| 4-2 | 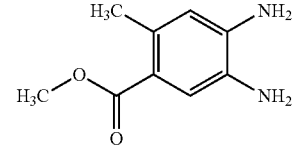 | ESI+: 331, 333 |
| 4-3 | 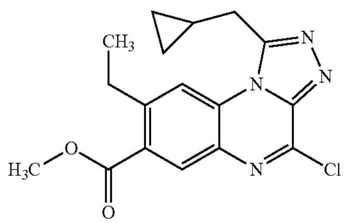 [SMILES: CCc1cc2c(cc1C(=O)OC)nc(Cl)c1nnc(CC3CC3)n12] | ESI+: 367.1, 369.0 (M + Na)+ |
| 4-4 | 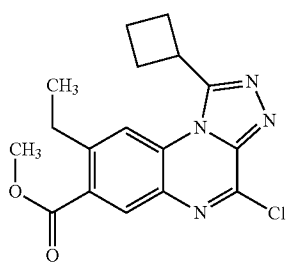 [SMILES: CCc1cc2c(cc1C(=O)OC)nc(Cl)c1nnc(C3CCC3)n12] | ESI+: 345.0, 347.0 |
| 4-5 | 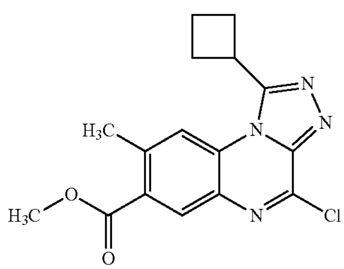 [SMILES: COC(=O)c1cc2nc(Cl)c3nnc(C4CCC4)n3c2cc1C] | ESI+: 331, 333 |
| 4-6 | 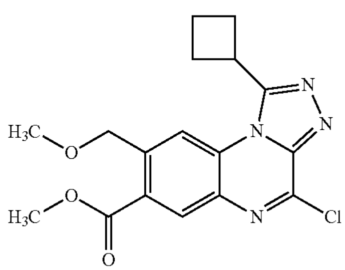 [SMILES: COCc1cc2c(cc1C(=O)OC)nc(Cl)c1nnc(C3CCC3)n12] | ESI+: 360.9, 362.8 |
| 4-7 | 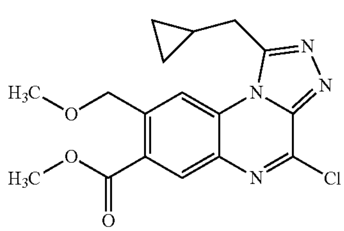 [SMILES: COCc1cc2c(cc1C(=O)OC)nc(Cl)c1nnc(CC3CC3)n12] | ESI+: 360.9, 362.8 |
TABLE 7
| Pr | Structure | Data |
|---|---|---|
| 5 | 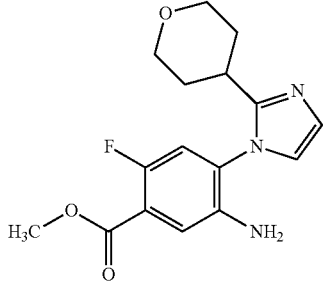 | ESI+: 181.1 |
| 5-1 | 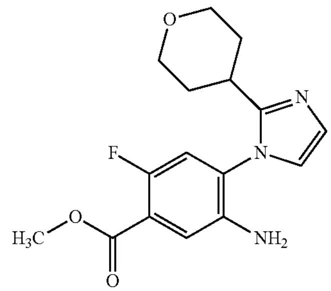 | ESI+: 320.0 |
| 5-2 | 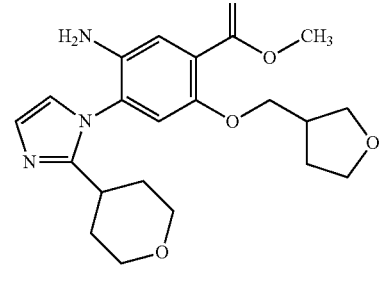 | ESI+: 402.3 |
| 5-3 | 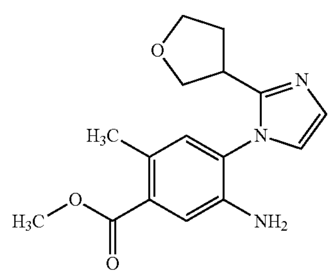 [SMILES: COC(=O)c1cc(N)c(-n2ccnc2C2CCOC2)cc1C] | APCI/ESI+: 302.2 |
| 5-4 | 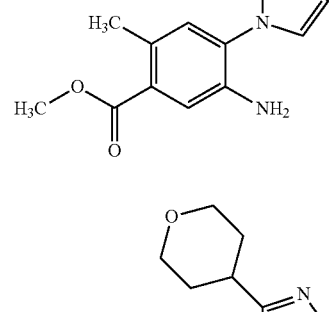 | ESI+: 316.1 |

TABLE 8

| Pr | Structure | Data |
|---|---|---|
| 5-5 | 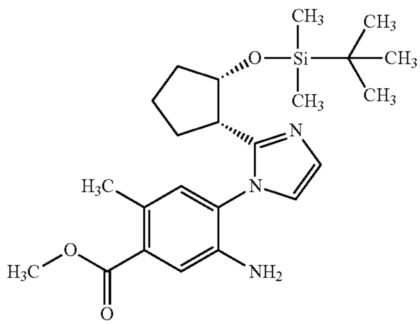 [SMILES: COC(=O)c1cc(N)c(-n2ccnc2[C@@H]2CCC[C@@H]2O[Si](C)(C)C(C)(C)C)cc1C] | ESI+: 430 |
| 5-6 | 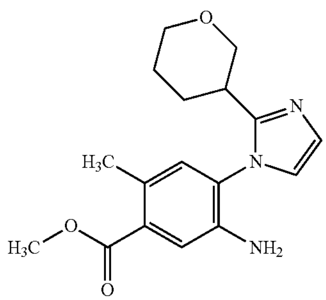 | ESI+: 316 |
| 5-7 | 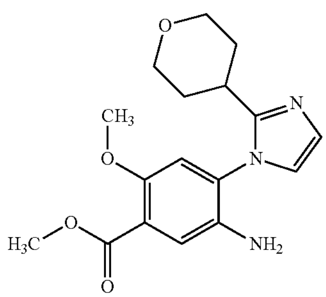 [SMILES: COC(=O)c1cc(N)c(-n2ccnc2C2CCOCC2)cc1OC] | ESI+: 332 |
| 5-8 | 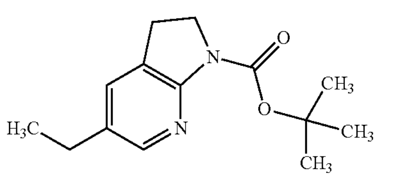 [SMILES: CCc1cnc2c(c1)CCN2C(=O)OC(C)(C)C] | ESI+: 249.2 |
| 5-9 | 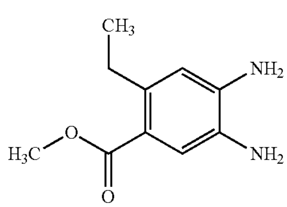 | ESI+: 195.3 |

TABLE 9

| Pr | Structure | Data |
|---|---|---|
| 6 | | FAB+: 235.1 |
| 6-1 | 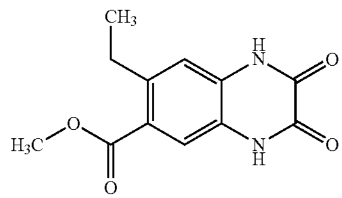 [SMILES: CCc1cc2[nH]c(=O)c(=O)[nH]c2cc1C(=O)OC] | ESI−: 247.2 |
| 6-2 | 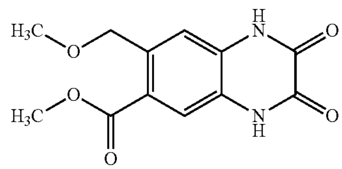 [SMILES: COCc1cc2[nH]c(=O)c(=O)[nH]c2cc1C(=O)OC] | NMR-DMSO-d6: 3.32-3.44 (3H, m), 3.82 (3H, s), 4.71 (2H, s), 7.37 (1H, s), 7.70 (1H, s), 11.98 (1H, s), 12.09 (1H, s) |
| 7 | 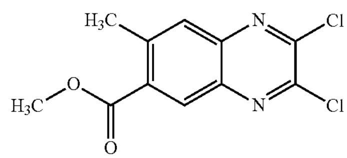 [SMILES: COC(=O)c1cc2nc(Cl)c(Cl)nc2cc1C] | EI+: 270.0, 272.0 |
| 7-1 | 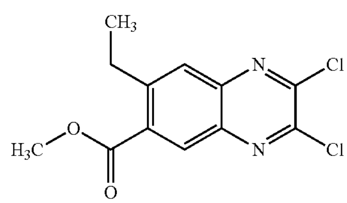 [SMILES: CCc1cc2nc(Cl)c(Cl)nc2cc1C(=O)OC] | ESI+: 285.0, 287.0 |
| 7-2 | 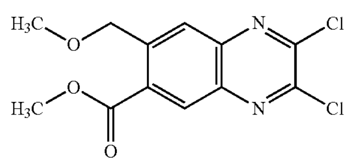 [SMILES: COCc1cc2nc(Cl)c(Cl)nc2cc1C(=O)OC] | ESI+: 301, 303 |
| 8 | 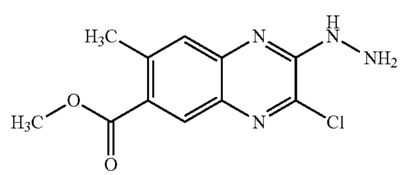 [SMILES: COC(=O)c1cc2nc(Cl)c(NN)nc2cc1C] | ESI+: 267.0, 269.0 |
| 8-1 | 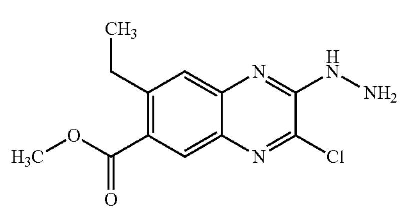 [SMILES: CCc1cc2nc(NN)c(Cl)nc2cc1C(=O)OC] | ESI+: 281.1, 283.0 |

TABLE 10

| Pr | Structure | Data |
|---|---|---|
| 8-2 | (structure) | ESI+: 297, 299 |
| 9 | (structure) | ESI+: 266 (M+Na)+ |
| 9-1 | (structure) | ESI+: 300.1 |
| 9-2 | (structure) | ESI+: 214.0 |
| 10 | (structure) | ESI+: 362.1 |
| 10-1 | (structure) | ESI+: 432.3 |

TABLE 11

| Pr | Structure | Data |
|---|---|---|
| 10-2 | (structure) | APCI/ESI+: 332.1 |
| 10-3 | (structure) | ESI+: 346.0 |
| 10-4 | (structure) | ESI+: 366.2, 368.2 |
| 10-5 | (structure) | ESI+: 460.2 |
| 10-6 | (structure) | ESI+: 346 |

TABLE 12

| Pr | Structure | Data |
|---|---|---|
| 11 | (structure) | ESI+: 358.1 |
| 11-1 | (structure) | ESI+: 346.0 |
| 11-2 | (structure) | ESI+: 428.3 |
| 11-3 | (structure) | APCI/ESI+: 328.2 |

TABLE 13

| Pr | Structure | Data |
|---|---|---|
| 11-4 | (structure) | ESI+: 342.3 |
| 11-5 | (structure) | ESI+: 362.1, 364.1 |
| 11-6 | (structure) | ESI+: 456.3 |
| 11-7 | (structure) | ESI+: 342 |
| 11-8 | (structure) | ESI+: 358 |

TABLE 14
| Pr | Structure | Data |
|---|---|---|
| 12 | 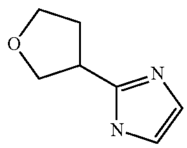 | ESI+: 139.1 |
| 12-1 | 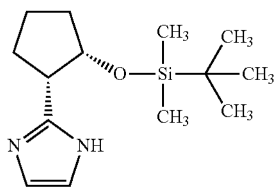 [SMILES: CC(C)(C)[Si](C)(C)O[C@H]1CCC[C@H]1c1ncc[nH]1] | ESI+: 267.2 |
| 12-2 | 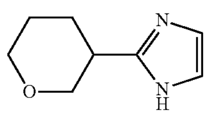 [SMILES: c1c[nH]c(C2CCCOC2)n1] | ESI+: 153 |
| 13 | 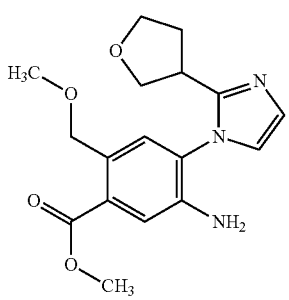 | ESI+: 332.1 |
| 13-1 | 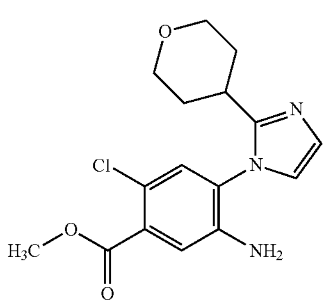 [SMILES: COC(=O)c1cc(N)c(-n2ccnc2C2CCOCC2)cc1Cl] | ESI+: 336.2, 338.2 |
| 13-2 | 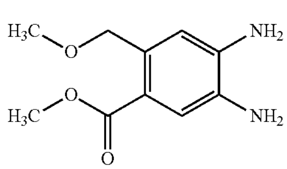 | ESI+: 211 |
TABLE 15
| Pr | Structure | Data |
|---|---|---|
| 14 | 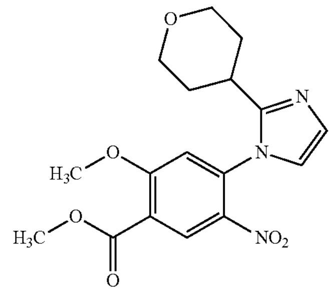 [SMILES: COC(=O)c1cc([N+](=O)[O-])c(-n2ccnc2C2CCOCC2)cc1OC] | ESI+: 362 |
| 15 | 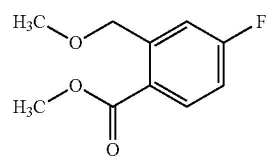 | NMR-CDCl3: 3.49 (3H, s), 3.88 (3H, s), 4.85 (2H, s), 6.9-7.05 (1H, m), 7.41 (1H, dd, J = 10, 3 Hz), 8.0 (1H, dd, J = 9, 6 Hz) |
| 16 | 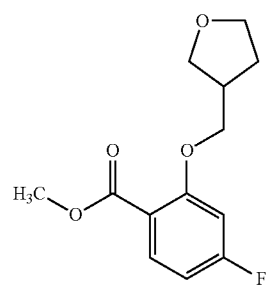 [SMILES: COC(=O)c1ccc(F)cc1OCC1CCOC1] | ESI+: 255.1 |
| 17 | 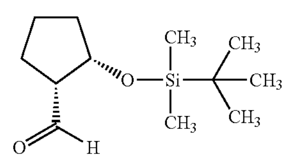 | EI+: 229.1[M + H]+ |
| 18 | 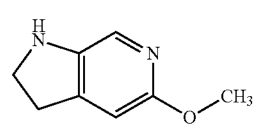 | ESI+: 151.1 |
| 18-1 | 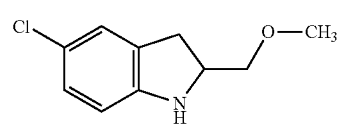 | ESI+: 198.1, 200.1 |
TABLE 16
| Pr | Structure | Data |
|---|---|---|
| 19 | 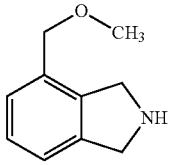 | ESI+: 164.3 |

TABLE 16-continued

| Pr | Structure | Data |
|---|---|---|
| 19-1 | (4-((dimethylamino)methyl)isoindoline) | ESI+: 177.1 |
| 19-2 | (5-ethyl-2,3-dihydro-1H-pyrrolo[2,3-b]pyridine) | ESI+: 149.1 |
| 19-3 | (5-methyl-2,3-dihydro-1H-pyrrolo[2,3-b]pyridine) | ESI+: 135.1 |
| 20 | (tert-butyl 5-chloro-2-(methoxymethyl)indoline-1-carboxylate) | ESI+: 298.1, 300.1 |
| 20-1 | (tert-butyl 4-(methoxymethyl)isoindoline-2-carboxylate) | ESI+: 286 (M + Na)+ |
| 21 | (tert-butyl 5-chloro-2-(hydroxymethyl)indoline-1-carboxylate) | ESI+: 284.0, 286.0 |

TABLE 17

| Pr | Structure | Data |
|---|---|---|
| 21-1 | (5-bromo-3,3-dimethyl-2,3-dihydro-1H-pyrrolo[2,3-b]pyridine) | ESI+: 228.8, 230.1 |

TABLE 17-continued

| Pr | Structure | Data |
|---|---|---|
| 22 | (1-(tert-butoxycarbonyl)-5-chloroindoline-2-carboxylic acid) | ESI+: 298.1, 300.0 |
| 23 | (tert-butyl 4-((dimethylamino)methyl)isoindoline-2-carboxylate) | ESI+: 277.1 |
| 24 | (tert-butyl 4-(hydroxymethyl)isoindoline-2-carboxylate) | ESI+: 250.2 |
| 25 | (tert-butyl 5-vinyl-2,3-dihydro-1H-pyrrolo[2,3-b]pyridine-1-carboxylate) | ESI+: 247.2 |
| 25-1 | (methyl 4-fluoro-5-nitro-2-vinylbenzoate) | ESI+: 226.1 |

TABLE 18

| Pr | Structure | Data |
|---|---|---|
| 25-2 | (tert-butyl 5-methyl-2,3-dihydro-1H-pyrrolo[2,3-b]pyridine-1-carboxylate) | ESI+: 235.2 |

TABLE 18-continued

| Pr | Structure | Data |
|---|---|---|
| 26 | (4-(2-(tetrahydropyran-4-yl)imidazol-1-yl)-2-fluoro-5-nitrobenzoic acid methyl ester) | ESI+: 350.0 |
| 27 | (methyl 2-vinyl-4-(tert-butylamino)-5-nitrobenzoate) | ESI+: 279.1 |
| 27-1 | (methyl 2-(methoxymethyl)-4-(tert-butylamino)-5-nitrobenzoate) | ESI+: 297 |
| 28 | (methyl 2-vinyl-4-amino-5-nitrobenzoate, H·Cl) | ESI+: 223.1 |
| 28-1 | (methyl 2-(methoxymethyl)-4-amino-5-nitrobenzoate) | ESI+: 241 |

TABLE 19

| Pr | Structure | Data |
|---|---|---|
| 29 | (TBS-protected structure with bromopyrrolopyridine) | ESI+: 622.0, 624.0 |
| 30 | (TBS-protected structure with fluoroindoline) | ESI+: 561.1 |

TABLE 20

| Ex | Structure | Syn |
|---|---|---|
| 1 | 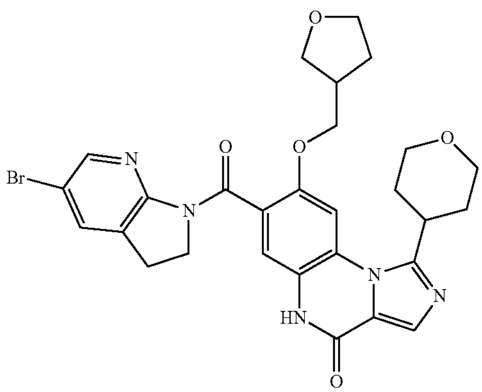 [SMILES: O=C(c1cc2[nH]c(=O)c3cnc(C4CCOCC4)n3c2cc1OCC1CCOC1)N1CCc2cc(Br)cnc21] | 1 |
| 2 | 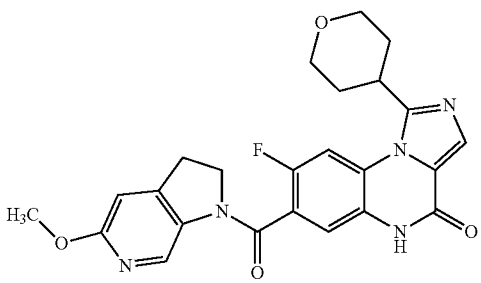 [SMILES: COc1cc2c(cn1)N(C(=O)c1cc3[nH]c(=O)c4cnc(C5CCOCC5)n4c3cc1F)CC2] | 2 |
| 3 | 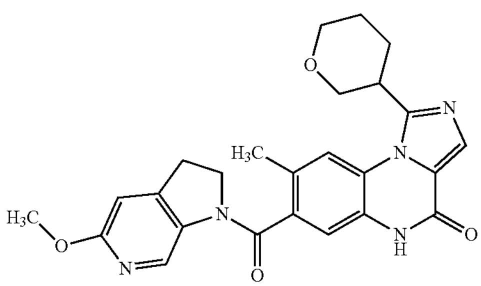 [SMILES: COc1cc2c(cn1)N(C(=O)c1cc3[nH]c(=O)c4cnc(C5CCCOC5)n4c3cc1C)CC2] | 3 |
| 4 (a) | 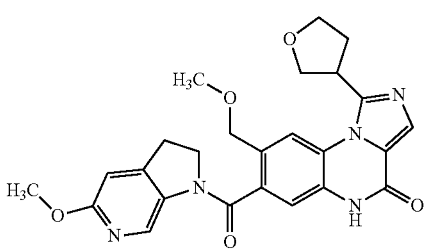 | 3, 4 chiral |
| 4 (b) | 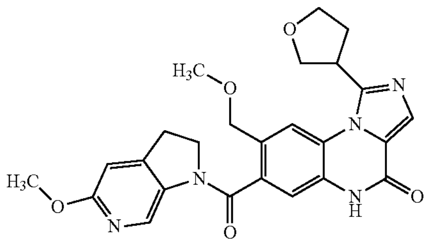 | 3, 4 chiral |

TABLE 21

| Ex | Structure | Syn |
|---|---|---|
| 5 | 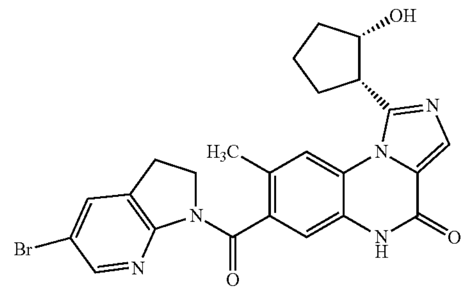 [SMILES: Cc1cc2c(cc1C(=O)N1CCc3cc(Br)cnc31)[nH]c(=O)c1cnc([C@@H]3CCC[C@@H]3O)n12] | 5 |
| 6 | 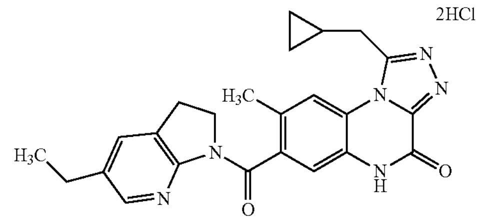 [SMILES: CCc1cnc2c(c1)CCN2C(=O)c1cc2[nH]c(=O)c3nnc(CC4CC4)n3c2cc1C] | 6 |
| 7 | 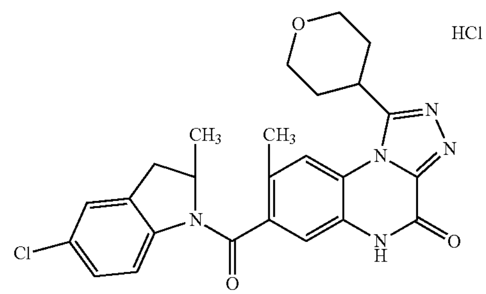 [SMILES: Cc1cc2c(cc1C(=O)N1c3ccc(Cl)cc3CC1C)[nH]c(=O)c1nnc(C3CCOCC3)n12 ; Cl] | 3 |
| 8 | 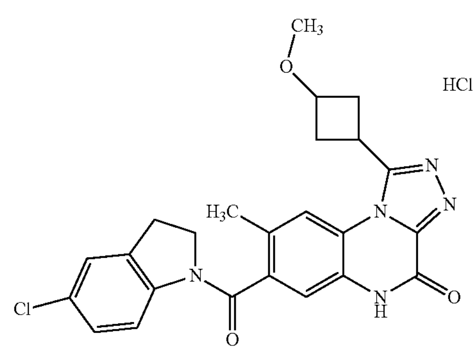 [SMILES: COC1CC(c2nnc3c(=O)[nH]c4cc(C(=O)N5CCc6cc(Cl)ccc65)c(C)cc4n23)C1 ; Cl] | 3 |
| 9 | 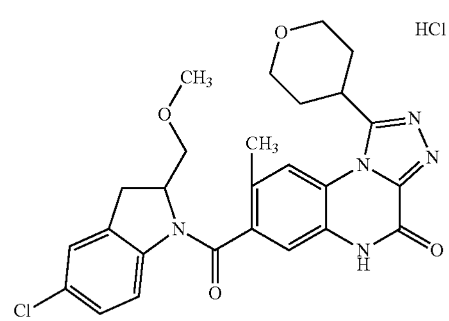 [SMILES: COCC1Cc2cc(Cl)ccc2N1C(=O)c1cc2[nH]c(=O)c3nnc(C4CCOCC4)n3c2cc1C ; Cl] | 3 |

TABLE 22
| Ex | Structure | Syn |
|---|---|---|
| 10 | 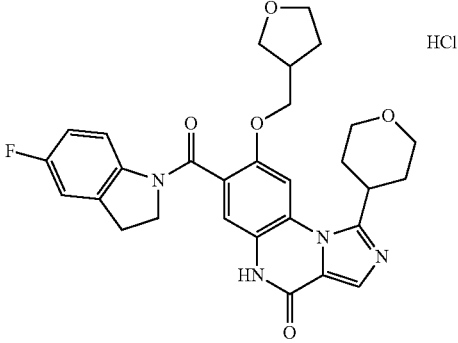 [SMILES: O=C(c1cc2[nH]c(=O)c3cnc(C4CCOCC4)n3c2cc1OCC1CCOC1)N1CCc2cc(F)ccc21 ; Cl] HCl | 3 |
| 11 | 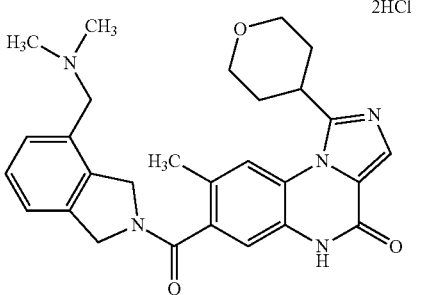 [SMILES: Cc1cc2c(cc1C(=O)N1Cc3cccc(CN(C)C)c3C1)[nH]c(=O)c1cnc(C3CCOCC3)n12] 2HCl | 3 |
| 12 | 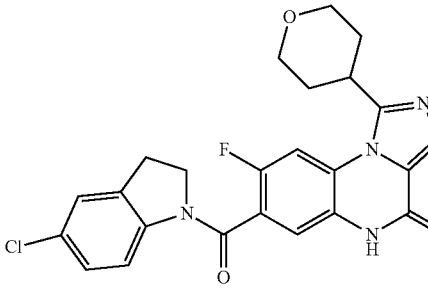 HCl | 3 |
| 13 | 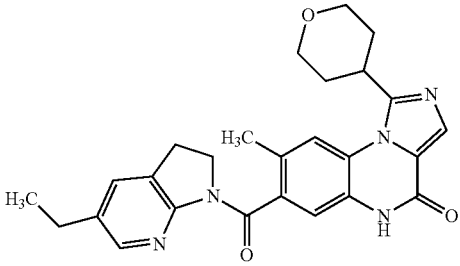 | 6 |
| 14 | 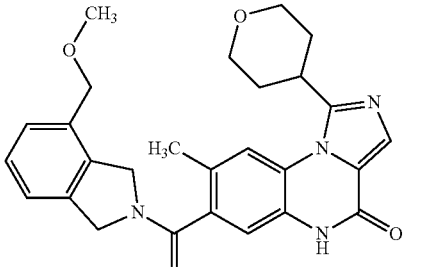 | 3 |
TABLE 23
| Ex | Structure | Syn |
|---|---|---|
| 15 | 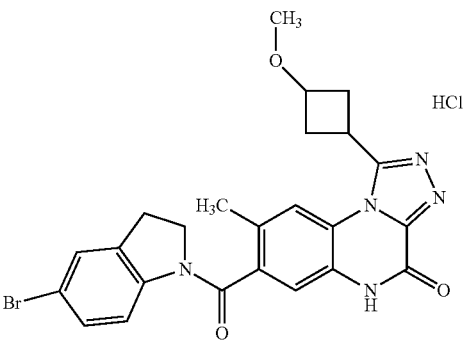 [SMILES: COC1CC(c2nnc3c(=O)[nH]c4cc(C(=O)N5CCc6cc(Br)ccc65)c(C)cc4n23)C1 ; Cl] HCl | 3 |
| 16 | 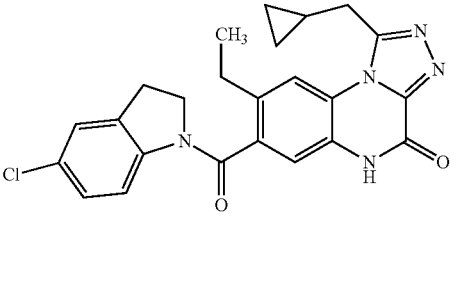 [SMILES: CCc1cc2c(cc1C(=O)N1CCc3cc(Cl)ccc31)[nH]c(=O)c1nnc(CC3CC3)n12] | 6 |
| 17 | 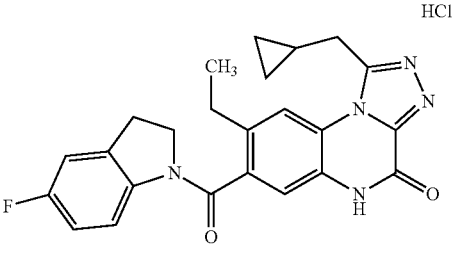 [SMILES: Cl ; CCc1cc2c(cc1C(=O)N1CCc3cc(F)ccc31)[nH]c(=O)c1nnc(CC3CC3)n12] HCl | 6 |
| 18 | 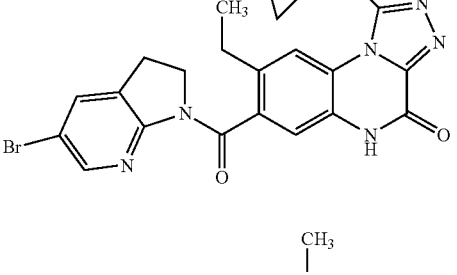 | 6 |
| 19 | 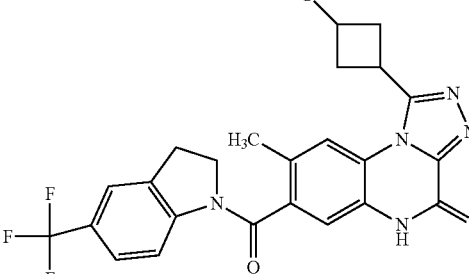 | 6 |

TABLE 24

| Ex | Structure | Syn |
|---|---|---|
| 20 | 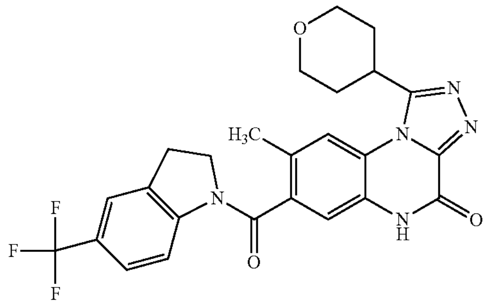 [SMILES: Cc1cc2c(cc1C(=O)N1CCc3cc(C(F)(F)F)ccc31)[nH]c(=O)c1nnc(C3CCOCC3)n12] | 6 |
| 21 | 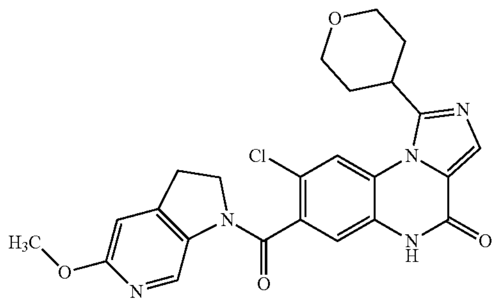 [SMILES: COc1cc2c(cn1)N(C(=O)c1cc3[nH]c(=O)c4cnc(C5CCOCC5)n4c3cc1Cl)CC2] | 3 |
| 22 | 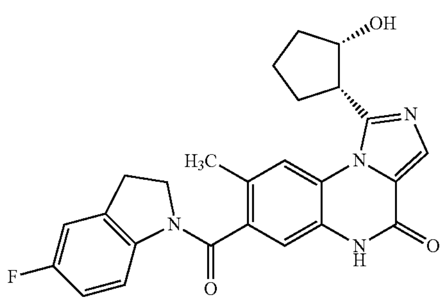 [SMILES: Cc1cc2c(cc1C(=O)N1CCc3cc(F)ccc31)[nH]c(=O)c1cnc([C@@H]3CCC[C@@H]3O)n12] | 5 |
| 23 | 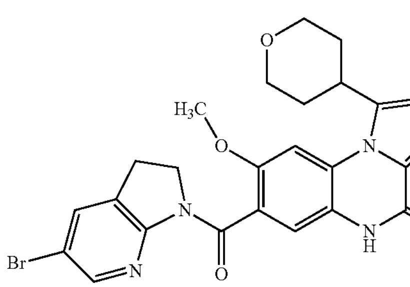 | 6, 2HCl |
| 24 | 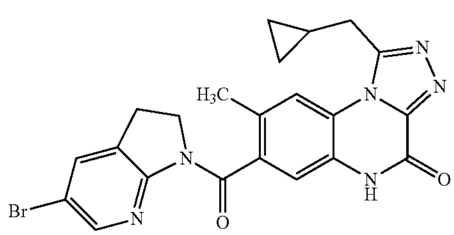 [SMILES: Cc1cc2c(cc1C(=O)N1CCc3cc(Br)cnc31)[nH]c(=O)c1nnc(CC3CC3)n12] | 6 |

TABLE 25

| Ex | Structure | Syn |
|---|---|---|
| 25 (a) | 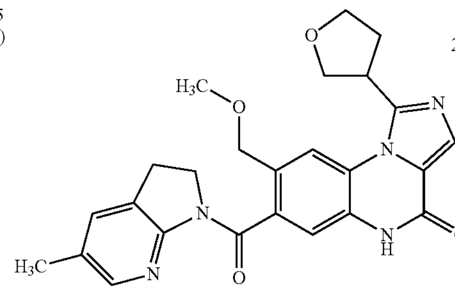 | 3, 4; 2 H—Cl; chiral |
| 25 (b) | 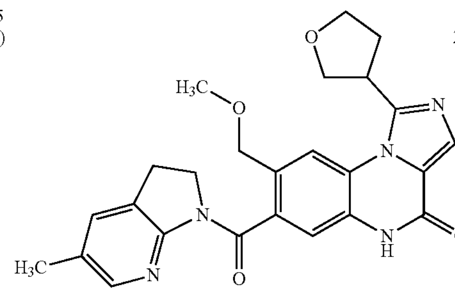 | 3, 4; 2 H—Cl; chiral |
| 26 (a) | 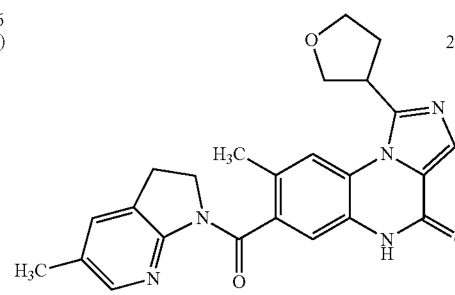 | 6, 4; 2 H—Cl; chiral |
| 26 (b) | 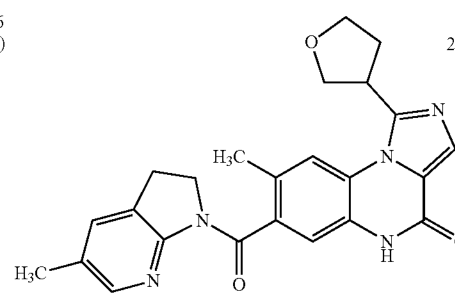 | 6, 4; 2 H—Cl; chiral |
| 27 | 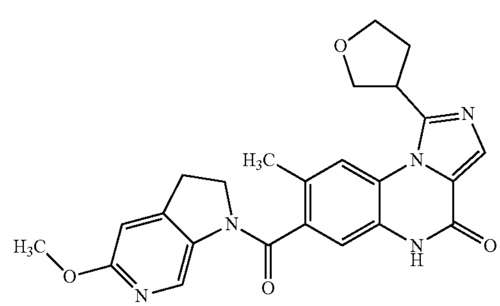 [SMILES: COc1cc2c(cn1)N(C(=O)c1cc3[nH]c(=O)c4cnc(C5CCOC5)n4c3cc1C)CC2] | 6 |

TABLE 26
| Ex | Structure | Syn |
|---|---|---|
| 27 (a) | 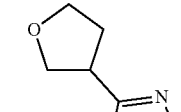 2HCl chiral | 4 |
| 27 (b) | 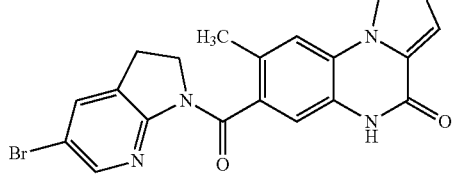 2HCl chiral | 4 |
| 28 | 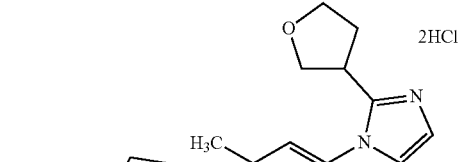 | 6 |
| 28 (a) | 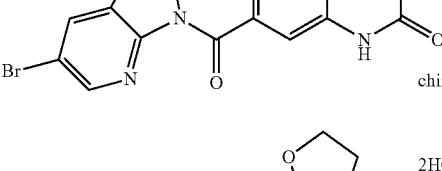 2HCl chiral | 4 |
| 28 (b) | 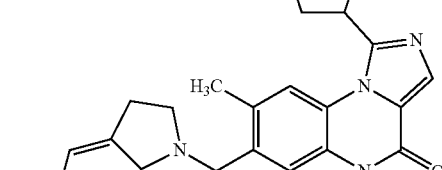 2HCl chiral | 4 |
TABLE 27
| Ex | Structure | Syn |
|---|---|---|
| 29 | 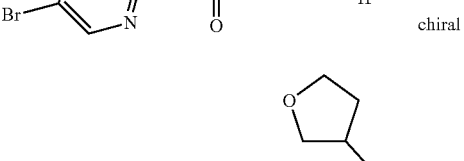 | 6 |
| 29 (a) | 2HCl chiral | 4 |
| 29 (b) | 2HCl chiral | 4 |
| 30 | 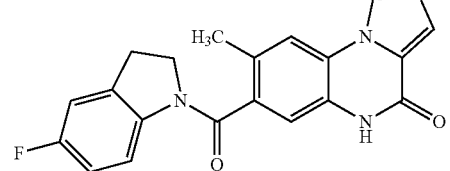 | 3 |
| 30 (a) | 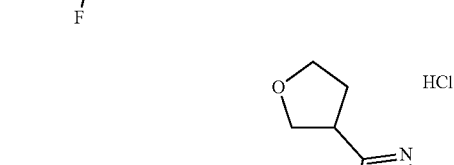 HCl chiral | 4 |

TABLE 28

| Ex | Structure | Syn |
|---|---|---|
| 30 (b) | 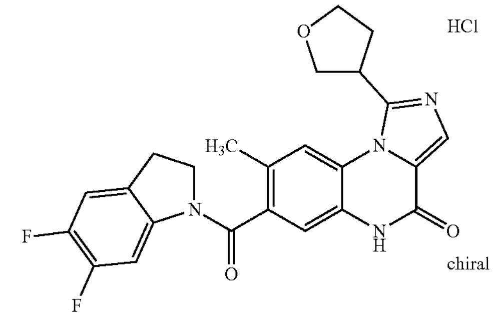 [SMILES: Cc1cc2c(cc1C(=O)N1CCc3cc(F)c(F)cc31)[nH]c(=O)c1cnc(C3CCOC3)n12 ; Cl] | 4 HCl chiral |
| 31 | 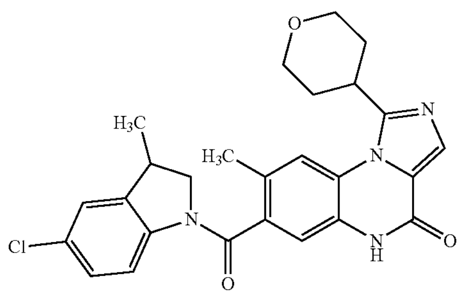 | 3 HCl |
| 32 | 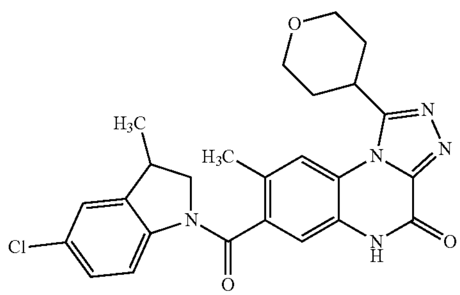 | 3 HCl |
| 33 | 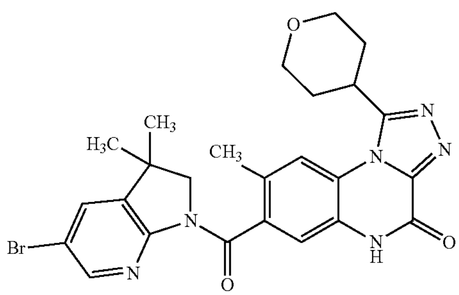 | 3 2HCl |
| 34 | 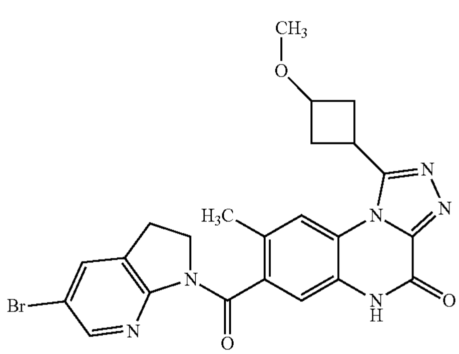 | 6 2HCl |

TABLE 29

| Ex | Structure | Syn |
|---|---|---|
| 35 | 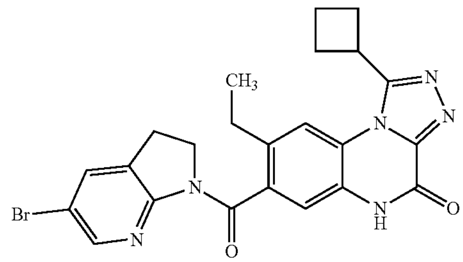 | 6 2HCl |
| 36 | 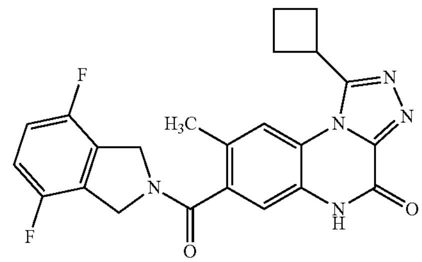 [SMILES: Cc1cc2c(cc1C(=O)N1Cc3c(F)ccc(F)c3C1)[nH]c(=O)c1nnc(C3CCC3)n12] | 3 |
| 37 | 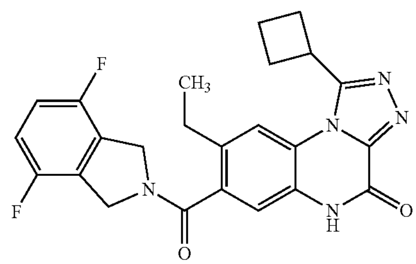 [SMILES: CCc1cc2c(cc1C(=O)N1Cc3c(F)ccc(F)c3C1)[nH]c(=O)c1nnc(C3CCC3)n12] | 6 |
| 38 | 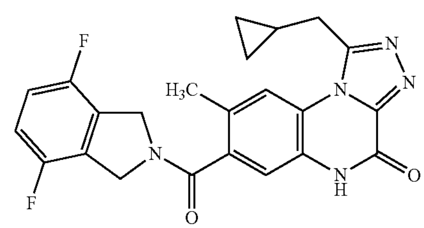 | 3 HCl |
| 39 (a) | 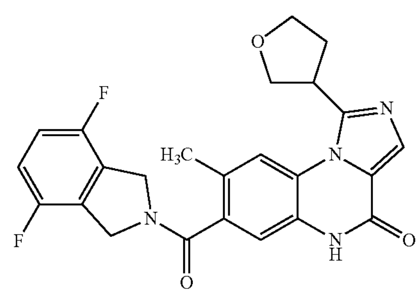 | 3.4 HCl chiral |

TABLE 30
| Ex | Structure | Syn |
|---|---|---|
| 39 (b) | 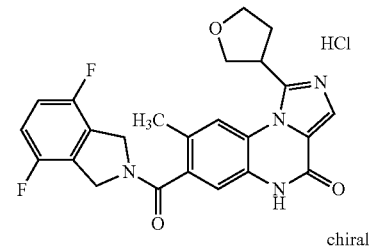 [SMILES: Cc1cc2c(cc1C(=O)N1Cc3c(F)ccc(F)c3C1)[nH]c(=O)c1cnc(C3CCOC3)n12 ; Cl] HCl chiral | 3, 4 |
| 40 (a) | 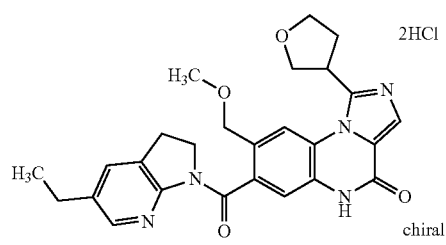 [SMILES: CCc1cnc2c(c1)CCN2C(=O)c1cc2[nH]c(=O)c3cnc(C4CCOC4)n3c2cc1COC ; "2HCl"] 2HCl chiral | 3, 4 |
| 40 (b) | 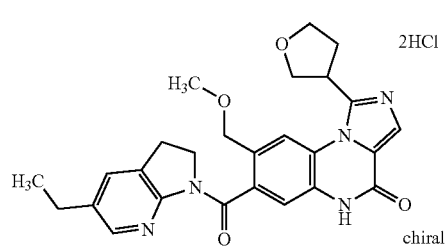 [SMILES: CCc1cnc2c(c1)CCN2C(=O)c1cc2[nH]c(=O)c3cnc(C4CCOC4)n3c2cc1COC ; "2HCl"] 2HCl chiral | 3, 4 |
| 41 | 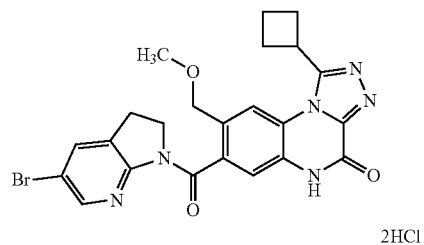 [SMILES: COCc1cc2c(cc1C(=O)N1CCc3cc(Br)cnc31)[nH]c(=O)c1nnc(C3CCC3)n12 ; "2HCl"] 2HCl | 6 |
| 42 | 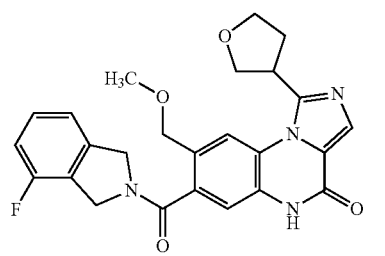 [SMILES: COCc1cc2c(cc1C(=O)N1Cc3cccc(F)c3C1)[nH]c(=O)c1cnc(C3CCOC3)n12] | 3 |
TABLE 31
| Ex | Structure | Syn |
|---|---|---|
| 43 (a) | 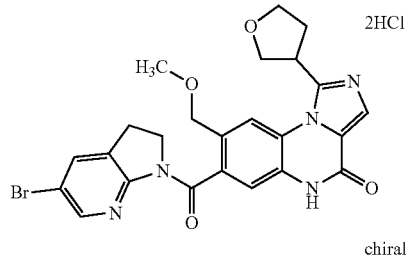 [SMILES: COCc1cc2c(cc1C(=O)N1CCc3cc(Br)cnc31)[nH]c(=O)c1cnc(C3CCOC3)n12 ; "2HCl" ; "chiral"] 2HCl chiral | 3, 4 |
| 43 (b) | 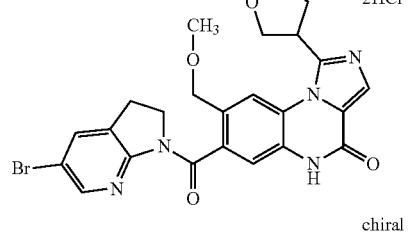 2HCl chiral | 3, 4 |
| 44 | 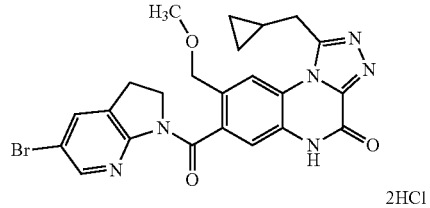 [SMILES: COCc1cc2c(cc1C(=O)N1CCc3cc(Br)cnc31)[nH]c(=O)c1nnc(CC3CC3)n12 ; "2HCl"] 2HCl | 6 |
| 45 (a) | 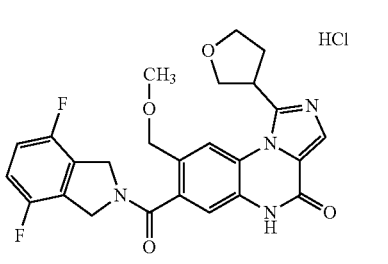 HCl chiral | 3, 4 |

TABLE 31-continued

| Ex | Structure | Syn |
|---|---|---|
| 45 (b) | 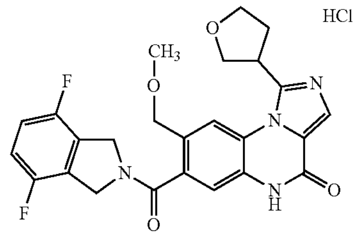 | 3, 4 |

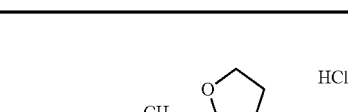

chiral

TABLE 32

| Ex | Structure | Syn |
|---|---|---|
| 46 | 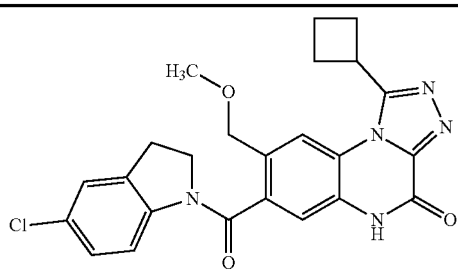 | 3 |

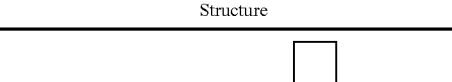

HCl

TABLE 32-continued

| Ex | Structure | Syn |
|---|---|---|
| 47 | 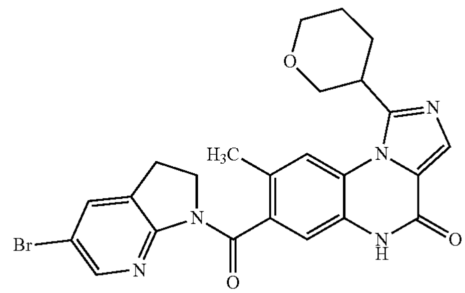 [SMILES: Cc1cc2c(cc1C(=O)N1CCc3cc(Br)cnc31)[nH]c(=O)c1cnc(C3CCCOC3)n12] | 6 |
| 48 | 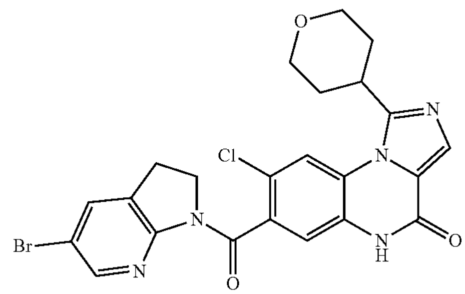 [SMILES: O=C(c1cc2[nH]c(=O)c3cnc(C4CCOCC4)n3c2cc1Cl)N1CCc2cc(Br)cnc21] | 6 |

TABLE 33

| Ex | Data |
|---|---|
| 1 | ESI+: 594.3, 596.3<br>NMR-DMSO-d6: 1.17-1.36 (1H, m), 1.71-2.36 (6H, m), 3.05-3.24 (2H, m), 3.25-3.65 (8H, m), 3.80-4.29 (5H, m), 7.27 (1H, s), 7.42 (1H, s), 7.82 (1H, s), 7.83 (1H, s), 7.89 (1H, s), 11.36 (1H, s)<br>mp: 321-324 (dec.) |
| 2 | ESI+: 464.3<br>NMR-DMSO-d6: 1.86-2.04 (4H, m), 3.11-3.19 (2H, m), 3.62-4.28 (10H, m), 6.73 (0.2H, br), 6.82 (1H, s), 7.43 (1H, d, J = 6.8 Hz), 7.86 (1H, s), 7.92 (1H, d, J = 11.2 Hz), 8.79 (0.8H, s), 11.59 (1H, s)<br>mp: 275-277 |
| 3 | ESI+: 460.4<br>NMR-DMSO-d6: 1.69-1.91 (3H, m), 2.20-2.44 (4H, m), 3.09-3.18 (2H, m), 3.40-3.50 (1H, m), 3.63-3.80 (4H, m), 3.85 (3H, m), 3.92-4.02 (1H, m), 4.14-4.28 (1H, m), 6.37 (0.2H, br s), 6.73-6.87 (1H, m), 7.15-7.31 (1H, m), 7.72-7.95 (2H, m), 8.83 (0.8H, s), 11.46 (1H, s)<br>mp: 297-299 |
| 4 (a) | ESI+: 476.3<br>NMR-DMSO-d6: 2.41-2.60 (2H, m), 3.08-3.19 (2H, m), 3.21-3.33 (3H, m), 3.63-3.96 (7H, m), 4.09-4.61 (5H, m), 6.42 (0.2H, br), 6.77-6.86 (1H, m), 7.25-7.39 (1H, m), 7.88 (1H, s), 8.09-8.17 (1H, m), 8.80 (0.8H, s), 11.53-11.65 (1H, m)<br>mp: 178-180 (dec.)<br>RT: 9.32 min (eluant: MeCN/H2O = 30/70) |
| 4 (b) | ESI+: 476.3<br>NMR-DMSO-d6: 2.41-2.62 (2H, m), 3.08-3.19 (2H, m), 3.21-3.33 (3H, m), 3.60-3.99 (7H, m), 4.15-4.25 (2H, m), 4.31-4.41 (1H, m), 4.43-4.61 (2H, m), 6.42 (0.2H, br), 6.77-6.86 (1H, m), 7.25-7.39 (1H, m), 7.86 (1H, s), 8.09-8.17 (1H, m), 8.80 (0.8H, s), 11.50-11.62 (1H, m)<br>mp: 174-175<br>RT: 13.31 min (eluant: MeCN/H2O = 30/70) |
| 5 | ESI+: 508.2, 510.2<br>NMR-DMSO-d6: 1.60-1.74 (2H, m), 1.86-2.13 (3H, m), 2.22 (3H, s), 3.16 (2H, t, J = 8.4 Hz), 3.91-4.00 (1H, m), 4.20 (2H, t, J = 8.4 Hz), 4.57-4.64 (1H, m), 4.88 (1H, d, J = 4.1 Hz), 7.14 (1H, s), 7.79 (1H, s), 7.81-7.84 (1H, m), 7.88-7.91 (1H, m), 7.93 (1H, s),<br>11.29 (1H, s)<br>mp 296-303 |

TABLE 33-continued

| Ex | Data |
|---|---|
| 6 | ESI+: 429.4<br>NMR-DMSO-d6: 0.29-0.39 (2H, m), 0.58-0.67 (2H, m), 1.06-1.16 (3H, m), 1.32-1.45 (1H, m), 2.27 (3H, s), 3.10-3.12 (2H, m), 3.34-3.43 (2H, m), 3.92-4.70 (4H, m), 7.25 (1H, s), 7.51-7.73 (2H, m), 7.89 (1H, s), 12.03 (1H, s)<br>mp: 173-175 |
| 7 | ESI+: 478.4, 480.3<br>NMR-DMSO-d6: 0.88-1.50 (3H, m), 1.86-2.22 (4H, m), 2.28-2.48 (3H, m), 2.62-2.74 (0.75H, m), 3.36-3.52 (0.75H, m), 3.62-3.78 (2H, m), 3.90-4.10 (3H, m), 4.10-4.32 (0.5H, m), 4.60-5.24 (1H, m), 5.50-5.80 (0.25H, m), 6.78-6.92 (0.25H, m), 7.10-7.20 (0.25H, m), 7.24-7.48 (2.5H, m), 7.78-8.02 (1H, m), 8.06-8.26 (0.75H, m), 11.98-12.22 (1H, m)<br>mp: 324-326 |

TABLE 34

| Ex | Data |
|---|---|
| 8 | ESI+: 464.3, 466.3<br>NMR-DMSO-d6: 2.16-2.68 (4H, m), 2.77-3.22 (7H, m), 3.54-4.28 (5H, m), 5.59 (0.2H, br s), 6.82 (0.2H, br s), 7.20-7.89 (3.8H, m), 8.07-8.19 (0.8H, m), 12.00-12.11 (1H, m)<br>mp: 200-202 |
| 9 | ESI+: 508.4, 510.3<br>NMR-DMSO-d6 (measured at 80° C.): 1.89-2.19 (4H, m), 2.78 (3H, s), 2.82-3.00 (1H, m), 3.16 (3H, br s), 3.23-3.50 (3H, m), 3.60-3.79 (2H, m), 3.88-4.07 (3H, m), 4.19-4.88 (1H, m), 7.06 (1H, br s), 7.22-7.53 (2H, m), 7.85 (1H, s), 11.82 (1H, s) |
| 10 | ESI+: 533.3<br>NMR-DMSO-d6: 1.55-1.66 (1H, m), 1.87-2.12 (5H, m), 2.60-2.70 (1H, m), 3.06-3.16 (2H, m), 3.40-4.64 (13H, m), 5.80-5.94 (0.2H, m), 6.58-6.75 (0.2H, m), 7.02-7.20 (1.8H, m), 7.23-7.36 (1H, m), 7.47-7.63 (1H, m), 7.86 (1H, s), 7.09-7.16 (0.8H, m), 11.46 (1H, s)<br>mp: 177-180 |
| 11 | ESI+: 486.3<br>NMR-DMSO-d6: 1.88-2.09 (4H, m), 2.35-2.45 (3H, m), 2.62-2.83 (6H, m), 3.50-4.38 (7H, m), 4.53-4.76 (2H, m), 4.89-5.13 (2H, m), 7.24-7.60 (4H, m), 7.81-7.90 (2H, m), 10.20-10.43 (1H, m), 11.51 (1H, s)<br>mp: 227 (dec.) |
| 12 | ESI+: 467.4, 469.4<br>NMR-DMSO-d6: 1.83-2.06 (4H, m), 3.09-3.21 (2H, m), 3.60-3.73 (2H, m), 3.82-4.05 (5H, m), 6.00 (0.2H, br), 6.94 (0.2H, br), 7.31 (0.8H, d, J = 8.5 Hz), 7.39 (1H, s), 7.44 (1H, d, J = 6.2 Hz), 7.89 (1H, s), 7.91 (1H, d, J = 11.3 Hz), 8.10 (0.8H, d, J = 8.5 Hz), 11.62 (1H, s)<br>mp: 270 (dec.) |
| 13 | ESI+: 458.4<br>NMR-DMSO-d6: 1.08 (3H, t, J = 7.6 Hz), 1.89-2.08 (4H, m), 2.25 (3H, s), 2.42-2.55 (2H, m), 3.10-3.19 (2H, m), 3.63-3.73 (2H, m), 3.85-3.94 (1H, m), 3.94-4.03 (2H, m), 4.14-4.24 (2H, m), 7.14 (1H, s), 7.51-7.59 (2H, m), 7.80 (1H, br s), 7.83 (1H, s), 11.35 (1H, s)<br>mp: 331-333 |
| 14 | ESI+: 473.4<br>NMR-DMSO-d6: 1.88-2.07 (4H, m), 2.38 (3H, s), 3.16 (1.2H, s), 3.27-3.36 (1.8H, m), 3.61-3.73 (2H, m), 3.82-3.92 (1H, m), 3.93-4.02 (2H, m), 4.29 (0.8H, s), 4.45-4.55 (3.2H, m), 4.84-4.94 (2H, m), 7.15-7.39 (4H, m), 7.82 (1H, s), 7.87-7.89 (1H, m), 11.42 (1H, s)<br>mp: 217 (dec.) |
| 15 | ESI+: 508.3, 510.3<br>NMR-DMSO-d6: 2.15-2.72 (5H, m), 2.74-3.21 (6H, m), 3.59-3.82 (1H, m), 3.84-4.46 (4H, m), 5.53 (0.2H, br s), 6.95 (0.2H, br s), 7.19-7.84 (3.8H, m), 8.01-8.16 (0.8H, m), 12.01-12.11 (1H, m)<br>mp: 188-189 |
| 16 | ESI+: 448.3, 450.2<br>NMR-DMSO-d6: 0.27-0.43 (2H, m), 0.52-0.66 (2H, m), 1.02-1.44 (4H, m), 2.35-4.33 (8H, m), 5.44-5.75 (0.2H, m), 6.70-6.92 (0.2H, m), 7.13-7.53 (2.8H, m), 7.96 (1H, s), 8.10-8.25 (0.8H, m), 11.44-12.40 (1H, m) |

TABLE 35

| Ex | Data |
|---|---|
| 17 | ESI+: 432.4
NMR-DMSO-d6: 0.26-0.41 (2H, m), 0.54-0.65 (2H, m), 0.27-1.44 (4H, m), 2.30-2.83 (2H, m), 3.03-3.22 (2H, m), 3.30-3.51 (2H, m), 3.63-4.42 (2H, m), 5.52-5.69 (0.2H, m), 6.53-6.67 (0.2H, m), 6.99-7.38 (2.8H, m), 7.97 (1H, s), 8.11-8.24 (0.8H, m), 12.02-12.13 (1H, m) |
| 18 | ESI+: 492.9, 494.9
NMR-DMSO-d6: 0.30-0.40 (2H, m), 0.56-0.65 (2H, m), 1.14 (3H, t, J = 7.6 Hz), 1.31-1.42 (1H, m), 2.61 (2H, q, J = 7.6 Hz), 3.12-3.22 (2H, m), 3.38-3.45 (2H, m), 4.17-4.26 (2H, m), 7.18 (1H, s), 7.74-7.79 (1H, m), 7.87-7.91 (2H, m), 11.95 (1H, s) |
| 19 | ESI+: 498.0 |
| 20 | ESI+: 498.0 |
| 21 | ESI+: 480.4, 482.4
NMR-DMSO-d6: 1.87-2.05 (4H, m), 3.11-3.20 (2H, m), 3.57-3.67 (3H, m), 3.80-3.89 (5H, m), 3.94-4.02 (2H, m), 6.54 (0.2H, s), 6.77-6.85 (1H, m), 7.32-7.43 (1H, m), 7.81-7.91 (1H, m), 7.97-8.08 (1H, m), 8.81 (0.2H, s), 11.67 (1H, s)
mp: 314-316 (dec.) |
| 22 | ESI+: 447.3
NMR-DMSO-d6: 1.60-1.73 (2H, m), 1.87-2.13 (3H, m), 2.22 (0.6H, br s), 2.37 (2.4H, s), 3.08-3.18 (2H, m), 3.72-3.85 (1.6H, m), 3.93-4.03 (1H, m), 4.14-4.32 (0.4H, br s), 4.58-4.66 (1H, m), 4.76-5.00 (1H, m), 5.66 (0.2H, br s), 6.69 (0.2H, br s), 7.02-7.22 (2.8H, m), 7.80 (1H, s), 8.03 (1H, m), 8.12-8.20 (0.8H, m), 11.39 (1H, s)
mp 197-199 |
| 23 | ESI+: 524.3, 526.3
NMR-DMSO-d6: 1.92-2.13 (4H, m), 3.10-3.20 (2H, m), 3.55-3.65 (2H, m), 3.69 (3H, s), 3.92-4.40 (3H, m), 4.11-4.21 (2H, m), 7.29 (1H, s), 7.46 (1H, s), 7.80-7.85 (1H, m), 7.86-7.91 (1H, m), 8.02 (1H, s), 11.55 (1H, s)
mp: 316-319 (dec.) |
| 24 | ESI+: 479.3, 481.3
NMR-DMSO-d6: 0.31-0.37 (2H, m), 0.57-0.65 (2H, m), 1.32-1.43 (1H, m), 2.24 (3H, s), 3.13-3.20 (2H, m), 3.38 (1H, d, J = 6.6 Hz), 4.16-4.24 (2H, m), 7.20 (1H, s), 7.77 (1H, s), 7.86 (1H, s), 7.89 (1H, s), 11.97 (1H, s)
mp: 268-271 |
| 25 (a) | ESI+: 460.3
NMR-DMSO-d6: 2.17 (3H, br s), 2.38-2.60 (2H, m), 3.07-3.18 (2H, m), 3.20 (3H, s), 3.78-4.50 (9H, m), 7.26 (1H, s), 7.50-7.69 (2H, m), 7.88 (1H, s), 8.03 (1H, s), 11.52 (1H, s)
mp: 154-156
RT: 10.90 min (eluant: MeCN/H2O = 30/70) |
| 25 (b) | ESI+: 460.3
NMR-DMSO-d6: 2.17 (3H, br s), 2.38-2.60 (2H, m), 3.07-3.18 (2H, m), 3.20 (3H, s), 3.80-4.50 (9H, m), 7.27 (1H, s), 7.50-7.69 (2H, m), 7.88 (1H, s), 8.04 (1H, s), 11.53 (1H, s)
mp: 156-158
RT: 15.99 min (eluant: MeCN/H2O = 30/70) |

TABLE 36

| Ex | Data |
|---|---|
| 26 (a) | ESI+: 430.4
NMR-DMSO-d6: 2.18 (3H, s), 2.27 (3H, s), 2.35-2.65 (2H, m), 3.08-3.23 (2H, m), 3.83-4.64 (7H, m), 7.21 (1H, s), 7.50-7.75 (2H, m), 7.84-7.96 (2H, m), 11.49 (1H, s)
RT: 9.99 min (eluant: MeCN/H2O = 35/65) |
| 26 (b) | ESI+: 430.3
NMR-DMSO-d6: 2.18 (3H, s), 2.27 (3H, s), 2.37-2.64 (2H, m), 3.08-3.22 (2H, m), 3.84-4.63 (7H, m), 7.21 (1H, s), 7.50-7.75 (2H, m), 7.83-7.94 (2H, m), 11.48 (1H, s)
RT: 15.46 min (eluant: MeCN/H2O = 35/65) |
| 27 | ESI+: 446.4
NMR-DMSO-d6: 2.25-2.59 (5H, m), 3.07-3.22 (2H, m), 3.63-3.96 (7H, m), 4.06-4.31 (2H, m), 4.35-4.47 (1H, m), 6.36 (0.2H, s), 6.77-6.82 (1H, m), 7.19-7.26 (1H, m), 7.80 (1H, s), 7.93-8.03 (1H, m), 8.83 (0.8H, s), 11.46 (1H, s)
mp: 241-243 |
| 27 (a) | ESI+: 446.4
NMR-DMSO-d6: 2.24-2.70 (5H, m), 3.08-3.21 (2H, m), 3.63-4.31 (9H, m), 4.38-4.52 (1H, m), 6.36 (0.2H, br), 6.77-6.86 (1H, m), 7.19-7.31 (1H, m), 7.84-7.91 (1H, m), 7.93-8.04 (1H, m), 8.82 (0.8H, s), 11.53 (1H, s)
mp: 224-226
RT: 8.11 min (eluant: MeCN/H2O = 35/65) |
| 27 (b) | ESI+: 446.3
NMR-DMSO-d6: 2.24-2.70 (5H, m), 3.08-3.22 (2H, m), 3.62-3.96 (7H, m), 4.02-4.39 (2H, m), 4.40-4.52 (1H, m), 6.36 (0.2H, br), 6.77-6.87 (1H, m), 7.20-7.32 (1H, m), 7.85-7.91 (1H, m), 7.94-8.04 (1H, m), 8.82 (0.8H, s), 11.54 (1H, s)
mp: 227-229
RT: 13.23 min (eluant: MeCN/H2O = 35/65) |

TABLE 36-continued

| Ex | Data |
|---|---|
| 28 | ESI+: 444.3<br>NMR-DMSO-d6: 1.09 (3H, t, J = 7.6 Hz), 2.23 (3H, s), 2.37-2.52 (4H, m), 3.08-3.18 (2H, m), 3.86-3.92 (2H, m), 4.12-4.22 (4H, m), 4.36-4.45 (1H, m), 7.13 (1H, s), 7.53 (1H, s), 7.56 (1H, s), 7.80 (1H, s), 7.86 (1H, s), 11.33 (1H, s)<br>mp: 275 (dec.) |
| 28<br>(a) | ESI+: 443.9<br>NMR-DMSO-d6: 1.12 (3H, t, J = 7.6 Hz), 2.30 (3H, s), 2.37-2.65 (4H, m), 3.12-3.24 (2H, m), 3.83-4.55 (7H, m), 7.26 (1H, br), 7.60-7.88 (2H, m), 7.88-8.18 (2H, m), 11.58 (1H, br)<br>RT: 9.29 min (eluant: MeCN/H2O = 40/60) |
| 28<br>(b) | ESI+: 444.0<br>NMR-DMSO-d6: 1.12 (3H, t, J = 7.6 Hz), 2.29 (3H, s), 2.37-2.64 (4H, m), 3.17 (2H, t, J = 8.0 Hz), 3.54-4.06 (2H, m), 4.08-4.25 (4H, m), 4.42-4.52 (1H, m), 7.26 (1H, s), 7.57-7.81 (2H, m), 7.86-7.98 (2H, m), 11.54 (1H, s)<br>RT: 17.77 min (eluant: MeCN/H2O = 40/60) |
| 29 | ESI+: 494.4, 496.4<br>NMR-DMSO-d6: 2.24 (3H, s), 2.34-2.56 (2H, m), 3.11-3.22 (2H, m), 3.82-3.96 (2H, m), 4.10-4.25 (4H, m), 4.33-4.47 (1H, m), 7.15 (1H, s), 7.80 (1H, s), 7.81-7.91 (3H, m), 11.35 (1H, s)<br>mp: 295 (dec.) |

TABLE 37

| Ex | Data |
|---|---|
| 29<br>(a) | ESI+: 494.1, 496.1<br>NMR-DMSO-d6: 2.24 (3H, s), 2.36-2.57 (2H, m), 3.12-3.21 (2H, m), 3.86-3.94 (2H, m), 4.12-4.26 (4H, m), 4.41-4.50 (1H, m), 7.18 (1H, s), 7.79-7.82 (1H, m), 7.86-7.94 (3H, m), 11.48 (1H, s)<br>mp: 179-181<br>RT: 10.82 min (eluant: MeCN/H2O = 40/60) |
| 29<br>(b) | ESI+: 493.9, 495.9<br>NMR-DMSO-d6: 2.24 (3H, s), 2.36-2.56 (2H, m), 3.12-3.22 (2H, m), 3.86-3.95 (2H, m), 4.12-4.26 (4H, m), 4.40-4.50 (1H, m), 7.18 (1H, s), 7.79-7.83 (1H, m), 7.86-7.93 (3H, m), 11.48 (1H, s)<br>mp: 184-186<br>RT: 21.49 min (eluant: MeCN/H2O = 40/60) |
| 30 | ESI+: 451.3<br>NMR-DMSO-d6: 2.21-2.51 (5H, m), 3.05-3.15 (2H, m), 3.74-3.93 (4H, m), 4.11-4.24 (2H, m), 4.36-4.46 (1H, m), 5.53 (0.2H, br), 7.24 (1H, s), 7.42 (1H, t, J = 8.8 Hz), 7.80 (1H, s), 7.95 (1H, s), 8.03-8.16 (0.8H, m), 11.45 (1H, s)<br>mp: 305 (dec.) |
| 30<br>(a) | ESI+: 451.0<br>NMR-DMSO-d6: 2.21-2.51 (5H, m), 3.05-3.16 (2H, m), 3.67-3.95 (4H, m), 4.13-4.25 (2H, m), 4.39-4.50 (1H, m), 5.53 (0.2H, br), 7.28 (1H, s), 7.38-7.47 (1H, m), 7.84-7.90 (1H, m), 7.97 (1H, s), 8.04-8.18 (0.8H, m), 11.54 (1H, s)<br>mp: 178-180<br>RT: 10.20 min (eluant: MeCN/H2O = 45/55) |
| 30<br>(b) | ESI+: 451.3<br>NMR-DMSO-d6: 2.20-2.62 (5H, m), 3.05-3.16 (2H, m), 3.68-4.00 (4H, m), 4.11-4.29 (2H, m), 4.37-4.49 (1H, m), 5.54 (0.2H, br), 7.27 (1H, s), 7.38-7.48 (1H, m), 7.85 (1H, s), 7.97 (1H, s), 8.05-8.20 (0.8H, m), 11.51 (1H, s)<br>mp: 189-191<br>RT: 16.26 min (eluant: MeCN/H2O = 45/55) |
| 31 | ESI+: 477.4, 478.4<br>NMR-DMSO-d6: 1.10-1.46 (3H, m), 1.78-2.11 (4H, m), 2.11-2.62 (3H, m), 3.23-3.38 (0.8H, m), 3.38-3.56 (1H, m), 3.56-3.82 (2.2H, m), 3.82-4.10 (3.8H, m), 4.25-4.51 (0.2H, m), 5.55-5.78 (0.2H, m), 6.80-7.02 (0.2H, m), 7.16-7.49 (2.8H, m), 7.89 (1H, s), 7.95 (1H, s), 8.05-8.28 (0.8H, m), 11.52 (1H, br s)<br>mp: 221-224 |
| 32 | ESI+: 478.4, 480.4<br>NMR-DMSO-d6: 1.14-1.39 (3H, m), 1.88-2.14 (4H, m), 2.17-2.59 (3H, m), 3.24-3.38 (0.8H, m), 3.40-3.53 (1H, m), 3.63-3.78 (2.2H, m), 3.84-4.06 (3.8H, m), 4.32-4.48 (.2H, m), 5.50-5.75 (0.2H, m), 6.74-6.93 (0.2H, m), 7.22-7.46 (2.8H, m), 7.83-7.93 (1H, m), 8.06-8.21 (0.8H, m), 12.13 (1H, br s)<br>mp: 231-234 |
| 33 | ESI+: 537.2, 539.2<br>NMR-DMSO-d6: 1.39 (6H, s), 1.91-2.14 (4H, m), 2.27 (3H, s), 3.63-3.76 (2H, m), 3.92-4.04 (5H, m), 7.27 (1H, s), 7.80 (1H, s), 7.82 (1H, d, J = 2.28 Hz), 8.0 (1H, d, J = 2.28 Hz), 11.99 (1H, s)<br>mp: 341 (dec.) |

TABLE 38

| Ex | Data |
|---|---|
| 34 | ESI+: 509.3, 511.3<br>NMR-DMSO-d6: 2.24 (3H, s), 2.34-2.63 (2H, m), 2.78-2.93 (2H, m), 3.12-3.24 (5H, m), 3.98-4.43 (4H, m), 7.20 (1H, s), 7.54 (1H, s), 7.80-7.82 (1H, m), 7.88-7.92 (1H, m), 11.99 (1H, s) |
| 35 | ESI+: 493.3, 495.3<br>NMR-DMSO-d6: 1.14 (3H, t, J = 7.5 Hz), 1.93-2.09 (1H, m), 2.10-2.25 (1H, m), 2.36-2.75 (6H, m), 3.11-3.21 (2H, m), 4.05-4.81 (3H, m), 7.18 (1H, s), 7.65 (1H, s), 7.75-7.80 (1H, m), 7.87-7.90 (1H, m), 11.97 (1H, s) |
| 36 | ESI+: 436.4<br>NMR-DMSO-d6: 1.94-2.07 (1H, m), 2.11-2.24 (1H, m), 2.40 (3H, s), 2.54-2.70 (4H, m), 4.30-4.41 (1H, m), 4.58 (2H, br s), 4.96 (2H, br s), 7.16-7.32 (3H, m), 7.71 (1H, s), 12.0 (1H, br s) |
| 37 | ESI+: 450.4<br>NMR-DMSO-d6: 1.23 (3H, t, J = 3.0 Hz), 1.94-2.08 (1H, m), 2.10-2.26 (1H, m), 2.40-2.82 (6H, m), 4.31-4.42 (1H, m), 4.57 (2H, br s), 4.97 (2H, br s), 7.14-7.32 (3H, m), 7.71 (1H, s), 12.0 (1H, br s) |
| 38 | ESI+: 436.3<br>NMR-DMSO-d6: 0.31-0.37 (2H, m), 0.57-0.64 (2H, m), 1.33-1.44 (1H, m), 2.39 (3H, s), 3.37 (2H, d, J = 4.0 Hz), 4.57 (2H, br s), 4.96 (2H, br s), 7.17-7.28 (2H, m), 7.32 (1H, br s), 7.95 (1H, br s), 12.1 (1H, br s) |
| 39 (a) | ESI+: 451.3<br>NMR-DMSO-d6: 2.35-2.62 (5H, m), 3.91 (2H, t, J = 6.8 Hz), 4.07-4.51 (3H, m), 4.60 (2H, s), 4.96 (2H, s), 7.16-7.32 (3H, m), 7.88 (1H, s), 7.95 (1H, s), 11.51 (1H, s)<br>mp: 188-190<br>RT: 10.44 min (eluant: MeCN/H2O = 35/65) |
| 39 (b) | ESI+: 451.4<br>NMR-DMSO-d6: 2.35-2.62 (5H, m), 3.84-3.96 (2H, m), 4.13-4.26 (2H, m), 4.36-4.48 (1H, m), 4.60 (2H, s), 4.96 (2H, s), 7.16-7.30 (3H, m), 7.84 (1H, s), 7.95 (1H, s), 11.46 (1H, s)<br>mp: 185-187<br>RT: 14.01 min (eluant: MeCN/H2O = 35/65) |
| 40 (a) | ESI+: 474.3<br>NMR-DMSO-d6: 1.12 (3H, t, J = 7.6 Hz), 2.38-2.61 (4H, m), 3.17 (2H, t, J = 8.0 Hz), 3.22 (3H, s), 3.91 (2H, t, J = 6.8 Hz), 4.01-4.57 (7H, m), 7.33 (1H, s), 7.53-7.86 (2H, m), 7.93 (1H, s), 8.06 (1H, s), 11.62 (1H, s)<br>mp: 158-160<br>RT: 10.58 min (eluant: MeCN/H2O = 33/67) |
| 40 (b) | ESI+: 474.3<br>NMR-DMSO-d6: 1.12 (3H, t, J = 7.6 Hz), 2.38-2.64 (4H, m), 3.17 (2H, t, J = 8.0 Hz), 3.22 (3H, s), 3.91 (2H, t, J = 6.8 Hz), 4.00-4.72 (7H, m), 7.33 (1H, s), 7.53-7.83 (2H, m), 7.93 (1H, s), 8.06 (1H, s), 11.62 (1H, s)<br>mp: 158-160<br>RT: 16.53 min (eluant: MeCN/H2O = 33/67) |
| 41 | ESI+: 509.3, 511.2<br>NMR-DMSO-d6: 1.95-2.23 (2H, m), 2.57-2.66 (4H, m), 3.16 (2H, t, J = 8.0 Hz), 3.20 (3H, s), 4.18 (2H, t, J = 8.0 Hz), 4.23-4.34 (1H, m), 4.42 (2H, s), 7.28 (1H, s), 7.75-7.78 (1H, m), 7.80 (1H, s), 7.88-7.90 (1H, m), 12.07 (1H, s)<br>mp: 174-176 |

TABLE 39

| Ex | Data |
|---|---|
| 42 | ESI+: 463.3<br>NMR-DMSO-d6: 2.45 (2H, q, J = 7.2 Hz), 3.28 (3H, s), 3.85-3.95 (2H, m), 4.20 (2H, d, J = 6.1 Hz), 4.28-4.38 (1H, m), 4.53 (2H, s), 4.60 (2H, s), 4.92 (2H, s), 7.09-7.19 (1.5H, m), 7.26-7.30 (0.5H, m), 7.31-7.43 (2H, m), 7.82 (1H, d, J = 2.5 Hz), 8.10 (1H, s), 11.5 (1H, s)<br>mp: 154-156 |
| 43 (a) | ESI+: 524.3, 526.2<br>NMR-DMSO-d6: 2.35-2.62 (2H, m), 3.07-3.24 (5H, m), 3.60-4.00 (2H, m), 4.11-4.26 (4H, m), 4.32-4.45 (3H, m), 7.24 (1H, s), 7.76-7.83 (1H, m), 7.85-7.95 (2H, m), 8.02 (1H, s), 11.53 (1H, s)<br>mp: 212-213<br>RT: 7.63 min (eluant: MeCN/H2O = 45/55) |
| 43 (b) | ESI+: 524.0, 526.0<br>NMR-DMSO-d6: 2.37-2.62 (2H, m), 3.11-3.24 (5H, m), 3.90 (2H, t, J = 6.8 Hz), 4.13-4.23 (4H, m), 4.31-4.62 (3H, m), 7.24 (1H, s), 7.78-7.83 (1H, m), 7.85-7.92 (2H, m), 8.02 (1H, s), 11.51 (1H, s)<br>mp: 211-212<br>RT: 12.62 min (eluant: MeCN/H2O = 45/55) |
| 44 | ESI+: 509.2, 511.3<br>NMR-DMSO-d6: 0.32-0.37 (2H, m), 0.57-0.64 (2H, m), 1.31-1.40 (1H, m), 3.13-3.21 (5H, m), 3.34-3.41 (2H, m), 4.18 (2H, t, J = 8.4 Hz), 4.41 (2H, s), 7.29 (1H, s), |

TABLE 39-continued

| Ex | Data |
|---|---|
| | 7.75-7.78 (1H, m), 7.87-7.90 (1H, m), 8.02 (1H, s), 12.08 (1H, s)<br>mp: 168-170 |
| 45<br>(a) | ESI+: 481.3<br>NMR-DMSO-d6: 2.39-2.62 (2H, m), 3.29 (3H, s), 3.85-3.95 (2H, m), 4.15-4.25 (2H, m), 4.29-4.41 (1H, m), 4.42-4.78 (4H, m), 4.96 (2H, s), 7.16-7.29 (2H, m), 7.36 (1H, s), 7.87 (1H, s), 8.10 (1H, s), 11.57 (1H, s)<br>mp: 200-201<br>RT: 9.53 min (eluant: MeCN/H2O = 35/65) |
| 45<br>(b) | ESI+: 480.9<br>NMR-DMSO-d6: 2.39-2.62 (2H, m), 3.29 (3H, s), 3.85-3.95 (2H, m), 4.15-4.24 (2H, m), 4.29-4.41 (1H, m), 4.53 (2H, s), 4.63 (2H, s), 4.96 (2H, s), 7.16-7.30 (2H, m), 7.35 (1H, s), 7.85 (1H, s), 8.10 (1H, s), 11.54 (1H, s)<br>mp: 198-200<br>RT: 12.91 min (eluant: MeCN/H2O = 35/65) |
| 46 | ESI+: 464.4, 466.4<br>NMR-DMSO-d6: 1.95-2.25 (2H, m), 2.53-2.69 (4H, m), 3.01-3.35 (4H, m), 3.67-3.89 (1.6H, m), 4.10-4.84 (4.4H, m), 5.65 (0.2H, br), 6.82 (0.2H, br), 7.21-7.45 (2.8H, m), 7.87 (1H, s), 8.05-8.22 (0.8H, m), 12.15 (1H, s)<br>mp: 170-172 |
| 47 | ESI+: 508.0, 510.0<br>NMR-DMSO-d6: 1.73 (1H, m), 1.87 (2H, m), 2.24 (3H, s), 2.27 (1H, m), 3.17 (2H, t, J = 8.3 Hz), 3.46 (1H, m), 3.72 (1H, m), 3.76 (1H, m), 3.95 (1H, m), 4.18 (1H, m), 4.20 (2H, t, J = 8.3 Hz), 7.15 (1H, s), 7.78 (1H, s), 7.81 (1H, s), 7.82 (1H, m), 7.90 (1H, m), 11.4 (1H, s)<br>mp: 300-305 (dec.) |

TABLE 40

| Ex | Data |
|---|---|
| 48 | ESI+: 527.9, 529.9<br>NMR-DMSO-d6: 1.84-2.05 (4H, Br), 3.18 (2H, t, J = 8.1 Hz), 3.62 (2H, m), 3.85 (1H, m), 3.97 (2H, m), 4.22 (2H, t, J = 8.1 Hz), 7.30 (1H, s), 7.83 (1H, s), 7.86 (1H, s), 7.91 (1H, s), 7.93 (1H, s), 11.60 (1H, s)<br>mp: 270-275 (dec.) |

TABLE 41

| No | Structure |
|---|---|
| 1 | 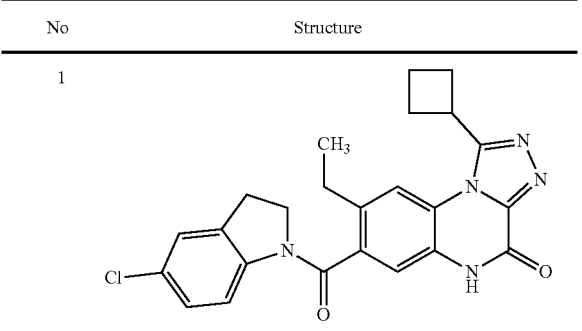 |
| 2 | 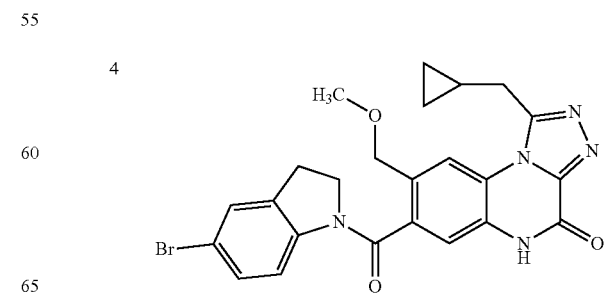 |

TABLE 41-continued

| No | Structure |
|---|---|
| 3 | 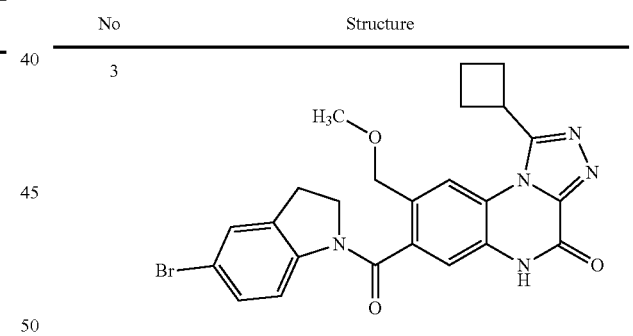 |
| 4 | 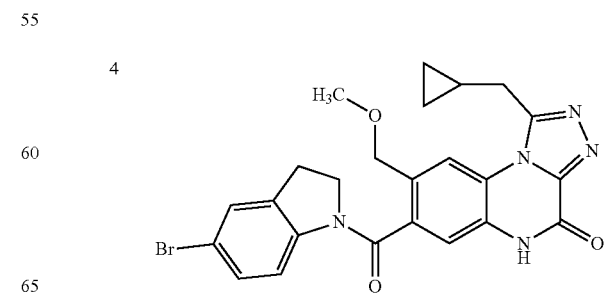 |

TABLE 41-continued

| No | Structure |
|----|-----------|
| 5  | 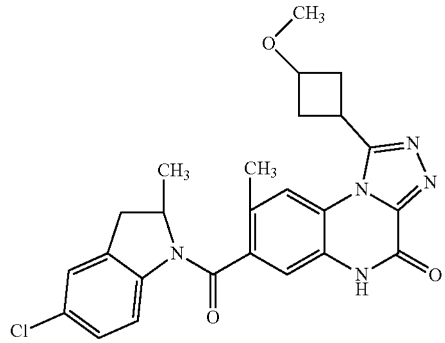 [SMILES: COC1CC(c2nnc3c(=O)[nH]c4cc(C(=O)N5c6ccc(Cl)cc6CC5C)c(C)cc4n23)C1]          |
| 6  | 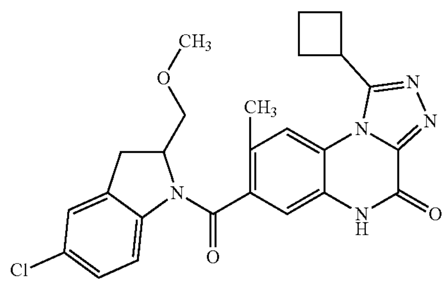 [SMILES: COCC1Cc2cc(Cl)ccc2N1C(=O)c1cc2[nH]c(=O)c3nnc(C4CCC4)n3c2cc1C]          |
| 7  | 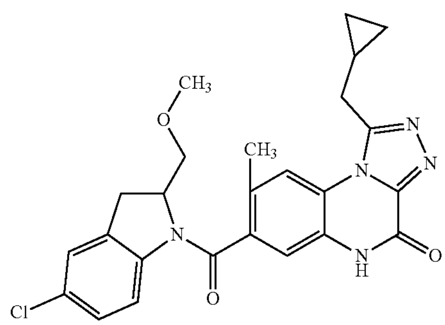 [SMILES: COCC1Cc2cc(Cl)ccc2N1C(=O)c1cc2[nH]c(=O)c3nnc(CC4CC4)n3c2cc1C]          |
| 8  | 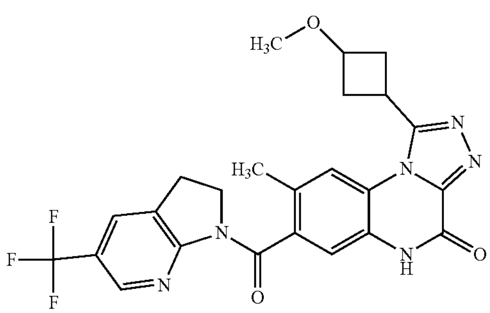 [SMILES: COC1CC(c2nnc3c(=O)[nH]c4cc(C(=O)N5CCc6cc(C(F)(F)F)cnc65)c(C)cc4n23)C1]          |
| 9  | 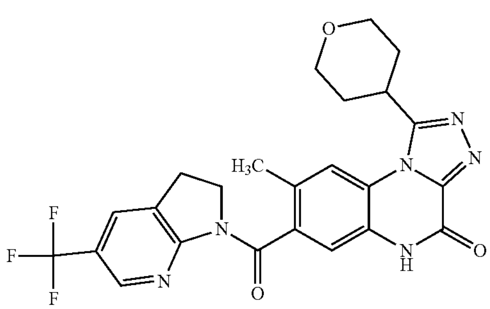 [SMILES: Cc1cc2c(cc1C(=O)N1CCc3cc(C(F)(F)F)cnc31)[nH]c(=O)c1nnc(C3CCOCC3)n12]          |

TABLE 41-continued

| No | Structure |
|----|-----------|
| 10 |           |

TABLE 42

| No | Structure |
|----|-----------|
| 11 | 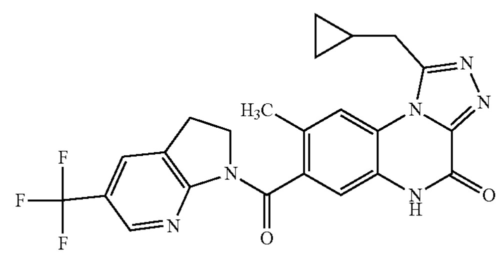 [SMILES: Cc1cc2c(cc1C(=O)N1CCc3cc(C(F)(F)F)cnc31)[nH]c(=O)c1nnc(CC3CC3)n12]          |
| 12 | 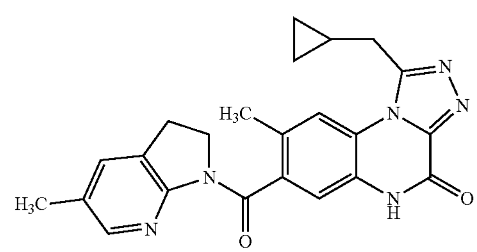 [SMILES: Cc1cnc2c(c1)CCN2C(=O)c1cc2[nH]c(=O)c3nnc(CC4CC4)n3c2cc1C]          |
| 13 | 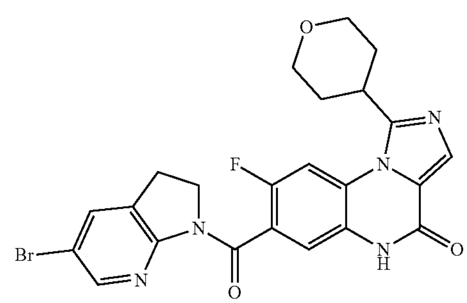 [SMILES: O=C(c1cc2[nH]c(=O)c3cnc(C4CCOCC4)n3c2cc1F)N1CCc2cc(Br)cnc21]          |
| 14 | 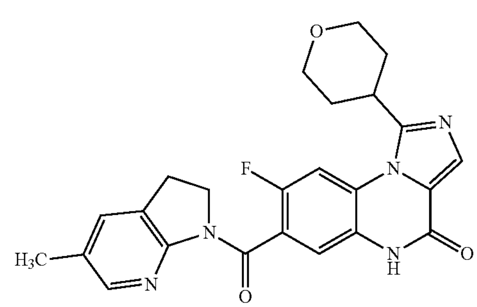 [SMILES: Cc1cnc2c(c1)CCN2C(=O)c1cc2[nH]c(=O)c3cnc(C4CCOCC4)n3c2cc1F]          |

TABLE 42-continued

| No | Structure |
|---|---|
| 15 | (structure) |
| 16 | (structure) |
| 17 | (structure) |
| 18 | (structure) |
| 19 | (structure) |

TABLE 42-continued

| No | Structure |
|---|---|
| 20 | (structure) |

TABLE 43

| No | Structure |
|---|---|
| 21 | (structure) |
| 22 | (structure) |
| 23 | (structure) |
| 24 | (structure) |

TABLE 43-continued
| No | Structure |
|---|---|
| 25 | 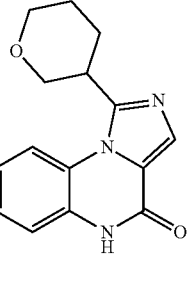 |
| 26 | 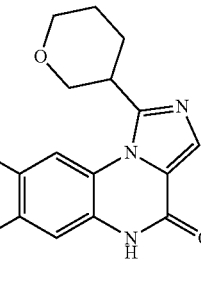 |
| 27 | 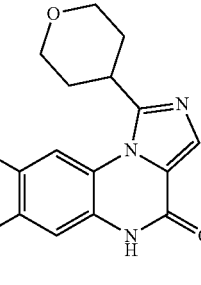 |
| 28 | 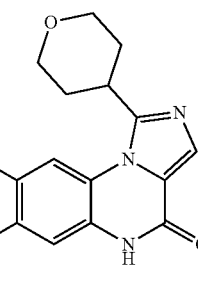 |
TABLE 44
| No | Structure |
|---|---|
| 29 | 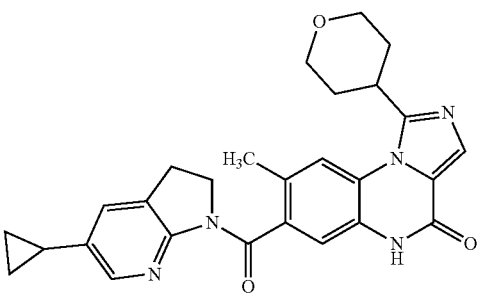 [SMILES: Cc1cc2c(cc1C(=O)N1CCc3cc(C4CC4)cnc31)[nH]c(=O)c1cnc(C3CCOCC3)n12] |
| 30 | 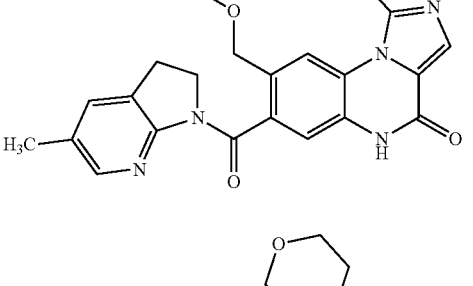 |
| 31 | 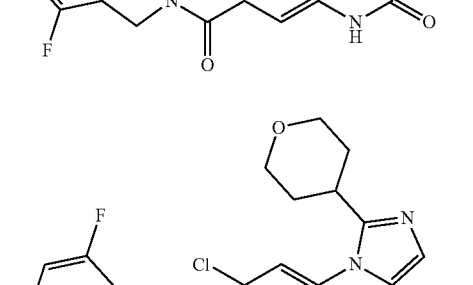 |
| 32 | 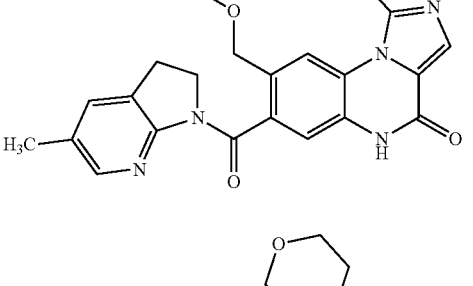 |
| 33 | 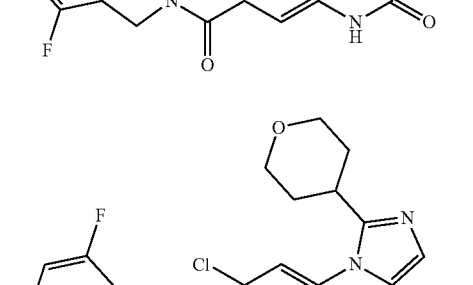 |

TABLE 44-continued
| No | Structure |
|----|-----------|
| 34 | 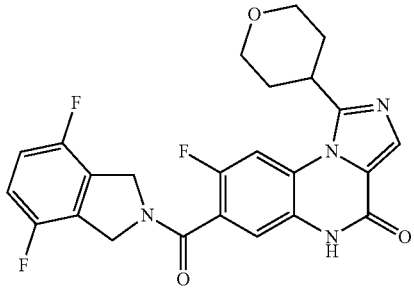 [SMILES: O=C(c1cc2[nH]c(=O)c3cnc(C4CCOCC4)n3c2cc1F)N1Cc2c(F)ccc(F)c2C1] |
| 35 | 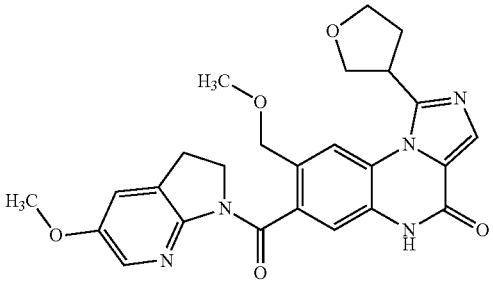 [SMILES: COCc1cc2c(cc1C(=O)N1CCc3cc(OC)cnc31)[nH]c(=O)c1cnc(C3CCOC3)n12] |
| 36 | 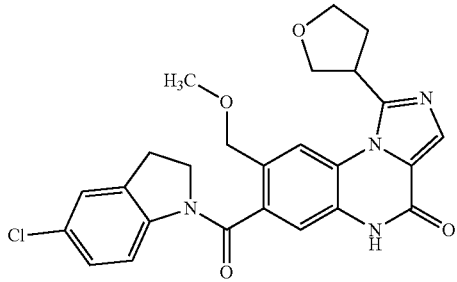 [SMILES: COCc1cc2c(cc1C(=O)N1CCc3cc(Cl)ccc31)[nH]c(=O)c1cnc(C3CCOC3)n12] |
TABLE 45
| No | Structure |
|----|-----------|
| 37 | 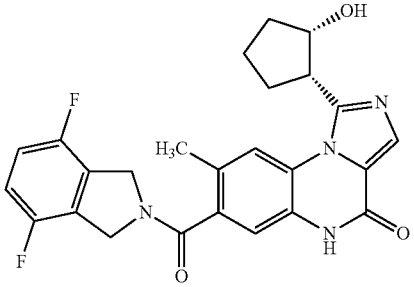 [SMILES: Cc1cc2c(cc1C(=O)N1Cc3c(F)ccc(F)c3C1)[nH]c(=O)c1cnc([C@@H]3CCC[C@@H]3O)n12] |
TABLE 45-continued
| No | Structure |
|----|-----------|
| 38 | 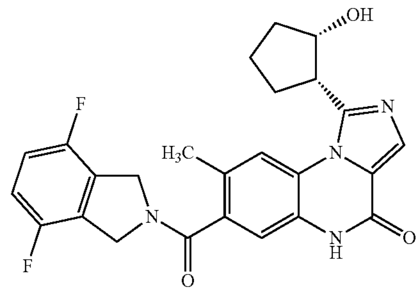 |
| 39 | 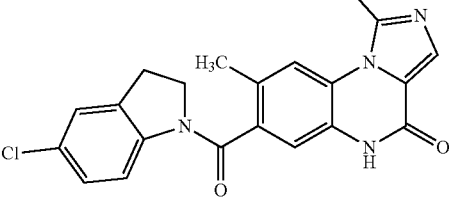 |
| 40 | 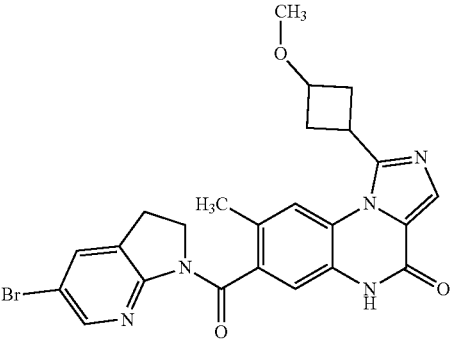 [SMILES: COC1CC(c2ncc3c(=O)[nH]c4cc(C(=O)N5CCc6cc(Cl)ccc65)c(C)cc4n23)C1] |
| 41 | 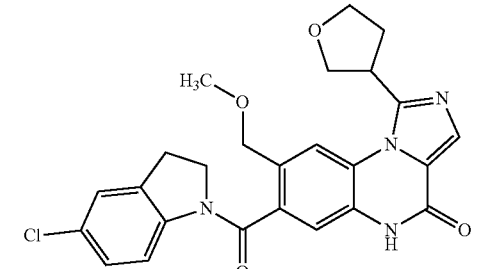 |

TABLE 45-continued
| No | Structure |
|---|---|
| 42 | 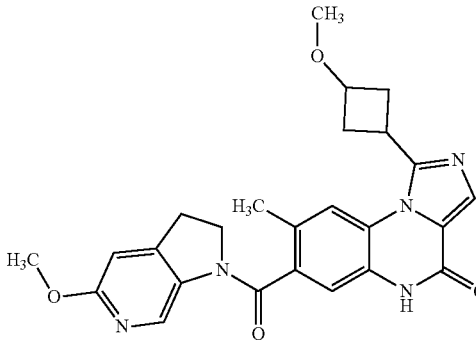 |
| 43 | 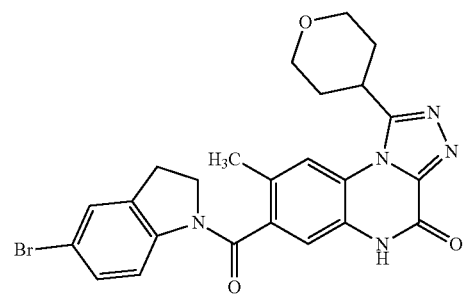 [SMILES: Cc1cc2c(cc1C(=O)N1CCc3cc(Br)ccc31)[nH]c(=O)c1nnc(C3CCOCC3)n12] |
| 44 | 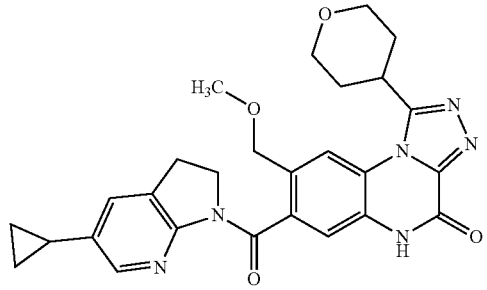 [SMILES: COCc1cc2c(cc1C(=O)N1CCc3cc(C4CC4)cnc31)[nH]c(=O)c1nnc(C3CCOCC3)n12] |
TABLE 46
| No | Structure |
|---|---|
| 45 | 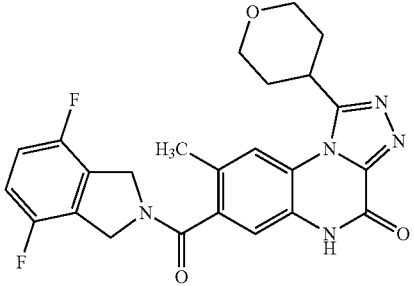 [SMILES: Cc1cc2c(cc1C(=O)N1Cc3c(F)ccc(F)c3C1)[nH]c(=O)c1nnc(C3CCOCC3)n12] |
| 46 | 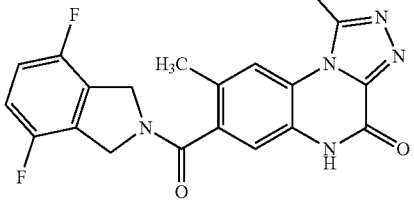 |
TABLE 46-continued
| No | Structure |
|---|---|
| 47 | 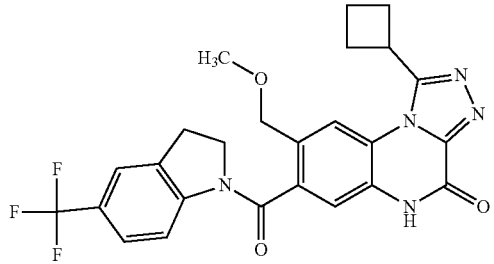 [SMILES: COCc1cc2c(cc1C(=O)N1CCc3cc(C(F)(F)F)ccc31)[nH]c(=O)c1nnc(C3CCC3)n12] |
| 48 | 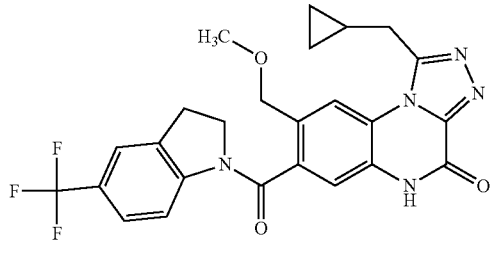 [SMILES: COCc1cc2c(cc1C(=O)N1CCc3cc(C(F)(F)F)ccc31)[nH]c(=O)c1nnc(CC3CC3)n12] |
| 49 | 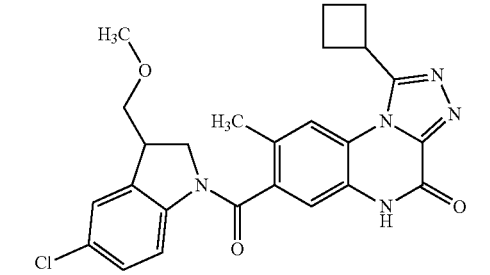 [SMILES: COCC1CN(C(=O)c2cc3[nH]c(=O)c4nnc(C5CCC5)n4c3cc2C)c2ccc(Cl)cc21] |
| 50 | 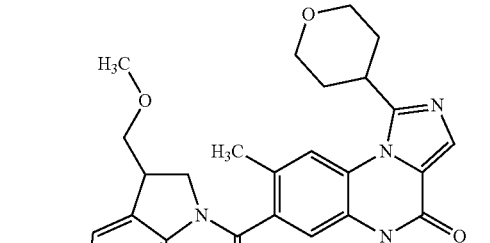 |
| 51 | 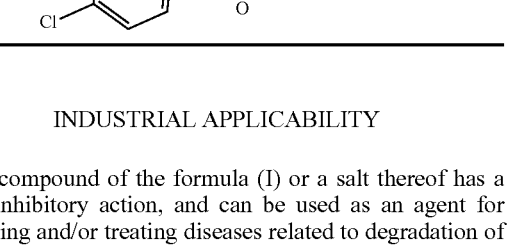 |
INDUSTRIAL APPLICABILITY
The compound of the formula (I) or a salt thereof has a PDE9-inhibitory action, and can be used as an agent for preventing and/or treating diseases related to degradation of cGMP by PDE9, for example, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis or urethra calculus.

The invention claimed is:

1. A compound selected from the group consisting of
   (+)-7-[(5-methoxy-2,3-dihydro-1H-pyrrolo[2,3-c]pyridin-1-yl)carbonyl]-8-methyl-1-(tetrahydrofuran-3-yl)imidazo[1,5-a]quinoxalin-4(5H)-one,
   (+)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one,
   (+)-8-(methoxymethyl)-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one,
   (+)-7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one,
   (+)-7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one; and
   (+)-7-[(5,6-difluoro-2,3-dihydro-1H-indol-1-yl)carbonyl]-8-methyl-1-(tetrahydrofuran-3-yl)imidazo[1,5-a]quinoxalin-4(5H)-one;
   or a pharmaceutically acceptable salt of said compound.

2. The compound as set forth in claim 1, which is (+)-7-[(5-methoxy-2,3-dihydro-1H-pyrrolo[2,3-c]pyridin-1-yl)carbonyl]-8-methyl-1-(tetrahydrofuran-3-yl)imidazo[1,5-a]quinoxalin-4(5H)-one or a pharmaceutically acceptable salt thereof.

3. The compound as set forth in claim 1, which is (+)-7-[(5-methoxy-2,3-dihydro-1H-pyrrolo[2,3-c]pyridin-1-yl)carbonyl]-8-(methoxymethyl)-1-(tetrahydrofuran-3-yl)imidazo[1,5-a]quinoxalin-4(5H)-one or a pharmaceutically acceptable salt thereof.

4. The compound as set forth in claim 1, which is (+)-8-(methoxymethyl)-7-[(5-methyl-2,3-dihydro-1H-pyrrolo[2,3-b]pyridin-1-yl)carbonyl]-1-(tetrahydrofuran-3-yl)imidazo[1,5-a]quinoxalin-4(5H)-one or a pharmaceutically acceptable salt thereof.

5. The compound as set forth in claim 1, which is (+)-7-[(5-bromo-2,3-dihydro-1H-pyrrolo[2,3-b]pyridin-1-yl)carbonyl]-8-methyl-1-(tetrahydrofuran-3-yl)imidazo[1,5-a]quinoxalin-4(5H)-one or a pharmaceutically acceptable salt thereof.

6. The compound as set forth in claim 1, which is (+)-7-[(5-bromo-2,3-dihydro-1H-pyrrolo[2,3-b]pyridin-1-yl)carbonyl]-8-(methoxymethyl)-1-(tetrahydrofuran-3-yl)imidazo[1,5-a]quinoxalin-4(5H)-one or a pharmaceutically acceptable salt thereof.

7. The compound as set forth in claim 1, which is (+)-7-[(5,6-difluoro-2,3-dihydro-1H-indol-1-yl)carbonyl]-8-methyl-1-(tetrahydrofuran-3-yl)imidazo[1,5-a]quinoxalin-4(5H)-one or a pharmaceutically acceptable salt thereof.

8. A pharmaceutical composition, comprising a compound or pharmaceutically acceptable salt thereof as set forth in claim 1, and a pharmaceutically acceptable excipient.

9. A method for treating underactive bladder, voiding dysfunction in the underactive bladder, benign prostatic hyperplasia, or voiding dysfunction accompanying benign prostatic hyperplasia, comprising administering to a subject in need thereof an effective amount of a compound or pharmaceutically acceptable salt thereof as set forth in claim 1.

* * * * *